US009914932B2

United States Patent
Dai et al.

(10) Patent No.: US 9,914,932 B2
(45) Date of Patent: Mar. 13, 2018

(54) AGROBACTERIUM-MEDIATED TRANSFORMATION OF LIPOMYCES

(71) Applicant: Battelle Memorial Institute, Richland, WA (US)

(72) Inventors: Ziyu Dai, Richland, WA (US); Jon K. Magnuson, Richland, WA (US); Shuang Deng, Richland, WA (US); Kenneth S. Bruno, Richland, WA (US); David E. Culley, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 191 days.

(21) Appl. No.: 14/540,818

(22) Filed: Nov. 13, 2014

(65) Prior Publication Data

US 2016/0138031 A1     May 19, 2016

(51) Int. Cl.
| | |
|---|---|
| *C12P 21/06* | (2006.01) |
| *C12N 1/19* | (2006.01) |
| *C12N 15/81* | (2006.01) |
| *C12P 7/64* | (2006.01) |
| *C12Q 1/04* | (2006.01) |

(52) U.S. Cl.
CPC ............. *C12N 15/815* (2013.01); *C12P 7/64* (2013.01); *C12Q 1/04* (2013.01)

(58) Field of Classification Search
CPC ............. C12N 15/815; C12P 7/04; C12Q 1/04
See application file for complete search history.

(56) References Cited

U.S. PATENT DOCUMENTS

| | | | |
|---|---|---|---|
| 6,255,115 B1 | 7/2001 | Beijersbergen et al. | |
| 2006/0206961 A1* | 9/2006 | Cirpus ................ | C12N 9/1029 800/281 |
| 2009/0142322 A1 | 6/2009 | Ye | |
| 2012/0255070 A1* | 10/2012 | Cho ................... | C12N 15/8205 800/294 |

FOREIGN PATENT DOCUMENTS

IN     3501/MUM2012     * 12/2012 ............. C12P 39/00

OTHER PUBLICATIONS

Gietz et al., "Studies on the Transformation of Intact Yeast Cells by the LiAc/SS-DNA/PEG Procedure," *Yeast* 11:355-360, 1995.
Soltani et al., *Agrobacterium*-Mediated Transformation of Non-Plant Organisms, in *Agrobacterium: From Biology to Biotechnology*, Tzfira and Citovsky (eds.), pp. 649-675, Springer, 2008.
(Continued)

*Primary Examiner* — Reza Ghafoorian
(74) *Attorney, Agent, or Firm* — Klarquist Sparkman, LLP

(57) ABSTRACT

This disclosure provides *Agrobacterium*-mediated transformation methods for the oil-producing (oleaginous) yeast *Lipomyces* sp., as well as yeast produced by the method. Such methods utilize *Agrobacterium* sp. cells that have a T-DNA binary plasmid, wherein the T-DNA binary plasmid comprises a first nucleic acid molecule encoding a first protein and a second nucleic acid molecule encoding a selective marker that permits growth of transformed *Lipomyces* sp. cells in selective culture media comprising an antibiotic.

25 Claims, 9 Drawing Sheets

(56) References Cited

OTHER PUBLICATIONS

Ando et al., "Establishment of *Agrobacterium tumefaciens*-Mediated Transformation of an Oleaginous Fungus, *Mortierella alpina* 1S-4, and Its Application for Eicosapentaenoic Acid Producer Breeding," *App Environ Microbiol.* 75:5529-5535, 2009.

Bundock et al., "Trans-Kingdom T-DNA Transfer from *Agrobacterium tumefaciens* to *Saccharomyces cerevisiae*," *EMBO J.* 14:3206-3214, 1995.

Bundock & Hooykaas, "Integration of *Agrobacterium tumefaciens* T-DNA in the *Saccharomyces cerevisiae* Genome by Illegitimate Recombination," *Proc Natl Acad Sci. USA* 93:15272-15275, 1996.

Liu et al., "Characterization of Glyceraldehyde-3-phosphate Dehydrogenase Gene RtGPD1 and Development of Genetic Transformation Method by Dominant Selection in Oleaginous Yeast *Rhodosporidium toruloides*," *Appl Microbiol Biotechnol.* 97:719-729, 2013.

Murai, "Review: Plant Binary Vectors of Ti Plasmid in *Agrobacterium tumefaciens* with a Broad Host-Range Replicon of pRK2, pRi, pSa or pVS1," *Am J Plant Sci.* 4:932-939, 2013.

Piers et al. "*Agrobacterium tumefaciens*-Mediated Transformation of Yeast," *Proc Natl Acad Sci. USA* 93:1613-1618, 1996.

Risseeuw et al., "Integration of an Insertion-Type Transferred DNA Vector from *Agrobacterium tumefaciens* into the *Saccharomyces cerevisiae* Genome by Gap Repair ," *Mol Cell Biol.* 16:5924-5932, 1996.

Tapia et al., Optimization of Lipid Production by the Oleaginous Yeast *Lipomyces starkeyi* by Random Mutagenesis Coupled to Cerulenin Screening , *AMB Express* 2:64, 2012.

De Groot et al., "*Agrobacterium tumefaciens*-Mediated Transformation of Filamentous Fungi," *Nature* 16:839-842, 1998.

Fullner and Nester, Temperature Affects the T-DNA Transfer Machinery of Agrobacterium tumefaciens, *J Bacteriol.* 178:1498-1504, 1996.

Gelvin, "Agrobacterium-Mediated Plant Transformation: the Biology behind the "Gene-Jockeying" Tool," *Microbiol Mol Biol Rev.* 67:16-37, 2003.

Lin et al., "Chapter 6—The Initial Steps in *Agrobacterium tumefaciens* Pathogenesis: Chemical Biology Of Host Recognition," in *Agrobacterium: From Biology to Biotechnology*, Tzfira and Citovsky (eds.), pp. 221-241, Springer New York, 2008.

Matthysse and McMahan, The Effect of the *Agrobacterium tumefaciens* attR Mutation on Attachment and Root Colonization Differs between Legumes and Other Dicots, *Appl Environ Microbiol.* 67:1070-1075, 2001.

Srinivasan and Gothandam, "Synergistic Action of D-Glucose and Acetosyringone on Agrobacterium Strains for Efficient Dunaliella Transformation," *PLoS One* 11:e0158322, 2016.

\* cited by examiner

FIG. 5A. Hygromycin B phosphotransferase (hph; pRS426-pTef1-hph)
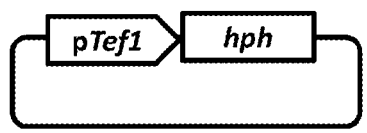
FIG. 5B. Hygromycin B phosphotransferase (hph; pZD663-pTef1-hph)
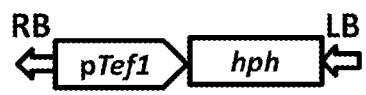
FIG. 5C. TrpC homologous deletion
FIG. 5D. Gus expression
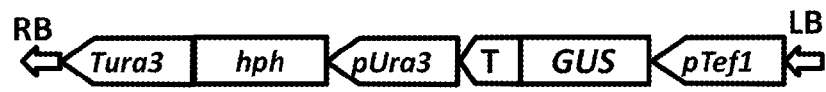
FIG. 5E. ME1 expression
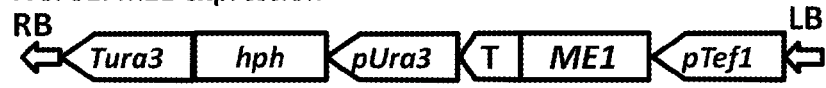

BstII λDNA
Mutant-1
Mutant-4
Mutant-5
Control (*L. starkeyi*)

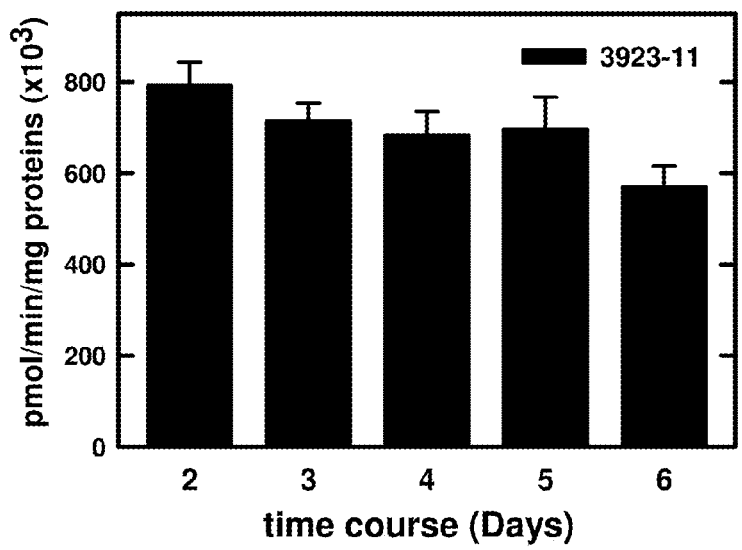
FIG. 9
FIG. 10
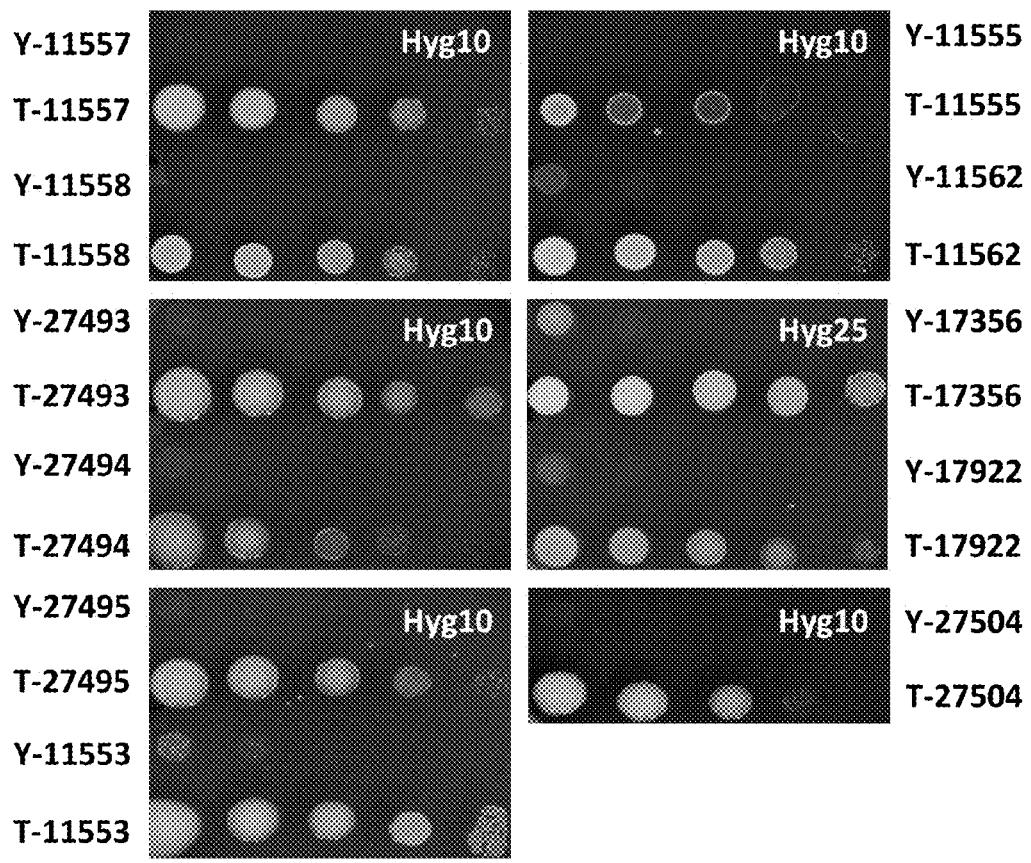

FIG. 11 A Hygromycin B phosphotransferase (hph; pZD663-pTef1-hph)

AGROBACTERIUM-MEDIATED TRANSFORMATION OF LIPOMYCES

ACKNOWLEDGMENT OF GOVERNMENT SUPPORT

This invention was made with government support under Contract DE-AC05-76RL01830 awarded by the U.S. Department of Energy. The government has certain rights in the invention.

FIELD

This disclosure provides *Agrobacterium*-mediated transformation methods for the oil-producing (oleaginous) yeast *Lipomyces* sp., as well as yeast produced by the method.

BACKGROUND

Concerns regarding fossil fuel supply and environmental impacts of their use have stimulated sustained interest in the development of sustainable renewable transportation fuels. Drop-in fuels can be obtained from the catalytic conversion of lipids or fatty acids from oilseed crops, oleaginous (oil-producing) algae or various microorganisms. The oil contents in the oleaginous microorganisms of bacteria, yeast, and filamentous fungi are usually more than 20% of the cells masses (Thevenieau & Nicaud, 2013). Some of microorganisms have been employed for commercial production of various nutrition oils, such as docosahexaenoic acid (DHA), eicosapentaneoic acid (EPA), gamma linolenic acid (GLA), and arachidonic acid (ARA), which demonstrates the feasibility of large-scale production of commercial oils (Sitepu et al, 2014b). The use of oleaginous fungi for lipid production has been studied in genera such as *Candida, Cryptococcus, Lipomyces, Mortierella, Rhodosporidium, Rhodotorula, Rhizpus, Trichosporon,* and *Yarrowia* (Beopoulos et al, 2009; Boulton & Ratledge, 1984; Gill et al, 1977; Rattray et al, 1975; Sitepu et al, 2014a; Starkey, 1946; Streekstra, 1997). The oleaginous yeast is appealing in regard to their use of lignocellulose derived sugars for conversion to lipids and other chemicals. In particular, Lipomycetaceae family such as, *Lipomyces doorenjongii, Lipomyces kononenkoae, Lipomyces lipofer, Lipomyces smithiae, Lipomyces suomiensis, Lipomyces starkeyi* and *Lipomyces tetrasporus* can accumulate lipid at up to 70% of its dry weight (Cullimore & Woodbine, 1961; Oguri et al, 2012; Starkey, 1946; Van Rensburg et al, 1995). They can utilize a variety of monosaccharides and disaccharides found in lignocellulosic biomass. The genome sequence of *L. starkeyi* has been determined by the Department of Energy Joint Genome Institute.

SUMMARY

Although extensive studies have been conducted on *Lipomyces* species, an effective transformation method for integration of exogenous genetic materials into the chromosomes of *Lipomyces* species has not been identified. Without an effective transformation method, *Lipomyces* species cannot be manipulated for improved productivity or customized product profiles. Two studies suggested that the exogenous plasmid DNA could be transferred into the cells of *L. starkeyi* and *L. kononenkoae* by the lithium acetate-mediated transformation (Calvey et al, 2014; Wang et al, 2011). However, it is shown herein that the inventors were unable to transform these two strains with similar lithium acetate transformation protocols. In addition, the inventors tried PEG-mediated protoplast and electroporation transformation protocols for three strains of *L. starkeyi* and *L. kononenkoae* and no transformed clones were obtained.

Because of these failures, the inventors developed an *Agrobacterium*-mediated method of transformation for *Lipomyces* sp. cells. Thus, the present disclosure provides *Agrobacterium*-mediated methods that can be used to transform *Lipomyces* sp. cells, for example to allow the cells to express one or more exogenous proteins. Also provided are transformed *Lipomyces* sp. cells produced by such methods, which can include at least one exogenous nucleic acid molecule and express at least one exogenous protein. Products produced directly or indirectly from the exogenous protein(s) by the transformed *Lipomyces* sp. cells can be isolated from culture media and/or from transformed cells.

In one example, the method of transforming *Lipomyces* sp. cells includes incubating the *Lipomyces* sp. cells with *Agrobacterium* sp. cells, for example in or on an induction medium. The *Agrobacterium* sp. cells can include an exogenous Ti plasmid or T-DNA binary plasmid that includes a first nucleic acid molecule encoding a first protein and a second nucleic acid molecule encoding a selective marker that when expressed, permits growth of transformed *Lipomyces* sp. cells in selective culture media comprising an antibiotic (e.g., one or more of G418, hygromycin B, Zeocin™, pyrithiamine, phleomycin D1, basta, gentamicin, and N-glycosyl-polifungin). The selective marker can be matched to the antibiotic in the selective culture media; for example, expression of hygromycin B phosphotransferase (hph) in *Lipomyces* sp. cells permits growth of such cells in culture media containing hygromycin B. Expression of the first and second nucleic acid molecules can be driven by one promoter or two separate promoters. The exogenous plasmid in the *Agrobacterium* sp. cells can include additional nucleic acid molecules encoding additional products, if desired (such as to allow expression of at least two, at least 3, at least 4 or at least 5 different proteins, such as 2, 3, 4, 5, 6, 7, 8, 9, 10, or more, different proteins). In some examples, the *Agrobacterium* sp. cells include multiple exogenous plasmids (e.g., T-DNA binary plasmids), each containing at least one nucleic acid molecule expressing a desired protein and a nucleic acid molecule encoding a selective marker, wherein the exogenous plasmids (e.g., T-DNA binary plasmids) have different selection markers to allow transformed *Lipomyces* sp. cells containing all of the desired exogenous plasmids (e.g., T-DNA binary plasmids) to be identified by growth in or on selective culture media containing an appropriate plurality of antibiotics. The *Agrobacterium* sp. cells and the *Lipomyces* sp. cells are incubated under conditions that allow the first nucleic acid molecule and the second nucleic acid molecule to integrate into a chromosome of the *Lipomyces* sp. cells. For example the *Agrobacterium* sp. cells and the *Lipomyces* sp. cells can be incubated at room temperature (such as about 20° C. to 28° C.) for at least 14 hours (such as at least 18 hours, at least 20 hours, at least 24 hours, at least 30 hours, at least 35 hours, at least 40 hours, or at least 48 hours, such as for about 2 days). Following integration of the first nucleic acid molecule and the second nucleic acid into a chromosome, the resulting transformed *Lipomyces* sp. cells are incubated in or on selective culture media. The selective culture media can include the antibiotic (resistance to which is provided by the nucleic acid molecule encoding the selective marker) and optionally with an antibiotic that substantially prevents growth of the *Agrobacterium* cells.

In some examples, prior to incubating the *Lipomyces* sp. cells with *Agrobacterium* cells, the method also includes incubating the *Lipomyces* sp. cells in culture media for at least 20 hours (such as at least 24 hours, at least 30 hours, at least 36 hours, or at least 48 hours) at least 20° C. (such as 20 to 35° C., 25 to 35° C., 28 to 32° C., such as 30° C.), for example at 50 to 500 rpm, such as about 200 rpm, wherein the culture media permits exponential growth of the *Lipomyces* sp. cells after about 15 hours at 30° C. and bud-growth stage after about 24 hours at 30° C. This can help ensure the *Lipomyces* sp. cells are at an optimal growth stage prior to transfection.

Prior to introduction of the nucleic acid molecule(s) into the *Lipomyces* sp. cells, such as the one encoding a selective marker, growth of the *Lipomyces* sp. cells is significantly reduced or suppressed in the selective culture media containing the antibiotic(s). However, following integration of the nucleic acid molecule(s) into the chromosome(s), such as the one encoding a selective marker, the *Lipomyces* sp. cells can grow and divide in the selective culture media containing the antibiotic(s). Thus, prior to introduction of the selective marker nucleic acid molecule(s) into the chromosome(s), growth of the *Lipomyces* sp. cells in the selective media can be significantly reduced, such as a growth reduction of at least 80%, at least 85%, at least 90%, at least 95%, at least 98%, at least 99% or 100% as compared to growth following integration of the nucleic acid molecule(s) into the chromosome(s). Similarly, following introduction of the selective marker nucleic acid molecule(s) into the chromosome(s), growth of the *Lipomyces* sp. cells in the selective media can be significantly increased, such as a growth and/or division of at least 2-fold, at least 3-fold, at least 4-fold, at least 5-fold, at least 10-fold, at least 20-fold, at least 50-fold, at least 100-fold, at least 1000-fold, or at least 10000-fold as compared to growth prior to integration of the nucleic acid molecule(s) into the chromosome(s). In some examples, such a measurement is performed in or on yeast synthetic complete (SC) or yeast extract-peptone-dextrose (YPD) medium at 30° C. for at least 60 hours, such as at least 70 hours, at least 80 hours, at least 90 hours, at least 100 hours, at least 120 hours, for example 70 to 200 hours, 70 to 150 hours, or 72 to 144 hours.

In some examples, the disclosed methods for transforming *Lipomyces* sp. cells allows the *Lipomyces* sp. cells to express one or more desired proteins, such as one or more exogenous proteins, such expression of at least two, at least 3, at least 4, at least 5, at least 10, at least 12, at least 15, or at least 20 different proteins, such as 2, 3, 4, 5, 6, 7, 8, 9, 10, or more different proteins. In some examples, the nucleic acid molecule(s) introduced into the *Lipomyces* sp. cells includes one or more nucleic acid molecules involved in saturated and/or unsaturated fatty acid synthesis or degradation, such as one or more of (such as at least 2, at least 3, at least 4, or at least 5 of): NADP-malic enzyme (me1), acyl coA synthase, acetyl-coA carboxylase (Acc1), acetyl coA ACP transferase, ACP-S-malonytransferase, fatty acid synthase (FAS1 & FAS2), glycerol-3 1-O-phosphate acyltransferase, diacylglycerol acyltransferase (DGA), DAG acyl transferase (DGAT), phospholipid:DAG acyltransferase (PDAT), acyl carrier protein (ACP), fatty acid acyl-CoA reductase (FAR), farnesyl diphosphate synthase, $\Delta 5$ desaturase, $\Delta 6$ desaturase, $\Delta 9$ desaturase, $\Delta 12$ desaturase, $\Delta 15$ desaturase, $\Delta 17$ desaturase, $\omega 3$ desaturase, fatty acid transporter (PZA1, PXA2), acetyl-CoA oxidase (PDX1, PDX2, PDX3), integral peroxisomal membrane protein (PEX10), and the like. The *Lipomyces* strains can also be engineered for lubricant/detergent production such as, alpha-olefins, which can be produced by expression of cytochrome P450 from *Rhodotorula minuta* or $H_2O_2$ independent cytochrome P450 OleT$_{JE}$ fatty acid decarboxylase from *Jeotgalicoccus* sp. in the *Lipomyces* sp. cells using the disclosed methods. The polyketide biosynthesis pathway s in *L. starkeyi* can be improved by introduction of one or more of (such as at least 2, at least 3, at least 4, or at least 5 of): Zn2-Cys6 binuclear cluster domain family, a global regulator of secondary metabolism (laeA), CoA-ligase (CL), acyltransferase (AT), ketosynthase (KS), ketoreductase (KR), enoly reductase (ER), and dehydrase (DH). *Lipomyces* sp. cells can be engineered using the disclosed methods for non-ribosomal peptide biosynthesis by introduction of one or more of the following nucleic acid molecules (such as at least 2, at least 3, at least 4, or at least 5 of): type I thioesterases (TEIs), type II thioesterases (TEIs), pipecolate-incorporating enzymes (PIEs), peptidyl carrier proteins (PCPs), methyltransferases (MTs), and 4'-phosphoantetheinyl transferases (PPTs). Such sequences are publicly available, for example from the GenBank® database and from the Joint Genome Institute (JGI) database (genome.jgi.doe.gov).

Thus, the disclosure also provides methods of producing a product. Such methods can include culturing transformed *Lipomyces* sp. cells produced using the disclosed transformation methods, in or on selective culture media that permits expression of one or more nucleic acid molecules producing one or more proteins (which may be the product of interest or may be part of a pathway that produces a product of interest) and the selective marker nucleic acid molecule, thereby producing the product directly or indirectly from the nucleic acid molecule. Such methods can further include isolating the product from the selective culture media or from the cells.

Examples of *Lipomyces* sp. cells that can be transformed with the disclosed methods include, but are not limited to: *L. starkeyi, L. doorenjongii, L. knockii, L. knononenkoae, L. lipofer, L. mesembrius,* and *L. tetrasporus* cells, such as *L. doorenjongii* strain NRRL Y-27504, *L. kononenoae* strain NRRL Y-11553, *L. lipofer* strain NRRL Y-11555, *L. smithiae* strain NRRL Y-17922, *L. suomiensis* strain NRRL Y-17356, *L. tetrasporus* strain NRRL Y-11562 cells, or one of *L. starkeyi* strains NRRL Y-11557, NRRL Y-11558, NRRL Y-27943, NRRL Y-27944, and NRRL Y-27945.

Examples of *Agrobacterium* sp. cells that can be used in the disclosed methods include but are not limited to *Agrobacterium tumefaciens* cells, such as *Agrobacterium tumefaciens* strains LBA1100, LBA1126, LBA4404, EHA105 and A348.

The foregoing and other objects and features of the disclosure will become more apparent from the following detailed description, which proceeds with reference to the accompanying figures.

BRIEF DESCRIPTION OF THE DRAWINGS

FIGS. 5A-5E are schematic drawings showing transgene expression constructs for lithium acetate, PEG-mediated protoplast, electroporation, and *Agrobacterium*-mediated transformation. In the pRS426-pTef1-hph construct (A), the coding region of bacterial hygromycin B phosphotransferase (hph) gene was under the control of *L. starkeyi* translation elongation factor α1 (tef1) gene promoter. In the pZD663-pTef1-hph construct (B), the pTef1-hph transgene cassette was excised from construct (A) with restriction enzyme PmeI and cloned into the T-DNA binary vector pZD663 at PmeI site. For the transgene expression construct (C), the 1-kb PCR DNA fragments of 5'-upstream and 3'-downstream of TrpC and pTef1-hph transgene cassette excised from construct (A) with restriction enzyme PmeI were fused together into yeast plasmid vector pRS426 by yeast gap repairing. Subsequently, the 3.7 kb plasmid DNA fragment containing the pTef1-hph flanked with the TrpC DNA fragments of 5' and 3' regions were cloned into the T-DNA binary vector pZD663 at SacI/XbaI sites. In the transgene expression construct (D), both transgene expression cassettes of hph under the control of *L. starkeyi* ura3 promoter and its terminator and GUS reporter gene under the control of *L. starkeyi* Tef1 promoter and its terminator were also prepared by yeast gap repairing separately. The 3 kb pUra3-hph-Tura3 DNA fragment was cloned into pZD663 at Pme I site to form pZD663hph, which was further used for subsequent addition of 3.4 kb pTef1-GUS-Ttef1 DNA fragment at the Hpa I site. The transgene expression construct (E) was built with the similar procedure, where coding and transcriptional terminator regions of NADP-ME1 gene under the control of Tef1 promoter was also inserted at Hpa I site. RB is the right border of the T-DNA binary plasmid, and LB is the left border of the T-DNA binary plasmid.

FIG. 9 is a bar graph showing the time-course of *Lipomyces starkeyi* tef1 promoter activity measured by GUS activity. The selected transgenic strain (clone 3923-11) was grown in liquid culture of lipid production medium at 30° C. and 200 rpm for 6 days.

FIG. 10 is a digital image comparing of parent and pTef1-hph transgenic strains grown on YPD medium agar plates with proper hygromycin B concentration in 1/10 series cell dilution. Hyp10 or Hyg25 is the YPD agar plate containing either 10 or 25 mg/l of hygromycyin B. The strain number shown on the figure corresponds to the following *Lipomyces* species: NRRL Y-11557; NRRL Y-11558; NRRL Y-27493; NRRL Y-27494; and NRRL Y-27495 for *L. starkeyi*; NRRL Y-11553 for *L. kononenkoae*; NRRL Y-27504 for *L. doorenjongii*; NRRL Y-11555 for *L. lipofer*; NRRL Y-17922 for *L. smithiae*; NRRL Y17356 for *L. suomiensis*; and NRRL Y-11562 for *L. tetrasporus*.

SEQUENCE LISTING

Figure 1A:
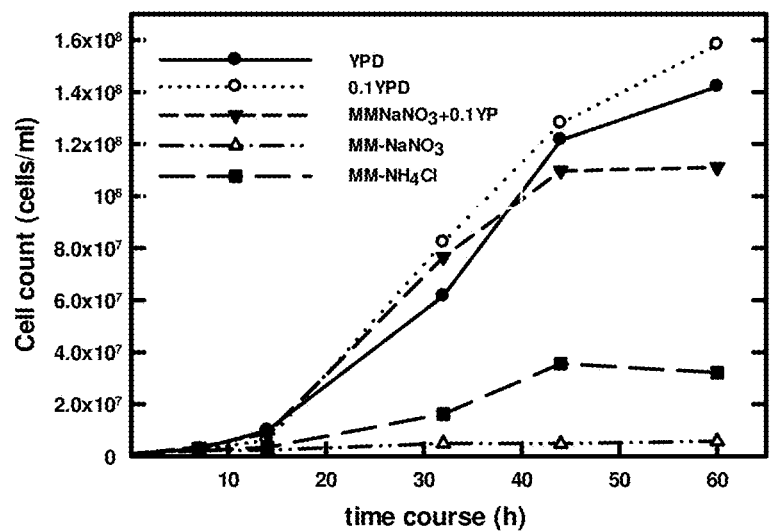
FIG. 1A is a graph showing a time-course of *Lipomyces starkeyi* strain NRRL Y-11557 growth in different liquid culture media at 30° C. and 200 rpm.

The nucleic acid sequences are shown using standard letter abbreviations for nucleotide bases, as defined in 37 C.F.R. 1.822. Only one strand of each nucleic acid sequence is shown, but the complementary strand is understood as included by any reference to the displayed strand.

SEQ ID NOS: 1-4 are oligonucleotides used to generate the Tef1-hph construct with yeast gap repairing (see FIG. 5A).

SEQ ID NOS: 5-10 are oligonucleotides used to generate the construct trpC upstream-tef1-hph-trpC downstream (see FIG. 5B).

SEQ ID NOS: 11-18 are oligonucleotides used to generate the Ura3-hph-ura3 binary vector construct (see left side portion of FIG. 5D).

SEQ ID NOS: 19-24 are oligonucleotides used for the Tef1-gus construct (see right side portion of FIG. 5D).

SEQ ID NOS: 25-28 are oligonucleotides used to generate Tef1-ME1 (see FIG. 5E).

SEQ ID NOS: 29-30 are oligonucleotides used for transgene expression confirmation.

SEQ ID NO: 31 is an exemplary tef1 promoter sequence from *L. starkeyi*.

SEQ ID NO: 32 is an exemplary ura3 promoter sequence from *L. starkeyi*.

SEQ ID NO: 33 is an exemplary pyrG promoter sequence from *L. starkeyi*.

SEQ ID NO: 34 is an exemplary elongation factor 2 (elf2) promoter sequence from *L. starkeyi*.

SEQ ID NO: 35 is an exemplary actin (act1) promoter sequence from *L. starkeyi*.

SEQ ID NO: 36 is an exemplary histone H4 promoter sequence from *L. starkeyi*.

SEQ ID NO: 37 is an exemplary ubiquitin fusion protein S27a promoter sequence from *L. starkeyi*.

SEQ ID NO: 38 is an exemplary ubiL40 promoter sequence from *L. starkeyi*.

SEQ ID NO: 39 is an exemplary 6-phosphogluconate dehydrogenase promoter sequence from *L. starkeyi*.

SEQ ID NO: 40 is an exemplary AAA+-type A ATPase promoter sequence from *L. starkeyi*.

SEQ ID NO: 41 is an exemplary transaldolase AB promoter sequence from *L. starkeyi*.

SEQ ID NO: 42 is an exemplary 60S ribosomal protein L10A promoter sequence from *L. starkeyi*.

SEQ ID NO: 43 is an exemplary S-adenosylmethionine synthase promoter sequence from *L. starkeyi*.

SEQ ID NO: 44 is an exemplary heat-shock protein (chaperone HSP104) promoter sequence from *L. starkeyi*.

SEQ ID NO: 45 is an exemplary heat shock protein HSP90 promoter sequence from *L. starkeyi*.

SEQ ID NO: 46 is an exemplary plasma-membrane proton-efflux P-type ATPase promoter sequence from *L. starkeyi*.

SEQ ID NO: 47 is an exemplary vacuolar H-ATP V1 sector, subunit A promoter sequence from *L. starkeyi*.

DETAILED DESCRIPTION

Unless otherwise noted, technical terms are used according to conventional usage. Definitions of common terms in molecular biology can be found in Benjamin Lewin, Genes VII, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. As used herein, the term "comprises" means "includes." Thus, "comprising a nucleic acid molecule" means "including a nucleic acid molecule" without excluding other elements. It is further to be understood that any and all base sizes given for nucleic acids are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. All references, including patent applications and patents, and sequences associated with the GenBank® Accession Numbers and the JGI Accession Numbers listed (as of Nov. 13, 2014) are herein incorporated by reference.

In order to facilitate review of the various embodiments of the disclosure, the following explanations of specific terms are provided:

*Agrobacterium*: A genus of Gram-negative bacteria that can be used to transfer genes into plants, and methods are provided herein for its use to transfer genes into *Lipomyces* sp. cells. A specific example is *Agrobacterium tumefaciens*, which causes crown-gall disease in plants. Exemplary strains include but are not limited to: *Agrobacterium tumefaciens* strains LBA1100, LBA1126, LBA4404, EHA105 and A348. Such bacteria are commercially available, for example from Clontech (LBA4404), ATCC (ATCC51317, A348), or from other sources, such as strains LBA1100 and LBA1126 from Dr. Paul Bundock (University of Leiden, The Netherlands), and EHA105 from Dr. Eugene Nester from University of Washington (Seattle, Wash.).

Antibiotic: An agent that can reduce or even prevent the growth of a microorganism, such as a yeast or bacterium (such as an *Agrobacterium*). Examples include, but are not limited to: G418 (Geneticin®), hygromycin B, pyrithiamine, phleomycin D1 (Zeocin™), blasticidin, basta (glufosinate ammonium), cefotaxime, gentamicin, N-glycosyl-polifungin, acetamide, cycloheximide, kanamycin, nouriseothricin, or combinations thereof. Antibiotic sensitivity (or susceptibility) tests can be performed to identify an antibiotic that a particular microorganism is sensitive to, that is, an antibiotic in which the microorganism grows poorly in (or not at all). In some examples, antibiotic sensitivity (or susceptibility) can be reversed by expression of a selectable marker by the microorganism. For example, *Lipomyces* sp. cells are sensitive to hygromycin B, but expression of hygromycin B phosphotransferase (hph) by the *Lipomyces* sp. cells permits growth of such cells in culture media containing hygromycin B.

Contact: To bring one agent into close proximity to another agent, thereby permitting the agents to interact. For example, a microorganism, such as a yeast or bacterium, can be contacted in or on a culture media, thereby permitting growth of the microorganism in or on the media. Similarly, a *Lipomyces* sp. cell to be transformed with a plasmid can be incubated in a culture media with an *Agrobacterium* containing plasmid of interest under appropriate conditions, thereby permitting migration of the plasmid T-DNA region fragments into the *Lipomyces* sp. cell.

Culture or growth media: A liquid or solid (such as agar) that permits and supports the growth of microorganisms, such as yeast or bacteria. Includes nutrient broths that contain components necessary for yeast growth and replication, such as water, a carbon source (such as glucose), and salts. Such media can include other agents, such as vitamins and amino acids. Specific examples include, but are not limited to, synthetic complete (SC) and yeast extract-peptone-dextrose (YPD) media. Selective culture media is used to permit only growth of selected organisms, such as yeast or bacteria transformed with a desired nucleic acid molecule, which is expressed by the organism. For example, if a microorganism is resistant to a certain antibiotic (referred to in the art as a selection antibiotic), such as hygromycin B or geneticin, then that antibiotic can be added to the medium in order to prevent other cells, which do not possess the resistance, from growing. Such resistance can be achieved by the expression of a selective marker nucleic acid molecule specific for the antibiotic. For example, expression of hygromycin B phosphotransferase (hph) can be used to achieve growth in hygromycin B containing media for an organism that is otherwise sensitive to the antibiotic. Resistance to Zeocin™ antibiotic is conferred by the product of the Sh ble gene. Resistance to blasticidin is conferred by the product of the bsd gene from *Aspergillus terreus*. Resistance to G418 is conferred by the neo gene from Tn5 encoding an aminoglycoside 3'-phosphotransferase, APT 3' II. Resistance to acetaminde is conferred by the *Aspergillus nidulans* amdS gene. Resistance to cycloheximde is conferred by ribosomal protein L41 gene. Resistance to basticidin is conferred by the blasticidin S deaminase gene from *Bacillus cereus*. Resistance to nourseothricin is conferred by the nourseothricin acetyltransferase.

Exogenous: The term "exogenous" as used herein with reference to nucleic acid molecule and a particular cell refers to any nucleic acid molecule that does not originate from that particular cell as found in nature. Thus, a non-naturally-occurring nucleic acid molecule is considered to be exogenous to a cell once introduced into the cell. A nucleic acid molecule that is naturally-occurring also can be exogenous to a particular cell. For example, an entire chromosome isolated from cell X is an exogenous nucleic acid with respect to cell Y once that chromosome is introduced into cell Y.

Expression or gene expression: A multi-step process involving converting genetic information encoded in a genome and intervening nucleic acid sequences (e.g., mRNA) into a polypeptide. The genomic sequence of a gene is "transcribed" to produce RNA (e.g., mRNA, also referred to as a transcript). The mRNA is "translated" to produce a corresponding protein. Gene expression can be regulated at many stages in the process. In some examples, transcription of a gene is facilitated by a promoter.

Incubate or culture: Cells, such as bacterial or yeast cells, grown or maintained under controlled conditions, for example in a laboratory. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Isolated: An "isolated" or "purified" biological component or organism (such as a nucleic acid molecule, protein, bacterium or yeast) has been substantially separated, produced apart from, or purified away from other biological components in the cell of the organism in which the component naturally occurs, that is, other chromosomal and extrachromosomal DNA and RNA, and proteins, or has been substantially separated, produced apart from, or purified away from other organisms. Nucleic acids and proteins that have been "isolated" or "purified" thus include nucleic acids and proteins purified by standard purification methods. Similarly, cells (such as microorganisms) that have been "isolated" or "purified" include cells purified by standard purification methods (such as centrifugation to remove culture media, or culturing in a selective media to permit selective growth by a desired microorganism). The term also embraces nucleic acids and proteins prepared by recombinant expression in a host cell, as well as chemically synthesized nucleic acids or proteins. The term "isolated" or "purified" does not require absolute purity; rather, it is intended as a relative term. Thus, for example, an isolated biological component is one in which the biological component is more enriched than the biological component is in its natural environment within a cell, or other production vessel. In one example, a preparation is purified such that the biological component represents at least 50%, such as at least 70%, at least 90%, at least 95%, or greater, of the total biological component content of the preparation.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Promoter: An array of nucleic acid control sequences which direct transcription of a nucleic acid. A promoter includes necessary nucleic acid sequences near the start site of transcription. A promoter also optionally includes distal enhancer or repressor elements. A "constitutive promoter" is a promoter that is continuously active and is not subject to regulation by external signals or molecules. In contrast, the activity of an "inducible promoter" is regulated by an external signal or molecule (for example, a transcription factor). In some embodiments herein, the promoter is suitable for expression in yeast cells.

Exemplary promoters that can used in the methods provided herein include, but are not limited to: tef1: jgi|Lipst1_1|63951; heat shock protein Hsp90: jgi|Lipst1_1|6737; TrpC (indole-3-glycerol-phosphate synthase: jgi|Lipst1_1|238934; ura3: jgi|Lipst1_1|299000; ME1 (malic enzyme): jgi|Lipst1_1|72728; ACCT (acetyl-CoA carboxylase): jgi|Lipst1_1|72701; GND2 (6-phosphogluconate dehydrogenase): jgi|Lipst1_1|1792; CDC48 (AAA+-type ATPase): jgi|Lipst1_1|67128; Eft2 (elongation factor 2): jgi|Lipst1_1|107978; act1 (actin): jgi|Lipst1_1|67392/jgi|Lipst1_1|158360; RPL40A (ubiquitin-ribosomal 60S subunit protein L40A fusion protein): jgi|Lipst1_1|33975; PMA1 (Pasma membrane $H^+$-ATPase): jgi|Lipst1_1|97795; TAL1 (transaldolase): jgi|Lipst1_1|69361; HHF (Histone H4 protein): jgi|Lipst1_1|72700; ubi4 (polyubiquitin): jgi|Lipst1_1|31121; RPL1B (ribosomal protein L10A): jgi|Lipst1_1|72371; and SAM2 (S-adenosylmethionine synthase): jgi|Lipst1_1|328593]. Specific exemplary promoter sequences are provided in SEQ ID NOS: 31-47.

In particular non-limiting examples, the promoter is the translational elongation factor 1α (tef1a) promoter, such as one from *Lipomyces* sp., such as *L. starkeyi* (e.g., see SEQ ID NO: 31). In particular non-limiting examples, the promoter is the ura3 promoter, such as one from *Lipomyces* sp., such as *L. starkeyi* (e.g., see SEQ ID NO: 32).

Recombinant: A recombinant nucleic acid is one that has a sequence that is not naturally occurring and/or has a sequence that is made by an artificial combination of two otherwise separated segments of sequence. This artificial combination can be accomplished by chemical synthesis or by the artificial manipulation of isolated segments of nucleic acids, e.g., by genetic engineering techniques. Recombinant is also used to describe nucleic acid molecules that have been artificially manipulated, but contain the same regulatory sequences and coding regions that are found in the organism from which the nucleic acid was isolated. A recombinant microorganism is one containing a recombinant nucleic acid molecule(s).

Selectable marker: A gene introduced into a cell, such as a yeast or bacterial in culture, that confers a trait (e.g., antibiotic resistance) suitable for artificial selection from yeast or bacterial that do not possess the gene.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith and Waterman (*Adv. Appl. Math.*, 2:482, 1981); Needleman and Wunsch (*J. Mol. Biol.*, 48:443, 1970); Pearson and Lipman (*Proc. Natl. Acad. Sci.*, 85:2444, 1988); Higgins and Sharp (*Gene*, 73:237-44, 1988); Higgins and Sharp (*CABIOS*, 5:151-53, 1989); Corpet et al. (*Nuc. Acids Res.*, 16:10881-90, 1988); Huang et al. (*Comp. Appls. Biosci.*, 8:155-65, 1992); and Pearson et al. (*Meth. Mol. Biol.*, 24:307-31, 1994). Altschul et al. (*Nature Genet.*, 6:119-29, 1994) presents a detailed consideration of sequence alignment methods and homology calculations.

The alignment tools ALIGN (Myers and Miller, *CABIOS* 4:11-17, 1989) or LFASTA (Pearson and Lipman, *Proc. Natl. Acad. Sci.* 85:2444-2448, 1988) may be used to perform sequence comparisons (Internet Program© 1996, W. R. Pearson and the University of Virginia, "fasta20u63" version 2.0u63, release date December 1996). ALIGN compares entire sequences against one another, while LFASTA compares regions of local similarity. These alignment tools and their respective tutorials are available on the Internet at the NCSA website. Alternatively, for comparisons of amino acid sequences of greater than about 30 amino acids, the "Blast 2 sequences" function can be employed using the default BLOSUM62 matrix set to default parameters, (gap existence cost of 11, and a per residue gap cost of 1). When aligning short peptides (fewer than around 30 amino acids), the alignment can be performed using the "Blast 2 sequences" function, employing the PAM30 matrix set to default parameters (open gap 9, extension gap 1 penalties). The BLAST sequence comparison system is available, for instance, from the NCBI web site; see also Altschul et al., *J. Mol. Biol.*, 215:403-10, 1990; Gish and States, *Nature Genet.*, 3:266-72, 1993; Madden et al., *Meth. Enzymol.*, 266:131-41, 1996; Altschul et al., *Nucleic Acids Res.*, 25:3389-402, 1997; and Zhang and Madden, *Genome Res.*, 7:649-56, 1997.

Orthologs (equivalent to proteins of other species) of proteins provided herein are in some instances characterized by possession of greater than 75% sequence identity counted over the full-length alignment with the amino acid sequence of specific protein using ALIGN set to default parameters. Proteins with even greater similarity to a reference sequence will show increasing percentage identities when assessed by this method, such as at least 80%, at least 85%, at least 90%, at least 92%, at least 95%, at least 98%, or at least 99% sequence identity. In addition, sequence identity can be compared over the full length of the disclosed proteins. Thus, in some examples, proteins disclosed herein by their GenBank® or JGI Accession No., which can be used in the disclosed methods, can have at least 80%, at least 85%, at least 90%, at least 92%, at least 95%, at least 98%, or at least 99% sequence identity to those in the recited GenBank® or JGI Accession No.

When significantly less than the entire sequence is being compared for sequence identity, homologous sequences will typically possess at least 80% sequence identity over short windows of 10-20, and may possess sequence identities of at least 85%, at least 90%, at least 95%, 96%, 97%, 98%, or at least 99% depending on their similarity to the reference sequence. Sequence identity over such short windows can be determined using LFASTA; methods are described at the NCBI website. One of skill in the art will appreciate that these sequence identity ranges are provided for guidance only; it is entirely possible that strongly significant homologs could be obtained that fall outside of the ranges provided. Similar homology concepts apply for nucleic acids as are described for protein. An alternative indication that two nucleic acid molecules are closely related is that the two molecules hybridize to each other under stringent conditions.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that each encode substantially the same protein. Thus, in some examples, nucleic acid sequences, such as promoters, disclosed herein by their GenBank® or JGI Accession No., which can be used in the disclosed methods, can have at least 80%, at least 85%, at least 90%, at least 92%, at least 95%, at least 98%, or at least 99% sequence identity to those in the recited GenBank® or JGI Accession No. (e.g., any of the promoter sequences shown in any of SEQ ID NOS: 31-47).

Transformed: A "transformed" cell is a cell (such as a yeast cell or bacterial cell, for example a *Lipomyces* sp. or an *Agrobacterium* sp. cell, respectively) into which has been introduced a nucleic acid molecule, for example by molecular biology techniques. The term encompasses all techniques by which a nucleic acid molecule might be introduced into such a cell, including transfection with viral vectors, transformation with plasmid vectors (such as a T-DNA binary plasmid), and introduction of naked DNA by electroporation, lipofection, particle gun acceleration. A specific example of transformation is *Agrobacterium*-mediated transformation which utilizes a T-DNA binary plasmid to introduce genetic material from the *Agrobacterium* into a cell, such as a *Lipomyces* cell.

Vector: A nucleic acid molecule allowing insertion of foreign nucleic acid without disrupting the ability of the vector to replicate and/or integrate in a host cell, such as a bacterial or yeast cell. A vector can include nucleic acid sequences that permit it to replicate in a host cell, such as an origin of replication. An insertional vector is capable of inserting itself into a host nucleic acid. A vector can also include one or more selectable marker genes (such as an antibiotic selection marker) and other genetic elements. An expression vector is a vector that contains the necessary regulatory sequences to allow transcription and translation of inserted gene or genes. A specific type of vector is a plasmid, which is a circular nucleic acid molecule capable of autonomous replication in a host cell, such as a yeast cell or bacterial cell. Examples include the tumor inducing (Ti) plasmid from *A. tumefaciens* and the Ri plasmid from *A. rhizogenes*. The Ti plasmids are classified into different types based on the type of opine produced by their genes. The different opines specified by Ti plasmids are octopine, nopaline, succinamopine and leucinopine. Ti plasmids can be modified in their T-DNA region to remove the genes (e.g., auxin, cytokinin, and opine) that cause crown gall formation and replace them with one or more nucleic acid molecules, such as an antibiotic resistance marker (selection marker), which can be transferred into a *Lipomyces* sp. cell using the methods provided herein. Ti plasmids are also known as T-DNA binary plasmids, which include an antibiotic resistance gene (selection marker) for selection of transformants, and the T-DNA region that is transferred to the target genome, such as a *Lipomyces* sp. cell (for reviews see Lee and Gelvin, *Plant Phys.* 146:325-332, 2008 and Murai, *Am. J. Plant Sci.*, 4:932-9, 2013). The terms vector and plasmid are used interchangeably herein, as are Ti plasmid and T-DNA binary plasmid.

Yeast: Single-celled fungi that reproduce asexually. In the context of the present disclosure, any species or strain of *Lipomyces* sp. can be transformed with the disclosed methods. In some embodiments, the yeast is *L. arxii, L. starkeyi, L. doorenjongii, L. japonica, L. knockii, L. knononenkoae, L. lipofer, L. mesembrius, L. spencer-martinsiae, L. oligophaga, L. orientalis, L. smithiae, L. spencermartinsiae, L. starkeyi, L. suomiensis, L. tetrasporus, L. yamadae,* or *L. yarrowii,* such as *L. doorenjongii* strain NRRL Y-27504, *L. kononenoae* strain NRRL Y-11553, *L. lipofer* strain NRRL Y-11555, *L. smithiae* strain NRRL Y-17922, *L. suomiensis* strain NRRL Y-17356, or *L. tetrasporus* strain NRRL Y-11562. In particular examples, the yeast is *L. starkeyi*, such as strain NRRL (The North Regional Research Laboratory) Y-11557, NRRL Y-11558, NRRL Y-27943, NRRL Y-27944, or NRRL Y-27945. Other specific examples include but are not limited to: *L. arxii* strain NRRL Y-17921; *L. japonicas* strain NRRL Y-17848; *L. kockii* strain NRRL Y-2750; *L. lipofer* strain NRRL Y-1351 and NRRL Y-6333; *L. mesembrius* strain NRRL Y-27927, NRRL Y-27928, NRRL Y-27929, NRRL Y-27930, and NRRL Y-27931; *L. spencer-martinsiae* strain NRRL Y-7042; and *L. starkeyi* strain NRRL Y-27507.

Overview

Oleaginous microbes, such as microalgae, bacteria, yeast, and fungi, have been explored for their potential application in bio-hydrocarbon industries. It has been proposed that such organisms can be used to produce different types of bio-hydrocarbons (e.g., fuels and chemicals). These microbes can grow under extreme growth environments, utilize broad saccharides from lignocellulosic biomasses, and can have high productivity. These characteristics can be improved by genetically optimizing those properties. The oil-producing (oleaginous) yeast, such as *Lipomyces* starkeyi, can grow at extremely low pH, utilize various oligo- or mono-saccharides derived from lignocelluloses, and accumulate high level of lipids. Although its genome has been sequenced, there are no sound genetic tools for engineering the organism. Therefore, effective transformation methods are needed with suitable selectable markers (e.g., antibiotic resistance genes) and the necessary genetic elements (e.g., promoters and terminators) for transgene expression of the selected genes. Such methods can allow for the expression of targeted genes to improve lipid and chemical productivity by *Lipomyces* sp. cells.

Provided herein are *Agrobacterium*-mediated transformation methods for *Lipomyces* starkeyi and other *Lipomyces* species. It is shown that DNA can be integrated into the chromosomes of *L. starkeyi* and other *Lipomyces* species by *Agrobacterium tumefaciens*-mediated transformation. Bacterial hygromycin B phosphotransferase (hph) was used as an antibiotic selection marker gene for effective transformation selection, and the genes of the bacterial β-glucuronidase (GUS) reporter and *L. starkeyi* NADP-malic enzyme (ME1) gene under the control of *L. starkeyi* translation elongation factor 1α promoter were also successfully demonstrated. The results herein demonstrate that *Agrobacterium*-mediated transformation is can be used for introduction of exogenous genes into *L. starkeyi* and other *Lipomyces* species.

In contrast to other transformation methods, *A. tumefaciens* has the capability to transfer a particular fragment (T-DNA) of the tumor-inducing (Ti) plasmid into the nucleus of infected cells, which is stably integrated into the chromosome subsequently (Nester et al, 1984). Since *Agrobacterium*-mediated transformation of *Saccharomyces cerevisiae* was demonstrated in 1995, this technique has been applied to different fungal genera (e.g., Ascomycetes, Basidomycetes, Glomeromycota, Oomycetes, and Zygomycetes) (Bundock et al, 1995; Soltani et al, 2008), but not to *Lipomyces* species. With current transgene expression construction methods, such as Gibson assembly and yeast gap repairing, the transgene expression cassettes within the T-DNA region of the T-DNA binary vector can be effectively constructed in one or two steps (Gibson et al, 2009; Orr-Weaver & Szostak, 1983).

Methods of Transforming *Lipomyces* sp

In one example, the method of transforming *Lipomyces* sp. cells includes incubating the *Lipomyces* sp. cells with *Agrobacterium* sp. cells, for example in or on an induction medium. The induction media can include acetosyringone (e.g., 0.2 mM). Induction media allows growth of both *Agrobacterium* and fungal (e.g., yeast) cells at similar rates. Induction medium contains low amounts of nutrients and the carbon source to slow down cell division (e.g., modified minimal medium for yeast having one tenth the amount of glucose and one twelfth the amount of nitrogen source).

The *Agrobacterium* sp. cells used in the transformation include a Ti or T-DNA binary plasmid (e.g., one that includes the T-DNA region, but not virulence genes). For example, a disarmed Ti-plasmid such as pTiBo542 for EHA105 can be used, wherein genes within the T-DNA region are removed, but the virulence (vir) genes required for T-DNA processing are retained for transferring the T-DNA region of DNA fragments from the vectors mobilized into the *Agrobacterium*. Such Ti or T-DNA binary plasmids can replicate in *Agrobacterium tumefaciens* and can require a helper plasmid (e.g., one already present in *Agrobacterium*) for gene transfer from the T-DNA region.

In some examples, the *Agrobacterium* sp. cells include more than one T-DNA binary plasmid, such as at least 2 different plasmids (such as at least 2, at least 3, at least 4, at least 5, at least 6, at least 7, at least 8, at least 9, at least 10, such as 1, 2, 3, 4, 5, 6, 7, 8, 9, 10, 15, or 20 different T-DNA binary plasmids), which for example can include different nucleic acid molecules encoding different proteins. In some examples, each T-DNA binary plasmid includes at least one nucleic acid molecule expressing a desired protein and a nucleic acid molecule encoding a selective marker, wherein the T-DNA binary plasmids have different selection markers to allow transformed *Lipomyces* sp. cells containing all of the desired T-DNA binary plasmids to be identified by growth in or on selective culture media containing an appropriate plurality of antibiotics. For example, a first T-DNA binary plasmid can include a nucleic acid molecule encoding a first protein and a nucleic acid molecule encoding a first selective marker, while a second T-DNA binary plasmid can include a nucleic acid molecule encoding a second protein and a nucleic acid molecule encoding a second selective marker.

The Ti or T-DNA binary plasmid, includes a first nucleic acid molecule encoding a first protein and a second nucleic acid molecule encoding a selective marker. The T-DNA binary plasmid(s) in the *Agrobacterium* sp. cells can include additional nucleic acid molecules encoding additional products, if desired (such as to allow expression of at least two, at least 3, at least 4, at least 5, at least 6, at least 7, at least 8, at least 9, at least 10, such as 1, 2, 3, 4, 5, 6, 7, 8, 9, 10, 15, or 20 different proteins). That is, each T-DNA binary plasmid can express more than one protein, if desired. Expression of the selective marker (e.g., antibiotic resistance gene) by a microorganism permits growth of transformed microorganism (e.g., transformed *Lipomyces* sp. cells) in selective culture media that includes a corresponding antibiotic (e.g., one or more of G418, hygromycin B, Zeocin™, pyrithiamine, phleomycin D1, basta, gentamicin, and N-glycosyl-polifungin). The selective marker can be matched to the antibiotic in the selective culture media; for example, expression of hygromycin B phosphotransferase (hph) in *Lipomyces* sp. cells permits growth of such cells in culture media containing hygromycin B.

Expression of the nucleic acid molecules in the T-DNA binary plasmid can be driven by one or more promoters. In some examples, one promoter drives expression of multiple nucleic acid molecules. In some examples, each nucleic acid molecule is expressed from a different promoter. Combinations of these arrangements are also possible.

The *Agrobacterium* sp. cells and the *Lipomyces* sp. cells are incubated under conditions that allow the nucleic acid molecules encoding the desired protein(s) and the selective marker to be integrated into a chromosome of the *Lipomyces* sp. cells. Such integration allows for expression of the proteins encoded by the nucleic acid molecules, including the selective marker protein. For example the *Agrobacterium* sp. cells and the *Lipomyces* sp. cells can be incubated at room temperature (such as about 20° C. to 28° C., 25° C. to 28° C., or 23 to 28° C., such as 20, 21, 22, 23, 24, 25, 26, 27, or 28° C.) for at least 14 hours (such as at least 20 hours, at least 24 hours, at least 30 hours, at least 35 hours, at least 40 hours, or at least 48 hours, such as for about 2 days). In some examples, the *Agrobacterium* sp. cells and the *Lipomyces* sp. cells are applied to a solid support, such as a nitrocellulose, nylon membrane, or solid agar, which is applied to a solid culture media (e.g., agar plate containing media). Following integration of the nucleic acid molecules encoding the desired protein(s) and the selective marker into at least one chromosome, the resulting transformed *Lipomyces* sp. cells are incubated in or on selective culture media. The selective culture media can include the antibiotic (resistance to which is provided by the nucleic acid molecule encoding the selective marker) and optionally with an antibiotic that substantially reduces growth of the *Agrobacterium* cells (such as cefotaxime, carbenicillin or timentin). The transformed *Lipomyces* sp. cells can be grown in or on the selective culture media at a temperature at least 25° C. (such as 25 to 35° C., 28 to 32° C., such as 30° C.), for at least 2 days, such as at least 3 days, at least 4 days, at least 5 days, at least 6 days, at least 7 days, at least 8 days, at least 9 days, or at least 10 days, such as 2 to 6 or 3 to 6 days.

In some examples, prior to incubating the *Lipomyces* sp. cells with *Agrobacterium* cells (e.g., prior to the transformation), the method also includes incubating the *Lipomyces* sp. cells to be transformed in culture media for at least 24 hours (such as at least 30 hours, at least 36 hours, or at least 48 hours) at least 25° C. (such as 25 to 35° C., 28 to 32° C., such as 30° C.), for example at 50 to 500 rpm, such as 100 to 300 rpm, such as about 200 rpm. In some examples the culture media permits exponential growth of the *Lipomyces* sp. cells, for example after about 15 hours at 30° C. and bud-growth stage after about 24 hours at 30° C. Thus, in some examples the *Lipomyces* sp. cells to be transformed are at an exponential growth phase and/or a bud-growth stage (e.g., actively dividing). In some examples, the disclosed methods include the step of identifying a culture media for the transformed *Lipomyces* sp. cells that permit exponential growth and active division of the *Lipomyces* sp. cells (e.g., see Example 2). In some example, the culture media for the transformed *Lipomyces* sp. cells includes yeast-peptone-dextrose (YPD) or yeast synthetic complete (SC) medium.

Prior to introduction of the nucleic acid molecule encoding a selective marker into the *Lipomyces* sp. cells, growth of the *Lipomyces* sp. cells is significantly reduced or suppressed in the selective culture media containing the antibiotic(s). That is, the non-transformed *Lipomyces* sp. cells are sensitive to the antibiotic. However, following integration of the nucleic acid molecule encoding a selective marker into the chromosome(s) the *Lipomyces* sp. cells can grow and divide in the selective culture media containing the antibiotic(s). That is, the transformed *Lipomyces* sp. cells are resistant to the antibiotic. Thus, prior to introduction of the selective marker nucleic acid molecule(s) into the chromosome(s), growth of the *Lipomyces* sp. cells in the selective media can be significantly reduced, such as a growth reduction of at least 80%, at least 85%, at least 90%, at least 95%, at least 98%, at least 99% or 100% as compared to growth following integration of the nucleic acid molecule(s) into the chromosome(s). Similarly, following introduction of the selective marker nucleic acid molecule(s) into the chromosome(s), growth of the *Lipomyces* sp. cells in the selective media can be significantly increased, such as a growth and/or division of at least 2-fold, at least 3-fold, at least 4-fold, at least 5-fold, at least 10-fold, at least 20-fold, at least 50-fold, at least 100-fold, at least 500-fold, at least 1000-fold, at least 5000-fold, or at least 10,000-fold, as compared to growth prior to integration of the nucleic acid molecule(s) into the chromosome(s). In some examples, such measurements are performed in or on yeast synthetic complete (SC) or yeast extract-peptone-dextrose (YPD) medium at 30° C. for at least 60 hours, such as at least 70 hours, at least 80 hours, at least 90 hours, at least 100 hours, at least 120 hours, for example 70 to 200 hours, 70 to 150 hours, or 72 to 144 hours. In some examples, the disclosed methods include the step of identifying an antibiotic (and an appropriate concentration) to which the non-transformed *Lipomyces* sp. cells are sensitive to (e.g., result in growth suppression) (e.g., see Example 3).

Recombinant or transformed *Lipomyces* sp. cells generated using the disclosed transformation methods, which include (and express) the nucleic acid molecule encoding a desired protein(s) and the nucleic acid molecule encoding a selection marker, are provided. In some examples, such nucleic acid molecules are integrated into one or more chromosomes of the *Lipomyces* sp. cells. In some examples, multiple copies of the nucleic acid molecule encoding a desired protein(s) and the nucleic acid molecule encoding a selection marker are integrated, such as at least 1 copy, at least 2 copies, at least 3 copies, at least 4, copies, or at least 5 copies. Such transformed *Lipomyces* sp. cells can be used for protein and chemical production, such as production of therapeutic proteins (e.g., human serum albumin, antibodies, immunotoxins, antigens for vaccination, human apolipoprotein A-I), industrial enzymes (e.g., cellulases, lipases, alpha amylases, and glucoamylase), polyunsaturated fatty acids [e.g., arachidonic acid (AA), eicosapentaenoic acid (EPA), docosahexaenoic acid (DHA)], secondary metabolites (e.g., phenolics, isoprenoids, alkaloids, and polykides), and other chemicals (e.g., alpha-olefin).

Antibiotic Selection Markers

A nucleic acid molecule encoding for a selective marker, such as an antibiotic resistance gene, can be included in the T-DNA binary plasmid that is present in the *Agrobacterium* sp. Such molecules are well known in the art. As discussed herein, the selection marker expressed is matched to the antibiotic in the culture media in which the transformed

*Lipomyces* sp. cells are grown. Specific exemplary combinations are provided below. One skilled in the art will appreciate that a nucleic acid molecule that is exogenous to *Lipomyces* sp., such as one of bacterial origin, can be codon optimized for expression in *Lipomyces* sp.

TABLE 1

Exemplary antibiotics and resistance genes

| Antibiotic | Resistance Gene | Exemplary GenBank® Accession Nos. |
|---|---|---|
| hygromycin B | hygromycin B phosphotransferase (hph) | DD223538.1; NC_020087.1; X03615.1; Z32698.1 |
| G418 | neomycin resistance gene (neo) from Tn5 encoding an aminoglycoside 3'-phosphotransferase, APH 3' II | pBI121 (AF485783.1) and plasmid pMOD2-Neo |
| pyrithiamine | *Aspergillus oryzae* thiazole synthase (pyrithiamine-resistance gene (ptrA) | AF217503.1 |
| phleomycin D1 | Phleomycin binding protein | pAN8-1 (Z32751.1) |
| basta | Phosphinothricin acetyltransferase (pat, bar) | Q57146 |
| gentamicin | Minoglycoside modifying enzyme | AF016483.1; U51479.1 |

In one example, the hph nucleic acid molecule used to confer hygromycin B antibiotic resistance to *Lipomyces* sp. cells is one from *Streptomyces hygroscopicus*, *E. coli*, or *Klebsiella pneumoniae*.

Exemplary Nucleic Acids

The disclosure herein of methods to transform *Lipomyces* sp. cells, allows for the expression of one or more nucleic acid molecules in the cells that encode a desired protein(s), in addition to the nucleic acid molecule encoding the selective marker. These nucleic acid molecules can be endogenous (e.g., from the same species and strain of *Lipomyces* but transformed into the *Lipomyces* sp. cells, for example to increase expression of such nucleic acid molecules) or exogenous (e.g., from a different species of *Lipomyces* or from a different organism) genes to *Lipomyces* sp. One skilled in the art will appreciate that a nucleic acid molecule that is exogenous to *Lipomyces* sp., such as one of bacterial origin, can be codon optimized for expression in *Lipomyces* sp.

In one example, the *Lipomyces* sp. cells express at least 2, at least 3, at least 4, at least 5, at least 6, at least 7, at least 8, at least 9, at least 10, at least 12, at least 15 or at least 20 different nucleic acid molecules, such as 2, 3, 4, 5, 6, 7, 8, 9, 10, 11, 12, 13, 14, 15, 16, 17, 18, 19, or 20 different nucleic acid molecules. Such nucleic acid molecules can be expressed from a single T-DNA binary plasmid, or from a plurality of T-DNA binary plasmids (such as at least 2, at least 3, at least 4, at least 5, at least 6, at least 7, at least 8, at least 9, or at least 10, different T-DNA binary plasmids, such as 2, 3, 4, 5, 6, 7, 8, 9, 10, 11, 12, 13, 14, 15, 16, 17, 18, 19, or 20 different T-DNA binary plasmids.

The one or more exogenous nucleic acid molecules in the T-DNA binary plasmid are selected, for example, based on the desired product to be produced. Thus, for example, an exogenous nucleic acid molecule can produce the desired product directly, such as a protein. In another example, the exogenous nucleic acid molecule can produce the desired product indirectly, for example, express a protein involved in (or required for) the production of a desired product, such as a fatty acid.

For example if production of fatty acids by *Lipomyces* cells is desired (such as increasing the production of one or more fatty acids), one or more of the following proteins can be expressed in *Lipomyces* sp. cells using the disclosed methods (exemplary JGI Accession Nos. provided): NADP-malic enzyme (me1; jgi|Lipst1_1|72728), acyl coA synthase (jgi|Lipst1_1|3273), acetyl-coA carboxylase (Acc1: jgi|Lipst1_1|72701), acetyl coA ACP transferase, ACP-S-malonytransferase (jgi|Lipst1_1|309296), fatty acid synthase (FAS; jgi|Lipst1_1|44960), glycerol-3 1-O-phosphate acyltransferase (jgi|Lipst1_1|68496), and diacylglycerol acyltransferase (jgi|Lipst1_1|166982). Such sequences are publicly available (genome.jgi.doe.gov/Lipst1_1/Lipst1_1.home.html).

NADP-malic enzyme (me1) is an enzyme (EC 1.1.1.40) that catalyzes the reaction S-malate+$NADP^+ \leftrightharpoons$ pyruvate+$CO_2$+NADPH. Nucleic acid sequences that can be expressed in *Lipomyces* sp. cells are publicly available. For example JGI genome database Accession Nos. jgi|Lipst1_1|72728 provide exemplary NADP-malic enzyme nucleic acid sequences that can be placed into a T-DNA binary plasmid and expressed in *Lipomyces* sp. cells.

Acetyl-coA carboxylase (ACC) is a biotin-dependent enzyme (EC 6.4.1.2) that catalyzes the carboxylation of acetyl-CoA to produce malonyl-CoA through its two catalytic activities, biotin carboxylase (BC) and carboxyltransferase (CT). ACC is a multi-subunit enzyme. Nucleic acid sequences that can be expressed in *Lipomyces* sp. cells are publicly available. For example JGI genome database Accession Nos. jgi|Lipst1_1|72701 provide exemplary ACC enzyme nucleic acid sequences that can be placed into a T-DNA binary plasmid and expressed in *Lipomyces* sp. cells.

Acyl-carrier-protein (ACP)-S-malonytransferase is an enzyme (EC 2.3.1.39) that catalyzes the reaction: malonyl-CoA+[acyl-carrier protein]$\leftrightharpoons$CoA+malonyl-[acyl-carrier protein]. Nucleic acid sequences that can be expressed in *Lipomyces* sp. cells are publicly available. For example JGI genome database Accession Nos. jgi|Lipst1_1|309296 provide exemplary acyl-carrier-protein (ACP)-S-malonytransferase enzyme nucleic acid sequences that can be placed into a T-DNA binary plasmid and expressed in *Lipomyces* sp. cells.

Fatty acid synthase (FAS) is an enzyme (EC 2.3.1.85) that catalyzes the synthesis of palmitate from acetyl-CoA and malonyl-CoA, in the presence of NADPH, into long-chain saturated fatty acids. Nucleic acid sequences that can be expressed in *Lipomyces* sp. cells are publicly available. For example JGI genomic database Accession Nos jgi|Lipst1_1|44960 provide exemplary FAS enzyme nucleic acid sequences that can be placed into a T-DNA binary plasmid and expressed in *Lipomyces* sp. cells.

Glycerol-3 phosphate 1-O-acyltransferase (GPAM) is an enzyme (EC 2.3.1.15) that catalyzes the chemical reaction: acyl-CoA+sn-glycerol 3-phosphate$\leftrightharpoons$CoA+1-acyl-sn-glycerol 3-phosphate. Nucleic acid sequences that can be expressed in *Lipomyces* sp. cells are publicly available. For example JGI genome database Accession Nos. jgi|Lipst1_1|68496 provide exemplary GPAM enzyme nucleic acid sequences that can be placed into a T-DNA binary plasmid and expressed in *Lipomyces* sp. cells.

Diacylglycerol acyltransferase (DGAT) is an enzyme (EC 2.3.1.20) that catalyzes the formation of triglycerides from diacylglycerol and acyl-CoA. Nucleic acid sequences that can be expressed in *Lipomyces* sp. cells are publicly available. For example JGI genome database Accession Nos. jgi|Lipst1_1|166982 provide exemplary DGAT enzyme nucleic acid sequences that can be placed into a T-DNA binary plasmid and expressed in *Lipomyces* sp. cells.

In some examples, *Lipomyces* sp. cells are transformed with nucleic acid molecules that can permit the transformed *Lipomyces* sp. cells to produce isoprene and farnesine, for example using the enzymes shown in Table 2. Some exemplary sequences are also provided. Thus, in some examples, *Lipomyces* sp. cells are transformed with 1, 2, 3, 4, 5, 6, 7, 8, 9, 10 or 11 of these nucleic acid molecules using the disclosed methods, to generate *Lipomyces* sp. cells that produce isoprene and farnesine.

TABLE 2

Exemplary enzymes for isoprene and farnesene biosynthesis

Pathway I: Mevalonic acid (MVA) pathway for isoprenoids

| Step | Initial product | Enzyme | JGI Acc. No | Intermediate product |
|---|---|---|---|---|
| 1 | Acetyl-CoA | Acetyl-CoA thiolase | 2436/57913/285732 | Acetylacetyl-CoA |
| 2 | Acetylacetyl-CoA | HMG CoA synthase | 63385 | 3-hydroxy-3-methyl-glutaryl-CoA |
| 3 | 3-hydroxy-3-methyl-glutaryl-CoA | HMG-CoA reductase | 5675 | Mevalonate |
| 4 | Mevalonate | Mevalonate kinase | 54023 | Mevalonate-5-P |
| 5 | Mevalonate-5-P | P-Mevalonate-kinase | 37388 | Mevalonate-5-PP |
| 6 | Mevalonate-5-diP | Mevalonate-5-PP decarboxylase | 1591 | Isoprentenyl-PP |
| 7 | Isoprentenyl-PP (IPP) | IPP isomerase | 5292 | Dimethyl allyl diphosphate (DMAPP) |
| 8 | Dimethy lallyl diphosphate | Plant isoprene synthase | | Isoprene |
| 9 | IPP + DMAPP | Farnesyl pyrophosphate synthase | 69224 | Geranyl diphosphate |
| 10 | Geranyl diphosphate | Plant monterpene synthase | | linalool |
| 11 | Sequiterpene diphosphate | Fungal sequiterpene synthase | | farnesene |

In some examples, *Lipomyces* sp. cells are transformed with nucleic acid molecules that can permit the transformed *Lipomyces* sp. cells to produce saturated and/or unsaturated lipids, for example using the enzymes shown in Table 3. Some exemplary sequences are also provided. Thus, in some examples, *Lipomyces* sp. cells are transformed with 1, 2, 3, 4, 5, 6, 7, 8, 9, 10, or 12, of these nucleic acid molecules using the disclosed methods, to generate *Lipomyces* sp. cells that produce saturated and/or unsaturated lipids.

TABLE 3

Exemplary enzymes for saturated and unsaturated lipid biosynthesis

Pathway II: Fatty acid synthesis

| Step | Initial product | Enzyme | JGI Acc. No | Intermediate product |
|---|---|---|---|---|
| 1 | Pyruvate | Pyruvate decarboxylase | 70370 | Acetyl-CoA |
| 2 | Acetyl-CoA | Acetyl-CoA carboxylase | 72701 | Malonyl-CoA |
| 3 | Acetyl-CoA | Acetyl-CoA:ACP transacylase | 6225 | Acetyl-ACP |
| 4 | Malonyl-CoA | Malonyl-CoA:ACP transacylase | 309296 | Molonyl-ACP |
| 5 | Acyl-ACP + Malonyl-ACP | 3-ketoacyl-ACP synthetase | 3273 | 3-oxoscyl-ACP + $CO_2$ + ACP |
| 6 | 3-oxoscyl-ACP + NADPH | 3-ketoacyl-ACP reductase | 2083 | 3-hydroxyacyl-ACP + $NADP^+$ |
| 7 | 3-hydroxyacyl-ACP | 3-ketoacyl-ACP dehydrase | | Crotonyl-ACP |
| 8 | Crotonyl-ACP + NADH | Enoyl-ACP reductase | 61583 | Butyryl-ACP + $NAD^+$ |
| 9 | | Fatty acid synthase | 44960 | |
| 10 | | Glycerol-3P acyltransferase | 68496 | |
| 11 | | Diacylglycerol acyltransferase | 166982 | |
| 12 | | NADP-Malic enzyme | 72728 | |

Pathway III: Unsaturated fatty acids

Δ5 desaturase
Δ6 desaturase
Δ9 desaturase
Δ12 desaturase
Δ15 desaturase
ω3 desaturase Pathway IV: alpha-olefins lubricants

*Jeotgalicoccus* P450 OleT$_{JE}$

In some examples, *Lipomyces* sp. cells are transformed with nucleic acid molecules that can permit the transformed *Lipomyces* sp. cells to produce bio-hydrocarbon fuels. In some examples, *Lipomyces* sp. cells are transformed with nucleic acid molecules that can permit the transformed *Lipomyces* sp. cells to treat wastewater, such as, sewage sludge, starch wastewater, and monosodium glutamate wastewater.

Promoters

Expression of the nucleic acid molecule(s) expressed in the transformed *Lipomyces* sp. cell can be driven by a promoter. In some examples, one promoter is used to drive expression of two or more nucleic acid molecules, such as 2, 3, 4, 5, 6, 7, 8, 9 or 10 different coding sequences. In some examples, different promoters are used to drive expression of two or more nucleic acid molecules. For example, a first promoter can be used to drive expression of a first nucleic acid molecule and a second promoter can be used to drive expression of a second nucleic acid molecule.

Any promoter that allows expression in a *Lipomyces* sp. cell can be used. In one example, a constitutive promoter is use. In a specific example, the constitutive promoter is an *L. starkeyi* translational elongation factor 1α (tef1) promoter or the ura3 promoter, such as one from *L. starkeyi*. Other specific examples are provided in SEQ ID NOS: 31-47, though one skilled in the art will recognize that other promoter sequences can be used, including those having at least 80%, at least 85%, at least 90%, at least 95%, at least 96%, at least 97%, at least 98% or at least 99% sequence identity to any of SEQ ID NOS: 31-47.

*Lipomyces* sp. Cells

Examples of *Lipomyces* sp. cells that can be transformed with the disclosed methods include, but are not limited to those of the following species: *L. arxii, L. doorenjongii, L. japonicus, L. knockii, L. knononenkoae, L. lipofer, L. mesembrius, L. spencer-martinsiae, L. oligophaga, L. orientalis, L. smithiae, L. spencermartinsiae, L. starkeyi, L. suomiensis, L. tetrasporus, L. yamadae,* or *L. yarrowii.* In some examples, the strain of *Lipomyces* sp. cells transformed with the disclosed methods, are *L. doorenjongii* strain NRRL Y-27504, *L. kononenoae* strain NRRL Y-11553, *L. lipofer* strain Y-11555, *L. smithiae* strain NRRL Y-17922, *L. suomiensis* strain NRRL Y-17356, *L. tetrasporus* strain NRRL Y-11562 cells, *L. starkeyi* strain NRRL Y-11557, *L. starkeyi* strain Y-11558, *L. starkeyi* strain Y-27943, *L. starkeyi* strain Y-27944, or *L. starkeyi* strain Y-27945. In some examples, the strain of *Lipomyces* sp. cells transformed with the disclosed methods, are: *L. arxii* strain NRRL Y-17921; *L. japonicas* strain NRRL Y-17848; *L. kockii* strain NRRL Y-2750; *L. lipofer* strain NRRL Y-1351 and NRRL Y-6333; *L. mesembrius* strain NRRL Y-27927, NRRL Y-27928, NRRL Y-27929, NRRL Y-27930, and NRRL Y-27931; *L. spencer-martinsiae* strain NRRL Y-7042; or *L. starkeyi* strain NRRL Y-27507. In one example, *Lipomyces* starkeyi cells are transformed with the disclosed methods.

*Agrobacterium* sp. Cells

Examples of *Agrobacterium* sp. cells that can be used in the disclosed methods include but are not limited to *Agrobacterium tumefaciens* cells, such as *Agrobacterium tumefaciens* strains LBA1100, LBA1126, LBA4404, EHA105 and A348. In one example, *Agrobacterium tumefaciens* strain EHA105 cells are used to transform *Lipomyces* sp. cells with the disclosed methods.

Producing Product(s) from Transformed *Lipomyces* sp

The disclosed transformed *Lipomyces* sp. cells can be used to produce one or more products of interest (such as at least two products, at least 3, at least 4, at least 5, or at least 10 different products, such as 1, 2, 3, 4, 5, 6, 7, 8, 9, 10, 15, or 20 different products), for example by expressing one or more appropriate exogenous nucleic acid molecules in the cells, in addition to the nucleic acid molecule encoding the selective marker. In some examples, an exogenous nucleic acid molecule produces the desired product directly, such as a protein. In another example, the exogenous nucleic acid molecule produces the desired product indirectly, for example, expresses a protein involved in (or required for) the production of a desired product, such as a fatty acid.

Exemplary products that can be produced by the transformed *Lipomyces* sp. cells include but are not limited to, fatty acids, such as unsaturated fatty acids [e.g., arachidonic acid (AA), eicosapentaenoic acid (EPA), docosahexaenoic acid (DHA)], oils, such as palmitic (C16:0), stearic (C18:0), oleic (C18:1) and linoleid (C18:2) acids, and other products such as isoprene, monoterpene, and sesquiterpene.

In one example, one or more products are produced by culturing transformed *Lipomyces* sp. cells provided herein, under conditions in selective culture media that permit expression of the necessary nucleic acid molecules and the selective marker nucleic acid molecule(s). The resulting product is produced directly or indirectly from the nucleic acid molecules. In some examples, the method further includes isolating the product(s) from the selective culture media.

Fermentation of Transformed *Lipomyces* sp. Cells

Methods are provided for producing one or more desired products, such as an oil or hydrocarbon, by culturing the disclosed transformed *Lipomyces* sp. cells in culture media under conditions that the one or more desired products are produced by the transformed *Lipomyces* sp. cells. In general, the culture media and/or culture conditions can be such that the transformed *Lipomyces* sp. cells grow to an adequate density and produce the product efficiently. For large-scale production processes, any method can be used such as those described elsewhere (e.g., see Manual of Industrial Microbiology and Biotechnology, $2^{nd}$ Edition, Editors: Demain and Davies, ASM Press; and Principles of Fermentation Technology, Stanbury and Whitaker, Pergamon).

Briefly, a large tank (e.g., one that is at least 30 gallons, 100 gallons, 200 gallons, 500 gallons, 1000 gallons, or more) containing appropriate culture medium with, for example, D-glucose, D-xylose, L-arabionse, D-galactose, D-mannose, D-cellobiose, or lignocellulosic biomass hydrolysate, carbon source is inoculated with a transformed *Lipomyces* sp. cells, which express one or more exogenous nucleic acid molecule(s) that permit production of the one or more desired products. After inoculation, the *Lipomyces* sp. cells are incubated to allow biomass to be produced. Once a desired biomass is reached, the broth containing the transformed *Lipomyces* sp. cells can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank. For example, the first tank can contain medium with D-glucose, while the second tank contains medium with glucose-xylose.

Once transferred, the transformed *Lipomyces* sp. cells can be incubated to allow for the production of one or more products. Once produced, any method can be used to isolate the formed product. For example, common separation techniques can be used to remove the biomass from the broth, and common isolation procedures (e.g., extraction, distillation, centrifugation, and ion-exchange procedures) can be used to obtain the one or more products from the cell-free broth. Alternatively, the product can be isolated while it is being produced (e.g., ethylene, isoprene, or a volatile chemical), or it can be isolated from the broth after the product production phase has been terminated.

Example 1

Materials and Methods

This example provides details on the Materials and methods used for the results described in Examples 2-10 below. Strains, Media, Culture Methods, and Microscopic Observation of Cell Growth

*Escherichia coli* strain Top10 and *Saccharomyces cerevisiae* strain YVH10 were used as hosts for routine cloning and gap repair experiments. The *Agrobacterium tumefaciens* strains used are listed in Table 4. The LBA4404 strain was obtained from American Type Culture Collection (Manassas, Va.). LBA1100 and LBA1126 strains were provided by Dr. Paul Bundock from University of Leiden, The Netherlands. The EHA105 and A348 strains were provided by Dr. Eugene Nester at University of Washington (Seattle, Wash.).

TABLE 4

*Agrobacterium* strains used

| Strain | Chromosomal background | Disarmed Ti Plasmid | Reference |
|---|---|---|---|
| EHA105 | C58 (rifampicin resistance) | pTiBo542 ΔT-DNA | Hood et al., *Trans Res* 2: 208-218, 1993 |
| A348 (ATCC51317) | C58 (rifampicin resistance) | pTiA6NC | Sciaky et al., *Plasmid* 1: 238-53, 1978 |
| LBA1100 | C58 (rifampicin resistance) | pTiB6 ΔT-DNA | Beijersbergen et al, *Science* 256: 1324-7, 1992 |
| LBA1126 | C58 (rifampicin resistance) | pTiB6 ΔT-DNA VirGI77V virA-TAR | Beijersbergen et al, *Science* 256: 1324-7, 1992 |
| LBA4404 ATCC68111 | Ach5 (rifampicin resistance) | pTiAch5 ΔT-DNA | Hoekema et al., *Nature*, 303: 179-181, 1983 |

Various *Lipomyces* species and strains [*L. doorenjongii* (NRRL Y-27504); *L. kononenkoae* (NRRL Y-11553); *L. lipofer* (NRRL Y-11555); *L. smithiae* (NRRL Y-17922); *L. starkeyi* (NRRL Y-11557; Y-11558; Y-27493; Y-27494; and Y-27495); *L. suomiensis* (NRRL Y-17356); and *L. tetrasporus* (NRRL Y-11562)] were obtained from ARS culture Collection Center (Peoria, Ill.) and grown on yeast peptone dextrose (YPD) medium agar plate at 30° C. for culture maintenance. Besides the gap repair, yeast synthetic complete dropout supplemented with uracil and YPD media were prepared and used for evaluation of antibiotic selection and *Agrobacterium*-mediated transformation for various *Lipomyces* strains. The culture medium for lipid production was modified on the basis of *Aspergillus niger* minimal medium (Dai et al., 2013) with the following changes: 80 g/l of glucose and 1.43 g/L of ammonium chloride. In general, two types of culture inoculation were carried out for *Lipomyces* strains: 2 ml in 16×125 mm glass culture-tubes or 50 ml cultures in Pyrex brand 250 ml glass flasks. The cultures were maintained at 30° C. and 200 rpm in a New Brunswick Innova 44 incubator shaker (Eppendorf, Inc., Enfield, Calif.). The biomass for genomic DNA isolation was harvested by centrifugation at room temperature and 4500×g, washed twice with distilled $H_2O$ and dried by lyophilization. The microscopic observation of *Lipomyces* cell growth in different culture conditions was imaged using an Olympus inverted system microscope (Olympus, Miami, Fla.).

Transgene Expression Vector Construction

The vectors pRS426 (Christianson et al., 1992) and pZD663 that was mainly derived from pBI121 (Jefferson et al., 1987) by replacing the all DNA fragment between left and right border of T-DNA region with a synthetic fragment containing eleven unique multiple cloning sites (PmeI, HindIII, BamHI, XbaI, ScaI, MluI, XhoI, HpaI, SacI, BglII, & EcoRI), were used as backbone ones for transgene expression cassette construction. The transgene expression cassettes were first prepared by yeast gap repairing and then sub-cloned into the T-DNA binary vector pZD663 and their subsequent ones. The first transgene expression cassette was *E. coli* hygromycin B phosphotransferase (hph) under the control of *L. starkeyi* translation elongation factor 1α (Tef1) promoter (FIG. 5A). The Tef1 promoter DNA fragment was isolated by PCR from *L. starkeyi* genomic DNA with a pair of oligonucleotides (SEQ ID NOS: 1 and 2) and the coding region of hph from plasmid DNA vector pCB1003 (Carroll et al., 1994) with SEQ ID NOS: 3 and 4. The DNA fragments were fused together into pRS426 by yeast gap repairing (Colot et al, 2006; Dai et al., 2013). The tef1-hph transgene expression cassette was excised with Pme I and sub-cloned into T-DNA binary vector pZD663 (FIG. 5B), which was further mobilized into *A. tumefaciens* EHA105.

For the trpC gene deletion construct (FIG. 5C), the DNA fragments of the upstream and downstream regions of trpC gene and the tef1-hgh selection marker gene were isolated from *L. starkeyi* genomic DNA or plasmid DNA by PCR (ptef1-hph (SEQ ID NOS: 7 and 8) was flanked by 2 kb PCR fragments 5'-upstream (oligo pair SEQ ID NOS: 5 and 6) and 3'-downstream (SEQ ID NOS: 9 and 10) of TrpC gene). The PCR DNA fragments were fused together by yeast gap repairing. The 6.7 kb plasmid DNA fragment of 5'-TrpC-pTef1-hph-3'-TrpC was sub-cloned into T-DNA binary vector pZD663, which was further mobilized into *A. tumefaciens* EHA105.

To construct the T-DNA binary vector of pZD663hph, the u3-hph-ura3 transgene cassette was first prepared by double-joint PCR method (Yu et al., 2004) with the DNA fragments of upstream (promoter) and downstream (transcription terminator) regions of *L. starkeyi* uro3 (orotidine 5'-phosphate decarboxylase) gene and *E. coli* hph coding region isolated by PCR with a pair of oligonucleotides [SEQ ID NOS: 11 and 13 (ura3 upstream region), 14 and 15 (hph), 16 and 18 (ura3 downstream region) and 12 and 17 (whole DNA fragment of 5'-ura3-hph-ura3' cassette), respectively). The final ura3-hph-ura3 cassette was cloned into T-DNA binary vector pZD663 at Pme I restriction enzyme site to generate the T-DNA binary vector pZD663hph that was used the following two transgene expression vector construction.

To construct the ptef1-GUS transgene cassette (FIG. 5D), *L. starkeyi* tef1 promoter and its transcription terminator and coding region of GUS reporter gene were isolated from *L. starkeyi* genomic DNA and pBI221 plasmid DNA (Jefferson, 1987) by PCR with oligonucleotide pairs (GUS reporter SEQ ID NOS: 19 and 20, tef1 transcriptional terminator SEQ ID NOS: 23 and 24, and *L. starkeyi* tef1 promoter SEQ ID NOS: 21 and 22, respectively). The PCR fragments were then fused together by yeast gap repairing. The whole ptef1-GUS fragment was inserted into the T-DNA binary vector pZD663hph at restriction enzyme HpaI site (FIG. 5D).

Similarly, to construct tef1-ME1 transgene expression cassette (FIG. 5E), the tef1 promoter, ME1 coding region and its transcriptional terminator were isolated from the *L. starkeyi* genomic DNA by PCR with the oligonucleotide pairs (SEQ ID NOS: 25 and 26 and 27 and 28) and fused together into linearized pZD663hph vector with Gibson assembly kit (New England Biolabs, Ipswich, Mass.).

Evaluation of Antibiotic Selection Effectiveness to Various *Lipomyces* Strains

For effective selection of transgene expression in *Lipomyces* strains, several antibiotics were chosen to examine their effects on *Lipomyces* growth on yeast synthetic complete (SC, Sunrise Science Products, San Diego, Calif.) and yeast extract-peptone-detrose (YPD) medium plates, which included phosphinothricin ammonium (basta), geneticin (G418), hygromycin B (hyg), pyrithiamine and Zeocin (Zeo). Two day old *Lipomyces* cells grown in YPD liquid culture were used for evaluation of the antibiotic selection on the agar plates of SC or YPD. The original cells were diluted sequentially in 1:10 ratio with dH$_2$O for four times and 10 µl cells from original culture and each dilution were spotted onto the proper agar medium plates. The plates were incubated in 30° C. incubator for 3 days. The inhibition effects of selected antibiotics on the selected plate were documented with Nikon D300s SLR digital camera (Nikon Inc., Melville, N.Y.) or the stereomicroscope-Leica MZ16 (Leica Microsystems, Buffalo Grove, Ill.).

Lithium Acetate (LiAc)-Mediated, Protoplast, Electroporation, and *Agrobacterium*-Mediated Transformation (A). LiAc-Mediated Transformation:

Two day old *L. starkeyi* cells grown in YPD liquid culture medium were used to examine the feasibility of LiAc-mediated, protoplast and electroporation transformation. Approximately $5\times10^6$ to $1\times10^8$ liquid culture cells of *L. starkeyi* (NRRL Y-11557 & NRRL Y-11558) or *L. kononenkoae* (NRRL Y-11553) were aliquoted into a microcentrifuge tube and centrifuged at 10,000×g for 15 seconds. After discarding the culture medium, the pelleted cells were washed once with dH$_2$O and twice with 100 mM LiAc, sequentially. The cell pellets were re-suspended with 360 µl of transformation mix [240 µl PEG 3350 (50% w/v); 36 µl LiAc (1.0 M); 25 µl boiled sheared salmon sperm DNA (5 µg/µl); 1~5 µg of plasmid or PCR DNA of tef1-hph cassette and dH$_2$O] and incubated in a 42° C. water bath for 20 to 60 min. After heat treatment, the cells were pelleted down in microcentrifuge at 10,000×g for 15 seconds and washed once with 1 ml dH$_2$O. The cells was re-suspended in 100 µl H$_2$O and spread onto the 10 mg/L hygromycin B selection YDP medium agar plates. The transformed cells were incubated at 30° C. for 4 to 5 days for growth selection of candidate transformed cells.

(B). Protoplast Transformation:

About 5 to 8 colonies of *L. starkeyi* were inoculated in 100 ml YPD liquid culture medium and grown to cell concentration of $4\sim5\times10^7$ cells/ml. The cells were harvested in a 50 ml centrifuge tube and centrifuged in Sorvall RC6 plus Centrifuge (Thermo Scientific, Waltham, Mass.) with swinging bucket rotors at 4000×g for 5 min and washed with 30 ml dH$_2$O once. The cells were re-suspended in 30 ml of protoplasting buffer [30 mg/ml Vino Taste Pro (Novozyme North America, Franklinton, N.C.), 1 M sorbitol, and 10 mM sodium phosphate buffer, pH5.8] and incubated at 30° C. and 80 rpm for 1 hr. The protoplasts were spun down at 4500×g for 10 min and washed twice in 20 ml of STC solution (1 M sorbitol, 50 mM Tris-HCl, pH8.0 and 50 mM CaCl$_2$). The protoplasts were diluted, enumerated with a hemocytometer, and re-suspended with STC solution to a final concentration about $1\times10^9$ protoplasts/ml. For each transformation, about $1.5\times10^8$ protoplasts (150 µl) were mixed with 15 µl of DNA mix (5 µg linearized plasmid DNA and 5 µg of boiled sheared salmon sperm DNA) and incubated on ice for 15 min. Then, 1 ml of 40% PEG (PEG4000 in STC solution) was added, gently mixed well, and incubated at room temperature for 15 min. The treated protoplasts were mixed with 10 ml of YPD liquid culture medium containing 1 M sorbitol in 15 ml centrifuge tube and gently shaken at 80 rpm and 30° C. for 5 hrs. Finally, the protoplasts were pun down at 4500×g for 5 min, spread onto 10 mg/l hygromycin B selection YPD medium agar plate containing 1 M sorbitol, and incubated at 30° C. for 4 to 5 days.

(C). Electroporation Transformation:

About $2\times10^9$ *L. starkeyi* cells grown in YPD liquid culture for two days were pelleted by centrifugation at 3000×g for 5 min. The cells were re-suspended in 25 ml of LiAc-DTT-TE buffer (0.1 M LiAc; 10 mM DTT; 10 mM Tris-HCl, pH7.5; 1 mM EDTA) and incubated at room temperature for 1 hr. The cells were then washed twice with 25 ml ice-cold water and once with 10 ml ice-cold 1 M sorbitol. Finally, the cell pellets were re-suspended in 100 µl of 1 M sorbitol to yield $4\times10^9$ cells/ml. Fifty microliters of cells were mixed with 5 µl of DNA fragments (about 100 ng) in a 0.2 cm electroporation cuvette and incubated on ice for 5 min. After an electric shock with total discharge voltage of 1.5 kv, 200 ohms resistance on voltage booster, and pulse control of 25 uF, the cells were immediately mixed with 1 m ice-cold 1M sorbitol gently, and spread onto the medium agar plates with 10 mg/l hygromycin B selections.

(D). *Agrobacterium*-Mediated Transformation:

The transgene expression T-DNA binary vector pZD663-Tef1-hph (FIG. 5B) was mobilized into 5 different *Agrobacterium tumefaciens* strains listed in Table 4 (EHA105, A348, LBA1100, LBA1126, and LBA4404) by freeze-thaw technique (Holsters et al., 1978). Plasmid DNA from the transformed *Agrobacterium* clones were isolated and digested with various restriction endonucleases and analyzed in agarose gel electrophoresis to confirm transformation of transgene expression construct. The transformed *A. tumefaciens* strains were used for *Agrobacterium*-mediated *Lipomyces* transformation.

The cell density of the overnight culture of *A. tumefaciens* strains grown in YEP (10 g/L yeast extract, 10 g/L peptone and 5 g/L NaCl) medium was determined spectrophotometrically and aliquoted into 5 ml induction medium [IM; (De Groot et al, 1998)] with or without 0.2 mM acetosyringone (AS) to 0.2 OD$_{600}$ of *Agrobacterium* cells for additional 5 to 6 hours of growth. Three different concentrations of two day old *Lipomyces* cells grown in YPD liquid culture medium at 30° C. and 200 rpm ($5\times10^6$, $1\times10^7$, and $5\times10^7$ cells) were aliquoted into microcentrifuge tubes and washed twice with IM buffer. Five combinations of *Lipomyces* and *Agrobacterium* cells mixtures ($5\times10^6$, $1\times10^7$, or $5\times10^7$ *Lipomyces*: 100 µl *Agrobacterium* cells with 0.2 mM AS; $1\times10^7$ *Lipomyces*: 300 µl of *Agrobacterium* cells with 0.2 mM AS; and $1\times10^7$ *Lipomyces*: 100 µl of *Agrobacterium* cells without AS) were mixed well in a final volume of 200 µl and spread onto the 25×30 mm sterile 0.45 µm Hybond-N$^+$ nylon membrane (GE Healthcare Bio-Sciences, Pittsburgh, Pa.) laid on the IM agar plate with or without 0.2 mM AS.

After 2 days incubation at room temperature (about 23° C.), the transformed *Lipomyces* cells were washed down from the nylon membrane with 2 ml dH$_2$O and one fifth of cells were spread onto the YPD agar plate with proper antibiotics (10 mg/l hygromycin B and 250 mg/l cefotaxime for growth selection of transformed *Lipomyces* and inhibition of *Agrobacterium tumefaciens* growth). The transformed *Lipomyces* cells appeared visibly on the plate after incubation at 30° C. for 3 to 6 days.

Total Genomic DNA Isolation for PCR and Southern Blotting Analysis

Total genomic DNA was isolated from *Lipomyces* cells according to the SDS extraction method described previously with some modifications (Dai et al., 2013; Dellaporta et al., 1983). Briefly, the SDS concentration in the extraction buffer was added to 2.85%. The genome DNA in the supernatants of cell extracts was precipitated by 2-propanol and genomic DNA pellets were re-suspended in 200 µl TE (10 mM Tris-HCl, pH 8.0 and 1 mM EDTA) buffer and 25~50 µg of RNase. After RNase treatment, the genomic DNA in the TE buffer was extracted twice with equal volume of phenol:chloroform and once with chloroform. Due to the high contamination of extracellular polymer substance, the genomic DNA in the supernatant was further treated with 2% polyethylene glycol (PEG) 8000 and 0.6 M NaCl to precipitate the extracellular polymer substance. The genomic DNA was finally precipitated with 8% of PEG 8000 and 0.6 M NaCl by centrifugation at 17,000×g and 4° C. for 15 min. The genomic DNA pellets were re-suspended into 0.3 M sodium acetate (pH5.2) and finally precipitated with 2.5× volume of 95% ethanol and centrifugation of 12,000×g for 10 min. Finally, the genomic DNA was re-suspended in 80~100 µl 10 mM Tris-HCl (pH8.0) buffer and quantified with Qubit fluorometer (Invitrogen, Carlsbad, Calif.). One microgram of total genomic DNA was digested with the restriction endonuclease SacI. The genomic DNA fragments were separated in 1% agarose gel electrophoretically and transferred onto the Hybond-N+ nylon membrane (GE Healthcare Bio-Sciences, Pittsburgh, Pa.) with alkaline capillary transfer method. The 2.2 kb pTef1-hph plasmid DNA fragment containing the *L. starkeyi* tef1 promoter and bacterial hph coding sequence was used for preparation of the biotin-labeled probe. The genomic DNA fragments on the Hybond-N+ nylon membrane was hybridized with the biotin-labeled probe overnight at 60° C. and 6 rpm in the Pro-blot Hybridization Oven (Labnet International, Edison, N.J.). The genomic DNA on the hybridized membrane was visualized with North2South chemiluminescent detection kit (Pierce Protein Research Products, Rockford, Ill.).

Oligonucleotides

The oligonucleotides used in the Examples below are shown in Table 5.

TABLE 5

Oligonucleotides for DNA fragment isolation

| SEQ ID NO | |
|---|---|
| | Tef1-hph construct with yeast gap repairing |
| 1 | gtaacgccagggttttcccagtcacgacggtttaaacaccattaa gattcactgtccttg |
| 2 | TTTGCCGGATCGGTCTGCTAACAGCTTACTTCTACAGGGAcctga actcaccgcgacgtc |
| 3 | gacgtcgcggtgagttcaggTCCCTGTAGAAGTAAGCTGTTAGCA GACCGATCCGGCAAA |
| 4 | gcggataacaatttcacacaggaaacagcgtttaaaccggtcggc atctactctatt |
| | trpC upstream-tef1-hph-trpC downstream |
| 5 | GTAACGCCAGGGTTTTCCCAGTCACGACGGAGCTCAGATCAGCAT CTATCGCTCGAT |
| 6 | aggaatagagtagatgccgaccgAGTGTGGGAGGCAACCAAT |
| 7 | <u>ATTGGTTGCCTCCCACACT</u>cggtcggcatctactctattcct |
| 8 | TCTGGCTTTACCCAATCAGCTagatatcgggccatcagggat |
| 9 | atccctgatggcccgatatct<u>AGCTGATTGGGTAAAGCCAGA</u> |
| 10 | GCGGATAACAATTTCACACAGGAAACAGCgtttaaacAGCTATGG AGAGCGGACTTGT |
| | Ura3-hgh-ura3 binary vector construct |
| 11 | Ggacaacatctcaagtctgc |
| 12 | tctcaagtctgctgttcagc |
| 13 | CGTCGCGGTGAGTTCAGGCATgttgaatttagggatatactgtag |
| 14 | CTACAGTATATCCCTAAATTCAACatgcctgaactcaccgcgacg |
| 15 | CTGCCCTTCACTCATCAATTACCAAcggtcggcatctactctatt |
| 16 | AATAGAGTAGATGCCGACCGttggtaattgatgagtgaagggcag |
| 17 | AAGGAGACCTGGAGTATCTC |
| 18 | GCAACGAGTTCATGCTTGAG |
| | Tef1-gus construct |
| 19 | GTAACGCCAGGGTTTTCCCAGTCACGACGttaaacAGATATCGG GCCATCAGGGA |
| 20 | gttggggtttctacaggacgtaaTCCCTGTAGAAGTAAGCTGTTA GCA |
| 21 | TGCTAACAGCTTACTTCTACAGGGAttacgtcctgtagaaacccc aac |
| 22 | ACTTCTTGGAAGCCTTGATGGCtattcattgtttgcctccctgct |
| 23 | agcagggaggcaaacaatgaataGCCATCAAGGCTTCCAAGAAGT |
| 24 | GCGGATAACAATTTCACACAGGAAACAGCaagcttACTGCGTTCA TTGCTGTGACT |
| | Tef1-ME1 construction |
| 25 | ccgcagatctgagctACCATTAAGATTCACTGTCCTTGATC |
| 26 | tacagggaGCTCCTAAATCGTCGACTCG |
| 27 | ttaggagcTCCCTGTAGAAGTAAGCTGTTAG |
| 28 | agcagacttgagatgcCCGTCCTGGTTCTGGACC |
| | Transgene expression confirmation |
| 29 | GTACTTCTACACAGCCATCGGTCCA |
| 30 | CGTTATGTTTATCGGCACTTTGCAT |

β-Glucuronidase (GUS) Activity Measurement

Two ml of 2 to 3 day old transgenic *Lipomyces* cells grown in YPD liquid culture with 10 mg/l hygromycin B and 250 mg/l of cefotaxime that inhibits *Agrobacterium* growth, which contain both hygromycin B phosphotransferase (hph) selection-marker gene under the control of ura3 promoter and its transcriptional terminator and the β-glucuronidase (GUS) reporter gene under the control of *L. starkeyi* tef1 promoter and its transcriptional terminator (FIG. 5D), were harvested by centrifugation at 10,000 g for 30 seconds. The cell pellets were washed once with 1 ml sterile dH$_2$O, centrifuged again to remove the dH$_2$O, and stored at −80° C. until the use. Two hundreds microliters of the ice cold GUS enzyme extraction buffer (50 mM phosphate buffer, pH 7.0; 7 mM β-mercaptoethanol; 1 mM EDTA; 0.1% Triton X-100; 0.1% Sodium laury sarcosine) were added into the cell pellets. The transgenic *Lipomyces* cells were lysed on ice 4 times by ultrasonic lysis with a micro-tip connected to the Cole-Parmer ultrasonic homogenizer 4710 Series (Cole Parmer North America, Vernon Hills, Ill.) that was set with 70% duty cycle and the output control of 3. Lysis time was 5 seconds and 1 min intervals on ice. Cell debris was pelleted by centrifugation at 15,000×g and 4° C. for 10 min and the supernatants were transferred into new microcentrifuge tubes for GUS activity and total soluble protein measurement.

The GUS activity was quantified spectrophotometrically by monitoring 4-methylumbelliferone (MU) released from 4-methylumbelliferyl β-D-glucuronide (MUG) in the microplate wells. The methods for GUS activity and MU calibration standard measurements were performed as described in Gallagher, 1992 and Jefferson et al, 1987. Briefly, the GUS activity assay was started by mixing the assay buffer [cell extraction buffer+5.68 mM 4-methylumbelliferyl-β-D-glucuronide (MUG)] and cell extract supernatants at final volume of 1004 incubated at 37° C., and terminated by adding 150 µl of 0.2 M Na$_2$CO3 at different incubation periods. The 4-methylumbelliferone (MU) released from 4-methylumbelliferyl β-D-glucuronide (MUG) was quantified spectrophotometrically with SpectraMax M5/M5e multimode microplate reader (Molecular Devices, Sunnyvale, Calif.) with the wavelengths set at 365 and 460 nm for excitation and emission, respectively. The total soluble proteins in the supernatants were also determined spectrophotometrically with coomassie (Bradford) protein assay kit (Thermo Scientific, Rockford, Ill.) in the microplate setting with three replicates.

NADP-Malic Enzyme Activity Measurement

NADP-malic enzyme activity was measuring using an adapted protocol described by Sigma-Aldrich Company (St. Louis. Mo.) with the following modification: cell extraction buffer including 80 mM HEPES (pH 7.6), 2 mM dithiothreitol (DTT), 5 mM MnCl2 and 0.5% Triton X-100 and enzyme assay buffer containing 80 mM HEPES (pH 7.6), 2 mM dithiothreitol (DTT), 5 mM MnCl2, 0.5 mM of NADP and 10 mM L-malate. The enzyme measurement was initiated by adding the supernatants of sonication-lysis cells from centrifugation at 10,000×g and 4° C. for 10 min. For enzyme measurement in a microplate format, 200~300 µg of total soluble proteins was added into the well containing the reaction buffer to reach final volume of 200 µl. The reaction buffer was warmed up to room temperature and the reaction was initiated by adding the proper amounts of supernatants of cell extracts. After initially shaking for 5 seconds in the SpectraMax M5/M5e multimode microplate reader (Molecular Devices, Sunnyvale, Calif.), the NADPH generated from the ME reaction was monitored automatically by measuring OD$_{340}$ absorbance at 10 seconds intervals for 3 minutes.

Example 2

Time-Course of *Lipomyces* Starkeyi Growth in Various Culture Media

Culture conditions are critical for optimal cell growth and division, genetic transformation, and chemical production. Although *L. starkeyi* has been used in studies for several decades, most research efforts have focused on the conditions for improving lipid production. To achieve optimal transformation, the baseline growth of *Lipomyces* starkeyi in defined culture media was determined.

*L. starkeyi* NRRL Y-11557 cells were grown in liquid cultures of yeast-peptone-dextrose (YPD) medium, or *Aspergillus* minimal medium (MM) with either sodium nitrate (NaNO$_3$) or ammonium chloride (NH$_4$Cl) as the nitrogen source at 30° C. and 200 rpm for up to 60 hours. At different time points, cells were counted with a hemocytometer. After 48 hours of growth, cells were imaged using Olympus inverted system microscope.

*L. starkeyi* (NRRL Y-11557) was initially grown in an YPD liquid flask culture at 30° C. and 200 rpm for 2 days. Then, the seed culture was used to inoculate the 50 ml liquid flask cultures of YPD or *Aspergillus* minimal medium (MM: 10 g/l glucose, 6 g/l NaNO$_3$, 0.52 g/l KCl, 0.52 g/l MgSO$_4$.7H$_2$O, 1.52 g/l KH$_2$PO$_4$, 44 mg/l ZnSO$_4$.7H$_2$O, 22 mg/l H$_3$BO$_3$, 10 mg/l MnCl$_2$.4H$_2$O, 10 mg/l FeSO$_4$.7H$_2$O, 3.2 mg/l CoCl$_2$.6H$_2$O, 3.2 mg/l CuSO$_4$.5H$_2$O, 2.2 mlg/l NH$_4$MO$_7$O$_{24}$.H$_2$O, and 50 mg/l EDTA) or NaNO$_3$ of MM medium replaced by HN$_4$Cl. About 100~200 µl of cell cultures were transferred into the microcentrifuge tubes contains proportional amounts of dH$_2$O and mixed for cell numeration or imaging under light microscopy.

As shown in FIG. 1A, *L. starkeyi* maintains exponential growth between 15 to 48 hours in YPD medium culture, while its growth was very low in minimal medium (MM) with either sodium nitrate (NaNO$_3$) or ammonium chloride (NH$_4$Cl) as nitrogen source (but better with MM containing NH$_4$Cl). When 10% of YPD (0.1 YPD) was used by itself or mixed with MM culture medium, *L. starkeyi* growth responses were similar to the culture with YPD. Thus, *L. starkeyi* grows well in nitrogen-rich culture media.

Figure 1B:
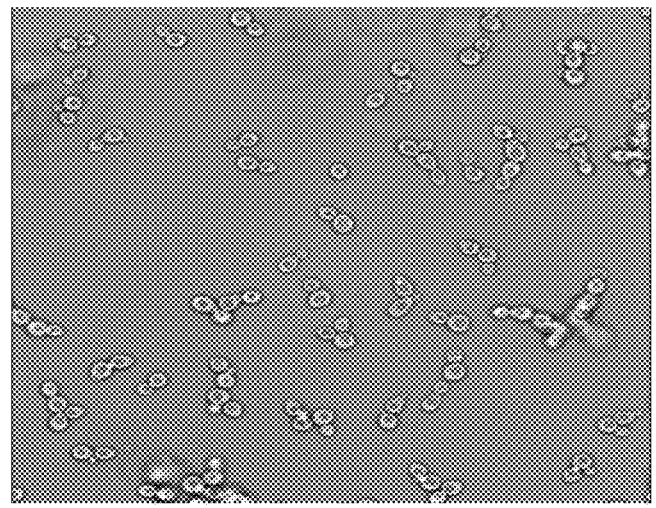
FIG. 1B is a digital image showing growth of *L. starkeyi* in YPD liquid culture medium at 30° C. and 200 rpm after 48 hrs.

The microscopic observation (FIG. 1B) shows that the most cells were maintained at bud-growth stages (actively dividing) after 48 hours culture at 30° C. and 200 rpm. Therefore, 2 day YPD cultures or MM containing NH$_4$Cl of *Lipomyces* cells were used for the *Agrobacterium*-mediated transformation and transgene expression studies described in the Examples below.

Example 3

Identification of Selective Antibiotic

In order to have an effective selection for the *Lipomyces* transformation, several antibiotics (basta, G418, hygromycin B, pyrithiamine, and Zeocin™) were tested to evaluate their effectiveness in growth suppression on yeast synthetic complete (SC) medium agar plates.

About 5 to 10 colonies of 4 day old *Lipomyces* strains (except *L. lipofer* NRRL Y-11555 that required additional 4 days growth and more colonies due to its slow growth) grown on YPD medium agar plates were transferred into a 50 ml YPD liquid flask culture and grown at 30° C. and 200 rpm for 50 hrs. Ten microliters of 2 day old cultures were diluted in 1/10 series and 10 µl of original or diluted ones were spotted on SC medium agar plates containing either 1 mg/l basta, 400 mg/l G418, 100 mg/l hygromycin B, 0.1 mg/l pyrithiamine, or 50 mg/l Zeocin™ or onto YPD medium agar plates containing 2.5 mg/l of hygromycin B and grown at 30° C. for 150 hrs. The plates were photographed at the end of growth. The *L. starkeyi* strains included: NRRL Y-11557, NRRL Y-11558, NRRL Y-27493, NRRL Y-27494 and NRRL Y-27495 and other *Lipomyces* species included: *L. doorenjongii* (NRRL Y-27504), *L. kononenkoae* (NRRL Y-11553), *L. lipofer* (NRRL Y-11555), *L. smithiae* (NRRL Y-17922), *L. suomiensis* (NRRL Y-17356); and *L. tetrasporus* (NRRL Y-11562).

Figure 2:
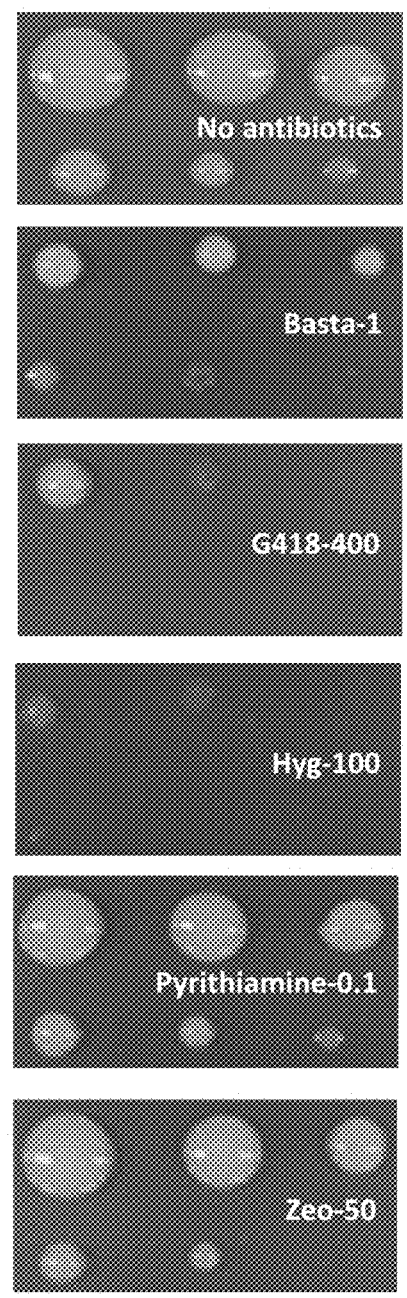
FIG. 2 is a digital image showing growth of *L. starkeyi* on yeast synthetic complete (SC) medium agar plates in the presence of various antibiotics [1 mg/l basta (basta-1), 400 mg/l geneticin (G418-400), 100 mg/l hygromycin B (Hyg-100), 0.1 mg/l pyrithiamine (PT-0.1), or 50 mg/l Zeocin (Zeo-50)].

Initially, the *L. starkeyi* was examined its growth suppression in various antibiotics listed above and as shown in FIG. 2. Both 400 mg/l G418 and 100 mg/l hygromycin B are effective antibiotics for growth selection of *L. starkeyi*. Therefore, the hygromycin B was selected for the subsequent examination of its effects on *Lipomyces* growth described below.

Figure 3:
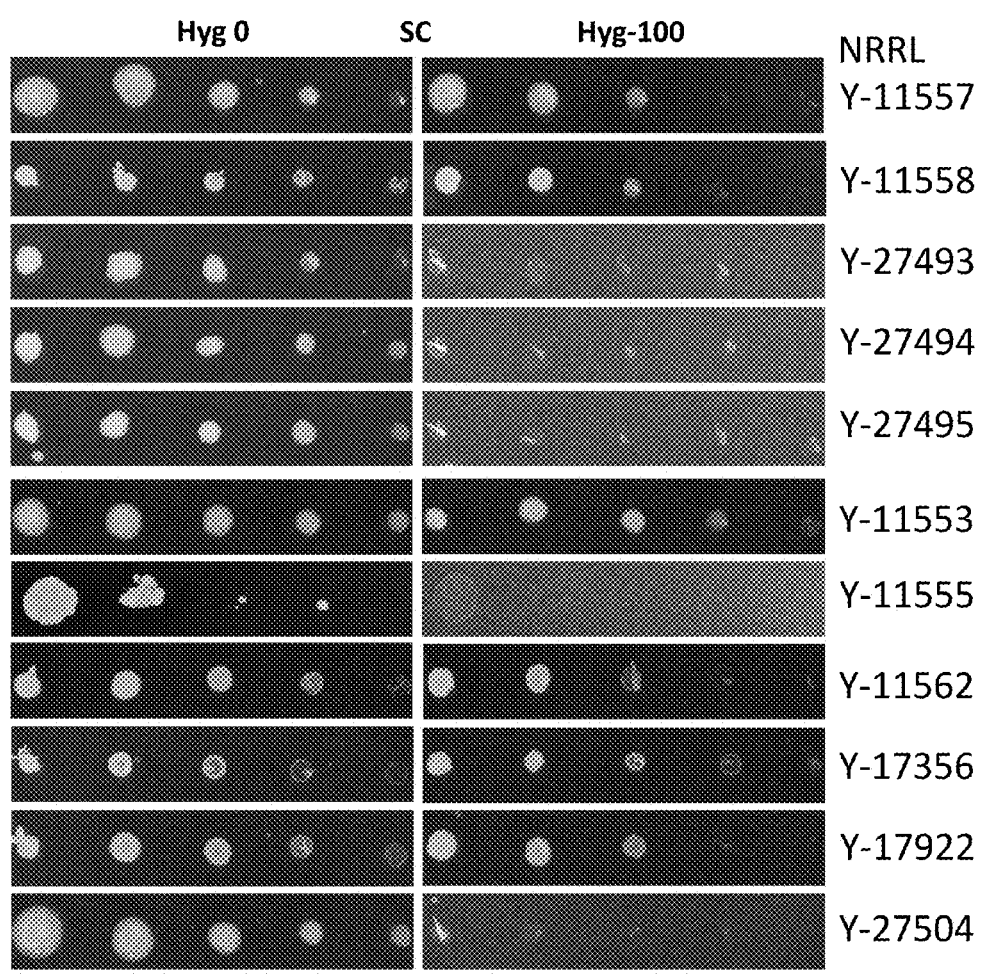
FIG. 3 is a digital image showing growth of various *L. starkeyi* stains and *Lipomyces* species on complete synthetic medium agar plates in the absence or presence of 100 mg/L hygromycin B at 30° C. for 3 days. The strain number shown on the figure corresponds to the following *Lipomyces* species: NRRL Y-11557; NRRL Y-11558; NRRL Y-27493; NRRL Y-27494; and NRRL Y-27495 for *L. starkeyi*; NRRL Y-11553 for *L. kononenkoae*; NRRL Y-27504 for *L. doorenjongii*; NRRL Y-11555 for *L. lipofer*; NRRL Y-17922 for *L. smithiae*; NRRL Y17356 for *L. suomiensis*; and NRRL Y-11562 for *L. tetrasporus*.

The effectiveness of hygromycin B on growth suppression of various *L. starkeyi* stains and other *Lipomyces* species were examined on SC medium agar plates and demonstrated various responses to the 100 mg/L hygromycin B (FIG. 3). 100 mg/l hyg could effectively suppress the growth of three other *L. starkeyi* strains (NRRL Y-27493, NRRL Y-27494, and NRRL Y-27495), *L. lipofer* (NRRL Y-11555) and *L. doorenjongii* (NRRL Y-27504). Thus, 100 mg/L hygromycin B can be used when selecting for transformants of *L. starkeyi* strains NRRL Y-27493, NRRL Y-27494, and NRRL Y-27495, as well as *L. lipofer* strain Y11555 and *L. doorenjongii* strain Y-27504.

Figure 4:
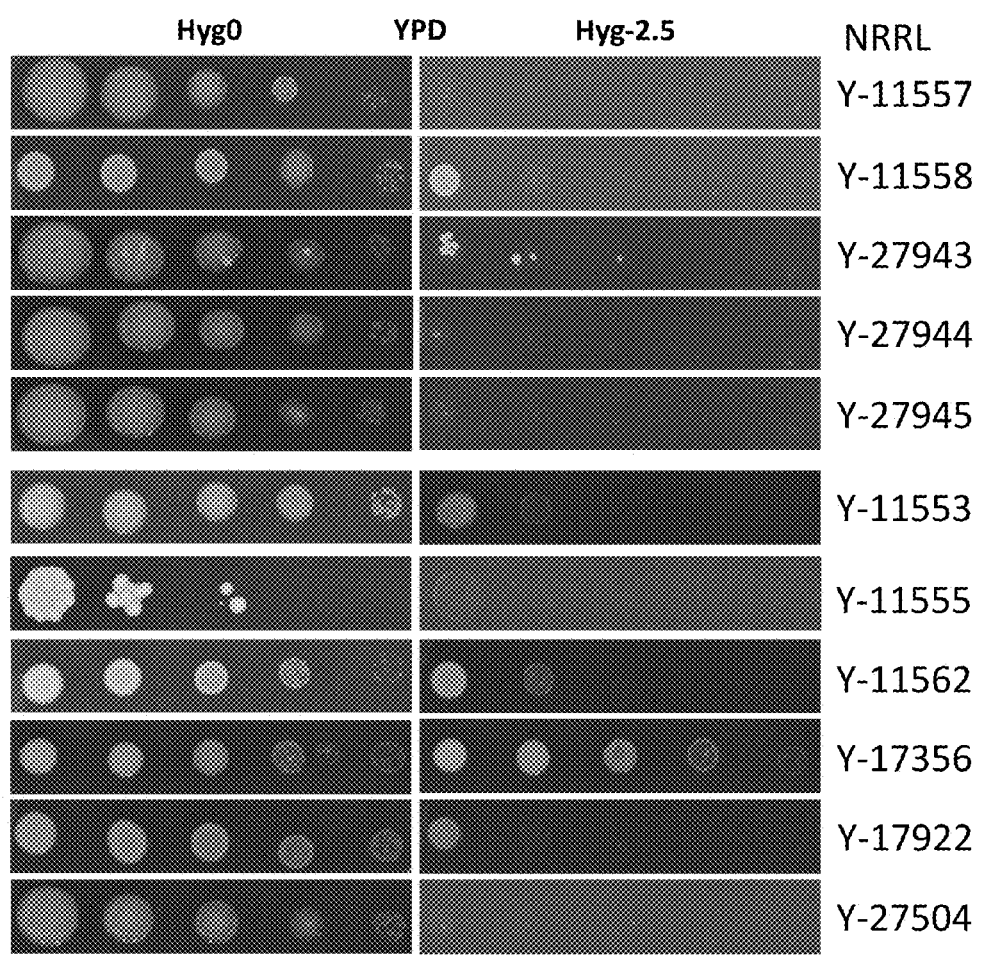
FIG. 4 is a digital image showing growth of various *L. starkeyi* stains and *Lipomyces* species on YPD agar plates with or without 2.5 mg/L hygromycin B at 30° C. for 3 days. The strain number shown on the figure corresponds to the following *Lipomyces* species: NRRL Y-11557; NRRL Y-11558; NRRL Y-27493; NRRL Y-27494; and NRRL Y-27495 for *L. starkeyi*; NRRL Y-11553 for *L. kononenkoae*; NRRL Y-27504 for *L. doorenjongii*; NRRL Y-11555 for *L. lipofer*; NRRL Y-17922 for *L. smithiae*; NRRL Y17356 for *L. suomiensis*; and NRRL Y-11562 for *L. tetrasporus*.

The effectiveness of hygromycin B on growth suppression of various *L. starkeyi* stains and *Lipomyces* species were further examined on YPD agar plates (FIG. 4). Surprisingly, 2.5 mg/L hygromycin B was sufficient to suppress the growth of all *L. starkeyi* strains and *Lipomyces* species on the YPD agar plates, except *L. suomiensis* strain NRRL Y-17356 that needed at least 10 mg/l hygromycin B. Similarly, 10 mg/l hygromycin B also had an effective inhibition on *Lipomyces* strains grown on *Aspergillus* minimal medium.

Thus, 10 to 15 mg/L hygromycin B was used for *Lipomyces* transformation selection on YPD agar plates or liquid culture thereafter.

Example 4

Transgene Expression Cassettes for *Lipomyces* Transformation

Five different transgene expression cassettes were prepared for *Lipomyces* transformation (FIGS. 5A-5E). The pTef1-hph construct (FIG. 5A) expression cassette was prepared by yeast gap repairing with PCR DNA fragments (oligonucleotide pair SEQ ID NOS: 1 and 2 for *L. starkeyi* tef1 promoter and oligonucleotide pair SEQ ID NOS: 3 and 4 for hph) and sub-cloned into the T-DNA binary vector to generate the T-DNA binary vector pZD663-pTef1-hph (FIG. 5B), which only contains the bacterial hygromycin B phosphotransferase (hph) under the control of *L. starkeyi* translational elongation factor 1α (tef1) promoter. The function of transgene expression cassette was initially verified in *S. cerevisiae* grown on YPD with 75 mg/l hyg. Similarly, both transgene expression cassettes (FIGS. 5C, 5D) were prepared by yeast gap repairing and further sub-cloned into T-DNA binary vector of pZD663 or pZD663hph to form pZD663-5'-TrpC-pTef1hph-3'-trpC and pZD663hph-pTef1-GUS vectors, respectively. The transgene expression cassette for NADP-malic enzyme was prepared by Gibson assembly with T-DNA binary vector pZD663hph to form pZD663hph-pTef1-Me1 vector (FIG. 5E).

Example 5

*Agrobacterium*-Mediated Transformation

This example describes the results of transformation of *Lipomyces*, including *Agrobacterium*-mediated transformation.

Prior to using *Agrobacterium*-mediated transformation, LiAc-mediated transformation was attempted, based on reports in starkeyi NRRL Y-11557 (ATCC 58680) and *L. kononenkoae* strains (Calvey et al., 2014; Wang et al., 2011). A similar LiAc-mediated transformation protocol was used to transfer the pTef1-hph transgene expression cassette into the chromosomes of three *Lipomyces* strains (*L. starkeyi* NRRL Y-11557 & NRRL Y-11558 and *L. kononenkoae* NRRL Y-27504). The transformation protocol was evaluated by applying different amounts (1 to 5 µg) of intact or linearized plasmid DNA, total cells ($1 \times 10^7$ to $2 \times 10^8$), heat-treatment temperatures (38 to 42° C.), and incubation durations (15 to 30 min). However, no transformed colonies were obtained on 10 mg/l hygromycin B selection YPD agar plate after 5 to 10 days incubation at 30° C.

In addition, PEG-mediated protoplast transformation was attempted for the same three strains by using two linearized plasmid DNA (1 or 5 µg) concentrations in $2 \times 10^8$ protoplasts. Similarly, for electroporation transformation, 100 ng plasmid DNAs were mixed with $5 \times 10^8$ cells for treatment. After transformation treatments, no viable cell colonies appeared after 5-10 days incubation at 30° C. for both transformation methods.

Due to the failure of these methods, *Agrobacterium*-mediated transformation was examined. Five different combined ratios between *Lipomyces* cells and *Agrobacterium tumefaciens* cells containing tef1-hph T-DNA binary vector were prepared in the induction medium (IM) with or without addition of 0.2 mM acetosyringone (AS), which included four combined mixes (*Lipomyces/A. tumefaciens*: $5 \times 10^6/2 \times 10^8$; $1 \times 10^7/2 \times 10^8$; $5 \times 10^7/2 \times 10^8$; $1 \times 10^7/7 \times 10^8$). Acetosyringone is a natural secondary metabolite that is degraded from lignin compounds in plants, which can enhance *Agrobacterium*-mediated transformation.

These mixed cells were grown on IM agar plates with 0.2 mM AS except the combined cell mix of $1 \times 10^7/2 \times 10^8$ that was kept on the IM agar plate without AS. Various amounts of transformed cell colonies appeared on the YPD agar plates with 10 or 25 mg/l hyg (hyg10 or hyg25) and 250 mg/l cefotaxime (ceft250) after 3 to 5 days growth selection.

Figure 6A:
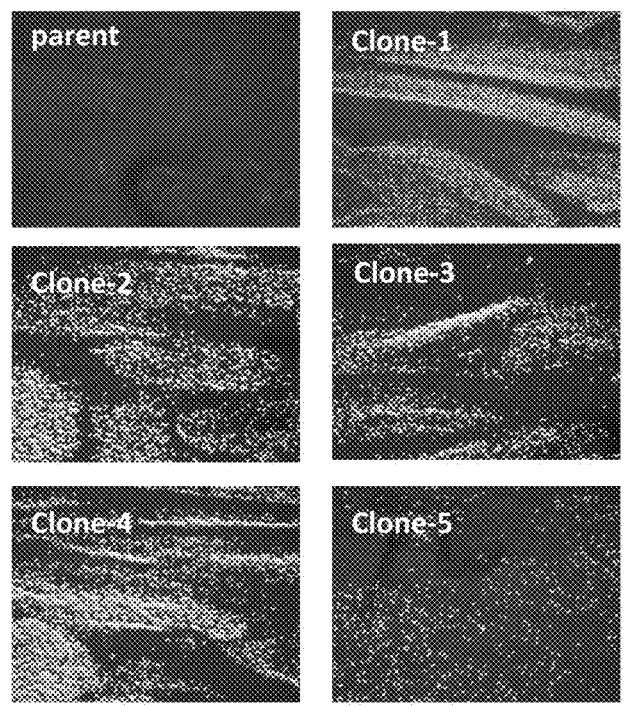
FIG. 6A is a digital image showing stereo microscopic images of parent *L. starkeyi* NRRL Y-11557 and the selected pTef1-hph transgenic strains grown on yeast-peptone-dextrose (YPD) medium agar plates with 10 mg/l hygromycin B at 30° C. for 2 days.
Figure 6B:
FIG. 6B is a digital image showing the PCR verification that the *Agrobacterium*-mediated *L. starkeyi* transformants contained the hygromycin B phosphotransferase (hph) gene.

Several transformed clones of *L. starkeyi* carrying pTef1-hgh transgene expression cassette (FIG. 5B) were grown on YPD agar plates containing both hyg10 and ceft250 with the parent strain as a control. After two days incubation at 30° C., transformed clones 1 to 5 were well grown on the antibiotic selection YPD plates while the parent was not able to grow on the same media (FIG. 6A). The genomic DNA was isolated from those selected transformants for gene integration confirmation by polymerase chain reaction (PCR) with oligonucleotide pair SEQ ID NOS: 29 and 30 corresponding to the hph coding region. As shown in FIG. 6B, genomic DNA PCR fragments corresponding to the coding region of hph gene were detected in all transgenic clones. Thus, the results of hygromycin B selection growth and PCR analysis confirmed that the hph gene was integrated into the *L. starkeyi* chromosomes following *Agrobacterium*-mediated transformation.

Example 6

Homologous Recombination in *L. starkeyi*

Figure 7A:
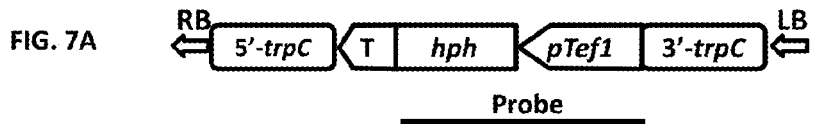
FIG. 7A is a schematic drawing showing the transgene expression cassette used for *Agrobacterium*-mediated transformation.

After successful transfer of the bacterial hph gene into *L. starkeyi* chromosomes via *Agrobacterium*-mediated transformation, the feasibility of gene homologous replacement at indole-3-glycerolphosphate synthase (trpC) gene locus was examined. The T-DNA vector containing the tef1-hph marker gene flanked with 2 kb DNA fragments of both 5'-upstream and 3'-downstream trpC gene (FIG. 7A) was used. The expression cassette in the T-DNA binary vector was mobilized into *Agrobacterium tumefaciens* EHA105, which was used to integrate the expression cassette into *L. starkeyi* NRRL Y-11558.

Over 100 transformed colonies were randomly picked and grown in 1 ml yeast synthetic drop-out medium without tryptophan (SC-trp, without tryptophan) and 10 mg/l hygromycin B and 250 mg/l cefotaxime in the wells of 2 ml×96-deep Whateman cell culture plate. The plates were incubated at 28° C. and 125 rpm for 3~4 days.

All transformants exhibited growth in the SC-trp liquid medium cultures or on the agar plates re-streaked from the liquid cultures, indicating that none had a homologous replacement occurred at the *L. starkeyi* TrpC locus and indicating the rate of gene deletion was significantly low in *L. starkeyi*.

Figure 7B:
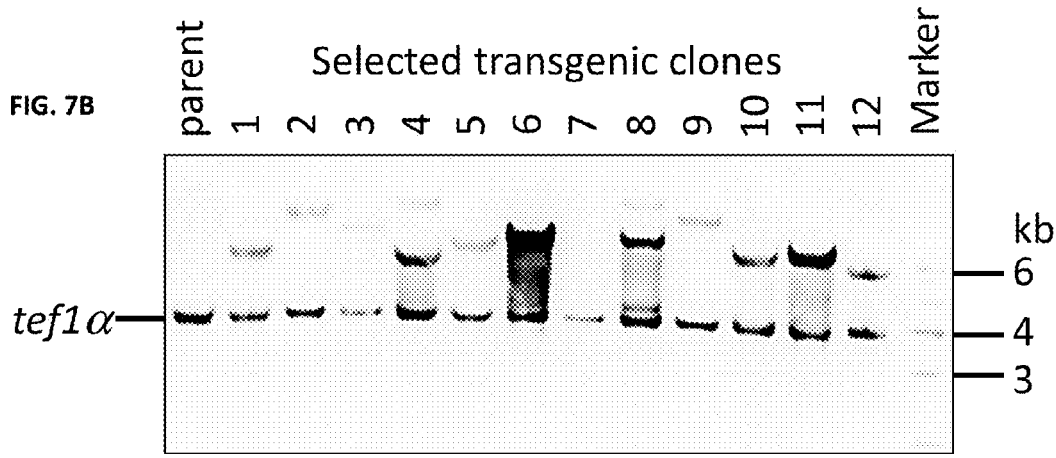
FIG. 7B is a digital image showing Southern blotting analysis demonstrating the hybridization of genomic DNA of parent and transgenic strains digested by restriction enzyme SacI with a biotin-labeled probe corresponding to both the tef1 promoter and the hph coding sequence.

Among those transgenic clones, 12 were selected to examine the transgene integration into *Lipomyces* chromosomes by Southern blotting analysis. For Southern blotting analysis of TrpC gene deletion, one microgram of total genomic DNA was digested with the restriction endonuclease SacI at 37° C. overnight. The genomic DNA fragments were separated in 1% agarose gel electrophoretically and transferred onto the GE Hybond-N$^+$ membrane with alkaline capillary transfer method. The 2.2 kb pTef1-hph marker gene fragment was used for preparation of the biotin-labeled probe. The Southern blotting analysis shows that the transgene fragment was inserted at different location of the chromosomes with one or two copies More than 66% of them had a single copy integration event (FIG. 7B).

Thus, the *Agrobacterium*-mediated transformation appeared to result in insertion of the T-DNA via an non-homologous integration.

Example 7

Evaluation of Five *Agrobacterium tumefaciens* Strains for *L. starkeyi* Transformation Different *A. tumefaciens* strains have different virulence strengths, and therefore, influence the transformation efficiency. The transformation efficiency of *L. starkeyi* strain NRRL Y-11558 with five different *Agrobacterium tumefaciens* strains (LBA1100, LBA1126, LBA4404, EHA105 and A348), which all contain a different disarmed Ti plasmid, were compared at the same conditions.

All five *Agrobacterium tumefaciens* strains were able to mobilize T-DNA (pTef1-hph transgene expression cassette) into the *L. starkeyi* with different efficiencies (Table 6). The *Agrobacterium tumefaciens* strain EHA105 exhibited the highest transformation efficiency among these five strains.

TABLE 6

The efficiency of *Agrobacterium*-mediated transformation in *L. starkeyi*

| | | *L. starkeyi* cells | | | | |
|---|---|---|---|---|---|---|
| | | $5 \times 10^6$ | $1 \times 10^7$ | $5 \times 10^7$ | $1 \times 10^7$ | $1 \times 10^7$ |
| | | *Agrobacterium* cells | | | | |
| *Agrobacterium* | Disarmed plasmid | $2 \times 10^8$ | $2 \times 10^8$ | $2 \times 10^8$ | $6 \times 10^8$ | -AS ($2 \times 10^8$) |
| EHA105 | pTiBo542 DT-DNA | 320 | 360 | 940 | 680 | 5 |
| A348 | pTiA6NC | 180 | 190 | 330 | 220 | 3 |
| LBA1100 | pTiB6 DT-DNA | 160 | 370 | 320 | 280 | 4 |
| LBA1126 | pTiB6 ΔT-DNA VirGI77V virA-TAR | 190 | 230 | 280 | 250 | 6 |
| LBA4404 | pTiAch5 DT-DNA | 180 | 330 | 340 | 170 | 8 |

Example 8

Analysis of tef1 Promoter Activity

Figure 8A:
FIG. 8A is a schematic drawing showing the β-glucuronidase (GUS) reporter gene construct used for *Agrobacterium*-mediated transformation.

The pZD663hph-pTef1-GUS-Ttef1 vector (FIG. 8A) was mobilized into the *A. tumefaciens* EHA105 by the freeze-thaw method. The *A. tumefaciens* EHA105 containing pZD663hph-pTef1-GUS-Ttef1 T-DNA binary vector was confirmed and used for *L. starkeyi* NRRL Y-11558 transformation. The transformed *L. starkeyi* cells were selected on YPD medium agar plates containing 10 mg/l hygromycin and 250 mg/l cefotaxime. The transgene expression cassette pTef1-GUS-Ttef1 was confirmed by PCR with SEQ ID NOS: 19 and 30 or 24 and 29. The confirmed transgenic *L. starkeyi* strains were grown in YPD or lipid production liquid medium culture (*Aspergillus* minimal medium modified with 80 g/l of glucose and 1.43 g/l of ammonium chloride) for different growth periods. About 2.5 to 5 ml of culture cells were pelleted in a floor centrifuge at 4,500×g for 5 min. The cells pellets were resuspended into 1 ml dH$_2$O and transferred into the microcentrifuge tubes and centrifuged at 15,000×g for 20 seconds. After dH$_2$O removal, the final cell pellets were stored at −80° C. until use or immediately sonicated, and analyzed as described in Example 1.

Figure 8B:
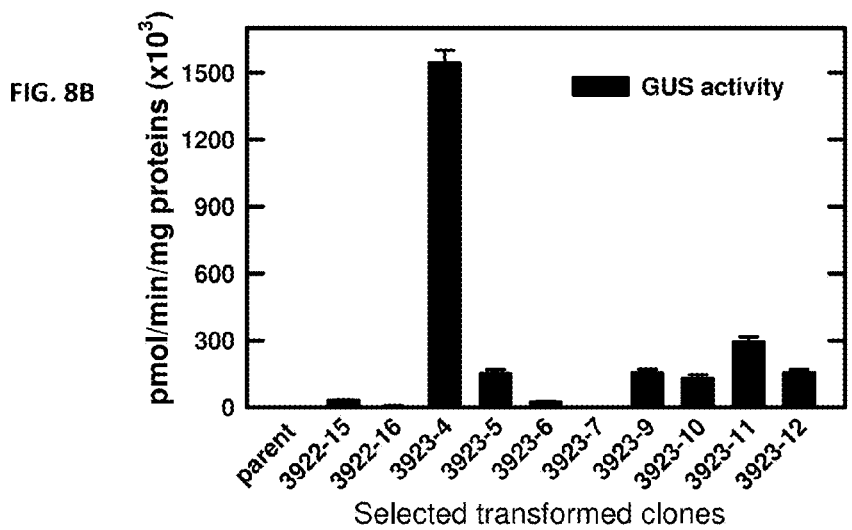
FIG. 8B is a bar graph showing β-glucuronidase (GUS) activity in the parent and selected transgenic strains of *L. starkeyi* that the GUS gene under the control of the tef1a promoter grown at 30° C. and 200 rpm for 3 days.

FIG. 8B shows the GUS activities in selected transgenic clones of *L. starkeyi*. GUS activity differed among those selected transgenic strains of *L. starkeyi*.

The time course of tef1 promoter activity was also determined by measuring GUS activity in transgenic clone 3923-11 during 6 days growth in lipid production culture conditions (FIG. 9).

The results show that the tef1 promoter remains highly active for at least 6 days, indicating that it can be used for overexpression of genes, such as those involved in lipid and chemical production.

Example 9

*Agrobacterium*-Mediated Transformation of Different *L. starkeyi* Strains and *Lipomyces* Species More than 65 different *Lipomyces* strains of genus *Lipomyces*, known for an unusual "fat-producing' ascosporic yeast from soil have been classified into 15 different species that include *L. doorenjongii, L. japonicus, L. Knockii, L. knononenkoae, L. lipofer, L. mesembrius, L. oligophaga, L. orientalis, L. Smithiae, L. spencermartinsiae, L. starkeyi, L. suomiensis, L. tetrasporus, L. yamadae*, and *L. yarrowii* (Kurtzman et al., 2007; Oguri et al., 2012; Smith et al., 1995).

*Agrobacterium*-mediated transformation was carried out in 11 different *Lipomyces* strains and species, which included five different *L. starkeyi* strains (NRRL Y-11557, NRRL Y-11558, NRRL Y-27943, NRRL Y-27944, and NRRL Y-27945) and six different *Lipomyces* species [*L. doorenjongii* (NRRL Y-27504), *L. kononenoae* (NRRL Y-11553), *L. lipofer* (NRRL Y-11555), *L. smithiae* (NRRL Y-17922), *L. suomiensis* (NRRL Y-17356), and *L. tetrasporus* (NRRL Y-11562)]. All strains were maintained on YPD medium agar plates at 30° C. Five single colonies from each strain were inoculated in 15 ml YPD liquid culture medium and grown at 30° C. and 200 rpm for 2 days except *L. lipofer* with slow growth that required at least 5 additional days of growth under the same conditions prior to *Agrobacterium*-mediated transformation. *A. tumefaciens* EHA105 containing the T-DNA binary vector pZD663-pTef1-hph was used for the *Lipomyces* transformation. The *Agrobacterium*-mediated transformation was executed as described above example 5. All cell mixtures were spread onto the sterile nylon membrane (2×3 cm) laid on the surface of pre-dried plates of induction medium agar and incubated at room temperature for 2 days for all strains except *L. lipofer* for 4 days. The transformed cells were selected on the YPD medium agar plates containing 10 mg/l hygromycin B and 250 mg/l cefotaxime except *L. suomiensis* with 20 mg/l hygromycin B and 250 mg/l cefotaxmine.

As shown in Table 7, all 11 transformed *Lipomyces* strains could be selected with hygromycin effectively on YPD agar plates with proper amounts of hygromycin B. Genomic DNA PCR amplification using the oligo pair (29/30) corresponding to the hph selection marker gene confirmed that all transformed *Lipomyces* strains carried the pTef1-hph transgene expression cassette. *L. starkeyi* strains NRRL Y-11557 and NRRL Y-11558, *L. knononenkoae* (NRRL Y-11553), *L. suomiensis* (NRRL Y-17356), and *L. tetrasporus* (NRRL Y-11562) had relatively higher transformation rates. In addition, effects of the secondary metabolite acetosyringone (AS) on *Agrobacterium*-mediated transformation in different *Lipomyces* strains varied.

Figure 11:
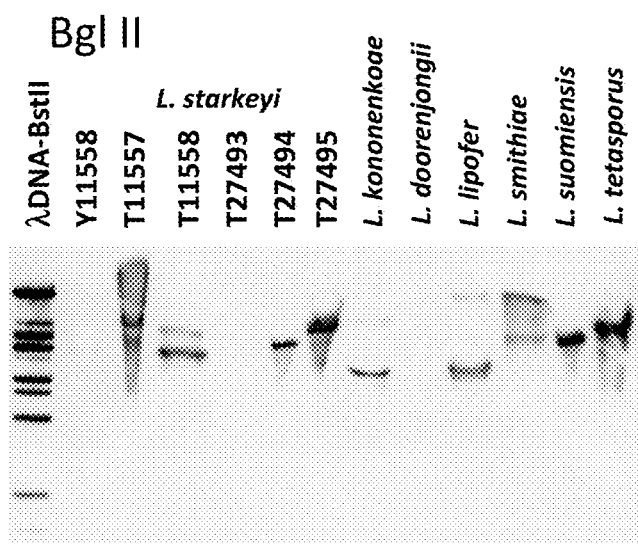
FIGS. 11A-11B show Southern blotting analysis of selected *Lipomyces* transgenic clones containing the pTef1-hph transgene expression cassette. (A) is the transgene expression cassette used for *Agrobacterium*-mediated transformation. (B) is the Southern blot of genome DNA digested with restriction enzyme Bgl II from parent and different transgenic *Lipomyces* strains. Y-11558 was the *L. starkeyi* parent strain for a negative control. The label T11557, T11558, T27493, T27494, and T27495 are for *L. starkeyi* pTef1-hph transgenic strains in *L. starkeyi* strain of NRRL Y-11557, NRRL Y-11558, NRRL Y-27943, NRRL Y-27944, or NRRL Y-27945. *L. kononenkoae; L. doorenjongii; L. lipofer; L. smithiae; L. suomiensis*; and *L. tetrasporus* are selected pTef1-hph transgenic strains for those *Lipomyces* species.

The hygromycin resistance of parent and transformed *Lipomyces* cells in a 1/10 series dilutions were compared on the same YPD agar plates with either 10 or 25 mg/l hygromycin B (hyg10 or hyg25, respectively) and 250 mg/L cefotaxime. The results in FIG. 10 show that all transgenic *Lipomyces* cells (T-) grew well on hygromycin selection condition, while the growth of their parent strains (Y-) were severely suppressed under the same culture conditions, indicating that pTef1-hph was expressed properly in the transgenic strains. The integration of pTef1-hph transgene expression cassette (FIG. 11A) was also confirmed by Southern blotting analysis which indicated 1 to 2 copies of the gene were inserted (FIG. 11B).

These results confirm that *Agrobacterium*-mediated transformation can integrate a transgene expression cassette into the genomes with properly functional expression in all selected *Lipomyces* species.

Example 10

Overexpression of NADP-Malic Enzyme for Improved Lipid Production

The NADP-dependent malic enzyme (ME1) is a key enzyme involving in NADPH production, which is required for lipid biosynthesis. In this example, the time-course ME1 activity was determined in six different transgenic strains grown in lipid production liquid cultures for 125 hrs.

The promoter region of the *L. starkeyi* tef1 gene and the coding and its transcriptional terminator regions of NADP-Malic enzyme gene were isolated by genomic DNA PCR from *L. starkeyi* using SEQ ID NOS: 25 and 26 and 27 and 28, respectively. The DNA fragments were fused together into the HpaI/EcoRI sites of T-DNA binary vector pZD663hph to form transgene expression T-DNA binary vector pZD663hph-tef1-Me1 (FIG. 5E) with Gibson Assembly cloning kit.

The pZD663hph-tef1-Me1 vector was mobilized into *A. tumefaciens* EHA105 by Freeze-thaw transformation method. The confirmed *A. tumefaciens* was employed for *L. starkeyi* NRRL Y-11558 transformation-mediated by *Agrobacterium* as described above. Fifteen individual transgenic colonies were picked grown in YPD medium liquid culture containing 10 mg/l hygromycin B and 250 mg/l cefotaxime for biomass production at 30° C. and 200 rpm for 2 to 3 days.

TABLE 7

*Agrobacterium*-mediated transformation efficiency in different *Lipomyces* cells

| | | Lipomyces cells | | | | | |
|---|---|---|---|---|---|---|---|
| | | $5 \times 10^6$ | $1 \times 10^7$ | $5 \times 10^7$ | $1 \times 10^7$ | $1 \times 10^7$ | $2 \times 10^7$ |
| | | EHA105 *Agrobacterium* cells | | | | | |
| Species | Strain No | $2 \times 10^8$ | $2 \times 10^8$ | $2 \times 10^8$ | $6 \times 10^8$ | -AS ($2 \times 10^8$) | $2 \times 10^8$ |
| *L. starkeyi* | Y-11557 | 920 | 2110 | 7460 | 770 | 10 | |
| | Y-11558 | 1980 | 2820 | 4730 | 2020 | 10 | |
| | Y-27943 | 0 | 30 | 170 | 10 | 0 | |
| | Y-27944 | 0 | 0 | 30 | 10 | 0 | |
| | Y-27945 | 20 | 20 | 150 | 0 | 0 | |
| *L. kononenkoae* | Y-11553 | 1300 | 1970 | 2770 | 1870 | 60 | |
| *L. doorenjongii* | Y-27504 | 70 | 100 | 1230 | 150 | 10 | |
| *L. lipofer* | Y-11555 | | 1120 | | 540 | 10 | 1170 |
| *L. smithiae* | Y-17922 | 60 | 50 | 300 | 60 | 12 | |
| *L. suomiensis* | Y-17356 | 490 | 1050 | 2280 | 3020 | 0 | |
| *L. tetrasporus* | Y-11562 | 1580 | 730 | 620 | 1030 | 20 | |

The transgenic *L. starkeyi* cells were used for genomic DNA preparation and PCR confirmation of the insertion of transgene expression cassette of hph-ptef1-Me1 in the chromosomes. The confirmed transgenic strains were streaked on YPD medium agar plates containing the same amounts of hygromycin B and cefotaxime for isolation of transformed single colonies.

The transgenic strains were streaked on YPD medium agar plate containing 10 mg/l hygromycin B and 250 mg/l cefotaxime for single cell growth and seed culture preparation in the YPD liquid culture. About $1 \times 10^6$ cells/ml of transgenic strains were inoculated, grown in lipid production medium liquid cultures at 30° C. and 200 rpm, and harvested at different growth periods, which used for NADP-malic enzyme activity assay as described in Example 1.

Figure 12:
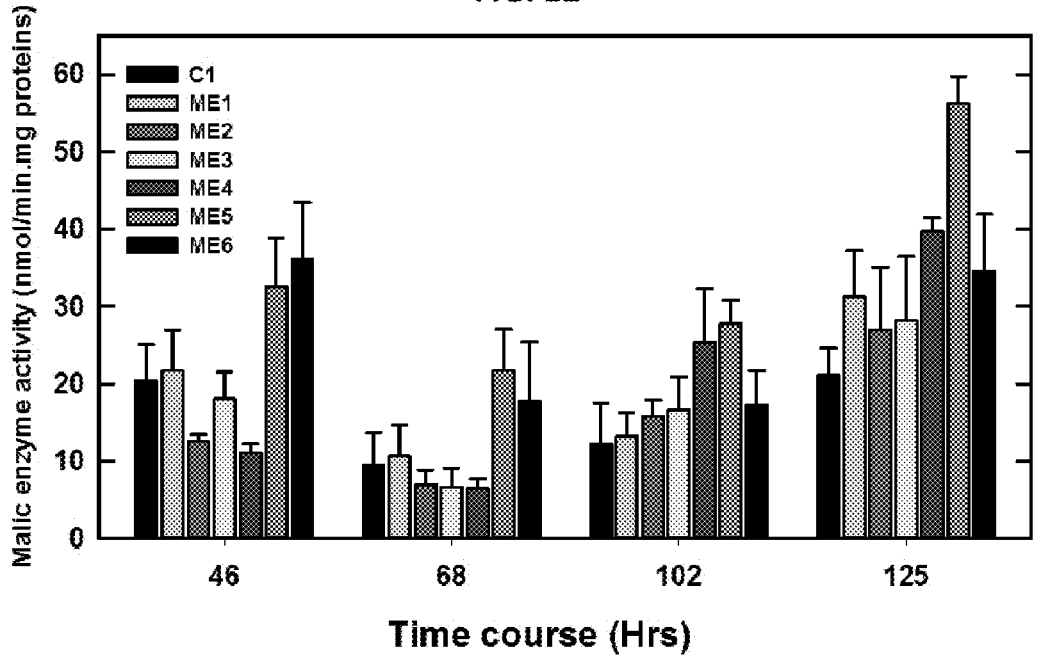
FIG. 12 is a graph showing the time-course NADP+-ME1 activities of parent and selected pTef1-Me1 transgenic strains grown in the liquid culture of lipid production medium at 30° C. and 200 rpm for 5 days. The data are average of four replicates.

As shown in FIG. 12, all transgenic strains exhibited much higher ME1 activity than the parent control strains at lipid production stages (102 to 125 hours). Transgenic ME5 and ME6 strains had much higher ME1 activity than the control strain during the entire culture period.

These results demonstrate that *Agrobacterium*-mediated transformation is an effective method for transfer exogenous genetic materials into the chromosomes of different *Lipomyces* species, which can be used for heterologous production of valued proteins or chemicals or improvement of lipid production.

REFERENCES

Beopoulos et al., (2009) *Progress in lipid research* 48: 375-387
Boulton C A, Ratledge C (1984) *Appl. Micro. Biotechnol.* 20: 72-76
Bundock et al., (1995) *The EMBO journal* 14: 3206
Calvey et al., (2014) *Current genetics:* 1-8
Carroll A M, Sweigard J A, Valent B (1994) *Fungal Genet Newsl* 42: 22
Christianson et al., (1992) *Gene* 110: 119-122
Colot et al., (2006) *Proc. Natl. Acad. Sci. USA* 103: 10352-7
Cullimore D, Woodbine M (1961) A Superior Fat-synthesizing Single-spore Strain of *Lipomyces*.
Dai Z, et al., (2013) *Fungal genetics and biology: FG & B* 61: 120-132
De Groot et al., (1998) *Nature biotechnology* 16:839-42.
Dellaporta et al., (1983) A plant DNA minipreparation: Version II. *Plant Molecular Biology Reporter* 1: 19-21
Gallagher S R (1992) *GUS protocols: using the GUS gene as a reporter of gene expression*: Academic Press.
Gibson et al., (2009) *Nature methods* 6: 343-345
Gill et al., (1977) *Applied and environmental microbiology* 33: 231-239
Hoekema et al., 1983. *Nature* 303:179-181.
Holsters et al., (1978) *Molecular and General Genetics MGG* 163: 181-187
Hood et al., 1993. *Transgenic Research* 2:208-218.
Jefferson R A (1987) *Plant molecular biology reporter* 5: 387-405
Jefferson et al., (1987) *EMBO J* 6: 3901-3907
Kurtzman et al., 2007 *FEMS yeast Res.* 7:1027-1034
Nester et al., (1984) *Annual Review of Plant Physiology* 35: 387-413
Oguri E et al., (2012) *Antonie van Leeuwenhoek* 101: 359-368
Orr-Weaver T L, Szostak J W (1983) *Proc. Natl. Acad. Sci. USA* 80: 4417-4421
Rattray et al., (1975) Lipids of yeasts. *Bacteriological reviews* 39: 197
Sitepu et al., (2014a) *Biotechnology advances*
Sitepu et al., (2014b) *Biotechnology Advances* 32: 1336-1360
Smith et al., 1995 *Antonie van Leeuwenhoek* 68: 75-87
Soltani J, van Heusden G P H, Hooykaas P J (2008) *Agrobacterium*-mediated transformation of non-plant organisms. In *Agrobacterium: from biology to biotechnology*, pp 649-675. Springer
Starkey R L (1946) *J. Bacteriol.* 51: 33
Streekstra H (1997) *J. biotechnology* 56: 153-165
Thevenieau F, Nicaud J-M (2013) *OCL* 20: D603
Van Rensburg et al., (1995) *Systematic and applied microbiology* 18: 410-424
Wang et al., (2011) *Biotechnology letters* 33: 1993-1998
Yu et al., (2004) *Fungal genetics and biology: FG & B* 41: 973-981

In view of the many possible embodiments to which the principles of the disclosure may be applied, it should be recognized that the illustrated embodiments are only examples of the disclosure and should not be taken as limiting the scope of the invention. Rather, the scope of the disclosure is defined by the following claims. We therefore claim as our invention all that comes within the scope and spirit of these claims.

We claim:

1. A method of transforming *Lipomyces* sp. cells, comprising:
   incubating the *Lipomyces* sp. cells in culture media for at least 24 hours at 20 to 35° C. thereby producing *Lipomyces* sp. cells at an exponential growth stage, or at least 24 hours at 25 to 35° C. thereby producing *Lipomyces* sp. cells at a bud-growth stage;
   incubating the *Lipomyces* sp. cells at the exponential growth stage, the bud-growth stage, or both with *Agrobacterium* sp cells,
      wherein the *Agrobacterium* sp. cells comprise a T-DNA binary plasmid,
      wherein the T-DNA binary plasmid comprises a first nucleic acid molecule encoding a first protein and a second nucleic acid molecule encoding a selective marker that permits growth of transformed *Lipomyces* sp. cells in selective culture media comprising an antibiotic;
   allowing the first nucleic acid molecule and the second nucleic acid molecule to integrate into a chromosome of the *Lipomyces* sp. cells; and
   incubating the *Lipomyces* sp. cells with selective culture media comprising the antibiotic and optionally with an antibiotic that substantially reduces growth of the *Agrobacterium* sp. cells.

2. The method of claim 1, wherein the method allows the *Lipomyces* sp. cells to express the first protein and the selective marker.

3. The method of claim 1, wherein prior to transformation, growth of the *Lipomyces* sp. cells is significantly reduced in the selective culture media comprising the antibiotic relative to an amount of growth following transformation and expression of the selective marker nucleic acid molecule by the *Lipomyces* sp. cells.

4. The method of claim 1, wherein the antibiotic that substantially reduces growth of the *Agrobacterium* cells is cefotaxime.

5. The method of claim 1, wherein the culture media comprises synthetic complete (SC) or yeast extract-peptone-dextrose (YPD) media.

6. The method of claim 1, wherein the antibiotic is G418, hygromycin B, pyrithiamine, phleomycin D1, blasticidin, basta, gentamicin, N-glycosyl-polifungin or combinations thereof.

7. The method of claim 1, wherein the antibiotic is hygromycin B and the selective marker nucleic acid molecule is hygromycin B phosphotransferase (hph).

8. The method of claim 1, wherein the first nucleic acid molecule comprises one or more nucleic acid molecules involved in fatty acid synthesis or degradation.

9. The method of claim 1, wherein expression of the first nucleic acid molecule and or the second nucleic acid molecule is controlled by a constitutive promoter.

10. The method of claim 9, wherein the constitutive promoter is an *L. starkeyi* translational elongation factor 1α (tef1) promoter or an *L. starkeyi* ura3 promoter.

11. The method of claim 1, wherein the *Lipomyces* sp. cells are *L. arxii, L. doorenjongii, L. japonica, L. knockii, L. knononenkoae, L. lipofer, L. mesembrius, L. spencer-martinsiae, L. oligophaga, L. orientalis, L. smithiae, L. spencermartinsiae, L. starkeyi, L. suomiensis, L. tetrasporus, L. yamadae,* or *L. yarrowii* cells.

12. The method of claim 1, wherein the *Lipomyces* sp. cells are *L. doorenjongii* strain NRRL Y-27504, *L. kononenoae* strain NRRL Y-11553, *L. lipofer* strain NRRL Y-11555, *L. smithiae* strain NRRL Y-17922, *L. suomiensis* strain NRRL Y-17356, *L. tetrasporus* strain NRRL Y-11562, *L. arxii* strain NRRL Y-17921, *L. japonicas* strain NRRL Y-17848, *L. kockii* strain NRRL Y-2750, *L. lipofer* strain NRRL Y-1351 or NRRL Y-6333, *L. mesembrius* strain NRRL Y-27927, NRRL Y-27928, NRRL Y-27929, NRRL Y-27930, or NRRL Y-27931, or *L. spencer-martinsiae* strain NRRL Y-7042.

13. The method of claim 1, wherein the *Lipomyces* sp. cells are *L. starkeyi* cells.

14. The method of claim 13, wherein the *L. starkeyi* cells are strain NRRL Y-11557, NRRL Y-11558, NRRL Y-27943, NRRL Y-27944, NRRL Y-2750, or NRRL Y-27945.

15. The method of claim 1, wherein the *Agrobacterium* sp. cells are *Agrobacterium tumefaciens* cells.

16. The method of claim 15, wherein the *Agrobacterium tumefaciens* cells are strain LBA1100, LBA1126, LBA4404, EHA105 or A348.

17. A recombinant *Lipomyces* sp. cell generated using the method of claim 1, wherein the cell comprises the first and second nucleic acid molecules.

18. A method of producing a product comprising:
    culturing the transformed *Lipomyces* sp. cell of claim 17 under conditions in the selective culture media that permit expression of the first nucleic acid molecule and the selective marker nucleic acid molecule; and
    producing a product directly or indirectly from the first nucleic acid molecule.

19. The method of claim 18, further comprising isolating the product from the selective culture media.

20. The method of claim 1, wherein the incubating the *Lipomyces* sp. cells with *Agrobacterium* sp. cells is at room temperature.

21. The method of claim 1, wherein the incubating the *Lipomyces* sp. cells with *Agrobacterium* sp. cells is at 20° C. to 28° C.

22. The method of claim 1, wherein the incubating the *Lipomyces* sp. cells with *Agrobacterium* sp. cells is for at least 24 hours.

23. The method of claim 1, wherein the incubating the *Lipomyces* sp. cells in culture media is for at least 30 hours at 28° C. to 32° C.

24. The method of claim 1, wherein the incubating the *Lipomyces* sp. cells in culture media is at 30° C.

25. The method of claim 1, wherein the incubating the *Lipomyces* sp. cells in culture media is for at least 48 hours.

* * * * *

SEQUENCE LISTING

```
<160> NUMBER OF SEQ ID NOS: 47

<210> SEQ ID NO 1
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 1
gtaacgccag ggtttccca gtcacgacgg tttaaacacc attaagattc actgtccttg      60

<210> SEQ ID NO 2
<211> LENGTH: 60
<212> TYPE: DNA
<213> ORGANISM: Artificial sequence
<220> FEATURE:
<223> OTHER INFORMATION: Synthetic oligonucleotide
```

<400> SEQUENCE: 2
tttgccggat cggtctgcta acagcttact tctacaggga cctgaactca ccgcgacgtc    60

<210> SEQ ID NO 3
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 3
gacgtcgcgg tgagttcagg tccctgtaga agtaagctgt tagcagaccg atccggcaaa    60

<210> SEQ ID NO 4
<211> LENGTH: 57
<212> TYPE: DNA
<213> ORGANISM: Artificial sequence
<220> FEATURE:
<223> OTHER INFORMATION: Synthetic oligonucleotide

<400> SEQUENCE: 4
gcggataaca atttcacaca ggaaacagcg tttaaaccgg tcggcatcta ctctatt       57

<210> SEQ ID NO 5
<211> LENGTH: 57
<212> TYPE: DNA
<213> ORGANISM: Artificial sequence
<220> FEATURE:
<223> OTHER INFORMATION: Synthetic oligonucleotide

<400> SEQUENCE: 5
gtaacgccag ggttttccca gtcacgacgg agctcagatc agcatctatc gctcgat       57

<210> SEQ ID NO 6
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 6
aggaatagag tagatgccga ccgagtgtgg gaggcaacca at                       42

<210> SEQ ID NO 7
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 7
attggttgcc tcccacactc ggtcggcatc tactctattc ct                       42

<210> SEQ ID NO 8
<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 8
tctggcttta cccaatcagc tagatatcgg gccatcaggg at                       42

<210> SEQ ID NO 9

<211> LENGTH: 42
<212> TYPE: DNA
<213> ORGANISM: Artificial sequence
<220> FEATURE:
<223> OTHER INFORMATION: Synthetic oligonucleotide

<400> SEQUENCE: 9
atccctgatg gcccgatatc tagctgattg ggtaaagcca ga                42

<210> SEQ ID NO 10
<211> LENGTH: 58
<212> TYPE: DNA
<213> ORGANISM: Artificial sequence
<220> FEATURE:
<223> OTHER INFORMATION: Synthetic oligonucleotide

<400> SEQUENCE: 10
gcggataaca atttcacaca ggaaacagcg tttaaacagc tatggagagc ggacttgt    58

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
ggacaacatc tcaagtctgc                                         20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
tctcaagtct gctgttcagc                                         20

<210> SEQ ID NO 13
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 13
cgtcgcggtg agttcaggca tgttgaattt agggatatac tgtag             45

<210> SEQ ID NO 14
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 14
ctacagtata tccctaaatt caacatgcct gaactcaccg cgacg              45

<210> SEQ ID NO 15
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 15

```
ctgcccttca ctcatcaatt accaacggtc ggcatctact ctatt          45

<210> SEQ ID NO 16
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 16
aatagagtag atgccgaccg ttggtaattg atgagtgaag ggcag          45

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
aaggagacct ggagtatctc                                      20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
gcaacgagtt catgcttgag                                      20

<210> SEQ ID NO 19
<211> LENGTH: 56
<212> TYPE: DNA
<213> ORGANISM: Artificial sequence
<220> FEATURE:
<223> OTHER INFORMATION: Synthetic oligonucleotide

<400> SEQUENCE: 19
gtaacgccag ggttttccca gtcacgacgt ttaaacagat atcgggccat caggga   56

<210> SEQ ID NO 20
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 20
gttgggsttt ctacaggacg taatccctgt agaagtaagc tgttagca       48
```

Note: SEQ 20 reads: gttgggttt ctacaggacg taatccctgt agaagtaagc tgttagca

```
<210> SEQ ID NO 21
<211> LENGTH: 48
<212> TYPE: DNA
<213> ORGANISM: Artificial sequence
<220> FEATURE:
<223> OTHER INFORMATION: Synthetic oligonucleotide

<400> SEQUENCE: 21
tgctaacagc ttacttctac agggattacg tcctgtagaa accccaac       48

<210> SEQ ID NO 22
<211> LENGTH: 45
<212> TYPE: DNA
```

<213> ORGANISM: Artificial sequence
<220> FEATURE:
<223> OTHER INFORMATION: Synthetic oligonucleotide

<400> SEQUENCE: 22
acttcttgga agccttgatg gctattcatt gtttgcctcc ctgct                45

<210> SEQ ID NO 23
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 23
agcagggagg caaacaatga atagccatca aggcttccaa gaagt                45

<210> SEQ ID NO 24
<211> LENGTH: 56
<212> TYPE: DNA
<213> ORGANISM: Artificial sequence
<220> FEATURE:
<223> OTHER INFORMATION: Synthetic oligonucleotide

<400> SEQUENCE: 24
gcggataaca atttcacaca ggaaacagca agcttactgc gttcattgct gtgact      56

<210> SEQ ID NO 25
<211> LENGTH: 41
<212> TYPE: DNA
<213> ORGANISM: Artificial sequence
<220> FEATURE:
<223> OTHER INFORMATION: Synthetic oligonucleotide

<400> SEQUENCE: 25
ccgcagatct gagctaccat taagattcac tgtccttgat c                    41

<210> SEQ ID NO 26
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 26
tacagggagc tcctaaatcg tcgactcg                                   28

<210> SEQ ID NO 27
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 27
ttaggagctc cctgtagaag taagctgtta g                               31

<210> SEQ ID NO 28
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 28
agcagacttg agatgcccgt cctggttctg gacc                            34

<210> SEQ ID NO 29
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 29
gtacttctac acagccatcg gtcca                                         25

<210> SEQ ID NO 30
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 30
cgttatgttt atcggcactt tgcat                                         25

<210> SEQ ID NO 31
<211> LENGTH: 1177
<212> TYPE: DNA
<213> ORGANISM: Lipomyces starkeyi

<400> SEQUENCE: 31
cagatatcgg gccatcaggg atgagtggat ataatatatt aatagtgtga attaggaata    60
gagcagagga gatgttgttc tcacagcatc actaatgcat agcacaagaa tgcggagaaa   120
tcgcctgtcc gcctggggca aggggaagcc tccgatagta tcattgacca gctgagccga   180
ccctgagtcg atagagtttt ggcgtgtggt caatattcag gtggggccga gcccttcgct   240
aagcctcatc tattaacttt ccttattcgg tcagggcttg agcactgcca gctaaacccc   300
acatattaca tcctaaccct gggcaataaa cagtcacagc ccatatgtgt ggctgtgcga   360
gtgcggaacg tgtcagctcg tgaagcacat ggagtgcgaa caggagttag acgacaccgc   420
acatggaaat tagggctgta tcgacacttt attgccaccg ccacgacggc aaattgtggt   480
cgctgtatcc gcaaagggga ggccggcctt gtcagtggtc agcaatgtag aatagacgta   540
gctggtggtg gacaggctaa ccatggggac agtcgatctg cattagtggt ccactgaggc   600
accgggaaga caaagacaaa aaaatgcgga cgaaaaacat tgacgtcagc caaatccgag   660
cgatgtttac gacttccctt gtcgggcacc ggctagttaa tgcaaagtgc tggcataagt   720
gcgcaaacgc aagcgcggta cgtgcgctga gcgtagagta aaaaaaattt tcttagccgc   780
gagcctagca acggcgccag gccgtatctt tctataaagc tctgcttcac ccgccacaat   840
ttccattcct tttcttcttt ttttctttgt ctactcacac ccgaaatcat agcatttcca   900
tctgagtatc tttaatctta atcacatcca tccacttatc ttttatacat cctctttaat   960
ctttcaaaat ggtatgttcc ttttttttgaa ttggatcgga ttctcgtggc gatcagttgg  1020
gacaataggc acggctctta tcagtgataa tgtgtcttca ttattgtgcg cctgactgta  1080
atctgttacc aattgagatt gcctgtttta aacccagaaa tcgtataaca atttctattt  1140
gccggatcgg tctgctaaca gcttacttct acaggga                           1177

<210> SEQ ID NO 32
<211> LENGTH: 1097
<212> TYPE: DNA
<213> ORGANISM: Lipomyces starkeyi

<400> SEQUENCE: 32

```
ctctcttgaa cgcatcaatt gcagtgttta caaaaagctc gtttgaaatg ccgatattcg      60
agacaggaga tctaacgctc tgaacaccag gtccctcaac aacttcgatg ccgctatcca     120
cgctatgatg cagcaacttg acaacatct caagtctgct gttcagcaac atcgtgccat     180
ggtggtacgc tttgcccctc tgcaacttat aagcagaccc gcttacttta cgggcattct     240
ggtcaacaat gtcgtgccgt tcattgacgc tgagtaccgt ttcttctcct ctttgcttaa     300
atactggatt cagtgctgtg cataacaata atgcatgctc atccctatca aatgagttgc     360
cgggcatcat gactgagtaa ttgacgttgc cttcatcgtg aaatacagtt cctcctccgg     420
attttcggcg gatgagcggc accttgtgcc tgcgcaatga ttgcacattt gtctctcgcc     480
aagggttctg gttccggcct atgatcactg agcgatagtt cgtgtacaag aataaaacct     540
ttttggataa ttgagtactt gaggcactat agctcgtaca agctgggaac ttttgaata     600
ggtagtcctc gtaagagaga ttgaaatatg gcgaacgaga ccgcgatatg tagacctcca     660
tgtcgtatag cttcttccgt ttcgaagttg tcgaactatt tgattggaga cggaaactga     720
agctgaaagg tgaggcagtt gtatctgtgt tgttattcct ccggaaggcg ctgagacgga     780
agtccgtgaa gctagcaagt gcgcgccgag cttctagcga cttcatggcg gtggtagatc     840
caaataatag acacgcatgt aatttcggat ttatatcatt ttttggcgac ggtcaatgtc     900
gtaactgata tatttctgca tttcgtctag ttagtacttg tacatagctg atctggctca     960
gggtccactg aaagtttagt ggctgggagg aatcacaggc gacaaaaaaa ttcactcctg    1020
ttcattttgg ctcagacttc gtaacatcac tcgacctcag ttcttgtctt ctacagtata    1080
tccctaaatt caacatg                                                   1097
```

<210> SEQ ID NO 33
<211> LENGTH: 1120
<212> TYPE: DNA
<213> ORGANISM: Lipomyces starkeyi

<400> SEQUENCE: 33

```
caaagccaga aaagttaaag gacgcaagag gagaggtggc aagcacaagg gagctattaa      60
agccgctgcg gaacacgaga ctgccaagga ggagccaatg tccattttcg caactatcat     120
gagtttgttt ggatttggtt ctgatggcac gtacatcaca tatgttgtta tcgcgttgtt     180
cgccgcctta cttatcgtgt ctctttggct gatattcagt ggcggaaaga aagataagat     240
aagtagatgg gatacattgt gggacatgga agaacagagc ctatgggagt ggctcgaaga     300
tcgcacaggt cacgtcggcg ccgctatggg tacgaaatcg cactcaaata gtacacctgt     360
gcgttcaaaa ggctggctta gtagacgtga gattgaggaa gcgattcaaa tcacgcaaca     420
acgacttgac ctactgagaa aaaaaatgga gaattatgag ggataatttt tgagttcgtt     480
catgtggtca tcgtgtgtat tacttcattt atttttgggat tgtcaatgtt ggtattttc     540
agtacatatg gtgtctaatt tgttaatggt atttttacc ccatatatct atctaatgga     600
gttgtacact tgataccaga aaattcattg ccgcatggcc tgcggcgttg tccacgaact     660
ttaacgttag cggtggtatc ttagactgca tggaggggaa taaggctgta aatgtggcag     720
tgttcttggc tcaaacgcac gctggatgat atttattgcc gaccaagact tgcaatgaac     780
cttgtacgcc gtcaaatgta gtatcgtttt cttggcgtat tagttaggat gtcgtaaaga     840
acgcagataa ctacgagata ttttaacatt aacagaatga taatctgtta ggctagagtg     900
ttcgtcggcc cggatgctac aactatgttt cgccccgggc acattgagtt aaggttcgac     960
```

```
gggactgatt tttatgactc gaacaaattg gttgcctccc acactgttga acacaacacg    1020
cactttctcg cacattttgg ttgtttaatg gtgtactgat caaagtcata tacagaaagt    1080 ggattttttga ctttaaattc cttagagcga gtatacaatg                         1120
```

<210> SEQ ID NO 34
<211> LENGTH: 1200
<212> TYPE: DNA
<213> ORGANISM: Lipomyces starkeyi

<400> SEQUENCE: 34

```
tggatcagga tgtttgtgca tcgggcctgc ggaaatgtgt ggctacgatt cgttgttggt     60
tgatctgttg ctaatgaatc cgtaggttct cagcgctatc gacagctatc cagtatatca    120
tttgcagaag ttttaaattt cccaagtcgg tcggccgaga ttgacatccc gcttggaaaa    180
ggagagtatg atgcgccttt gggtgttgag ttgttagtcg ctgtcatgaa ttcggagcga    240
atagatgtcc tagagcgaca gtttggtagg aaagatgacg agttcgactt tatacaacaa    300
tttttacgca cagtgttgct caaacgtaag cacagcctca actttgaata cgaagtgttt    360
ctgcttaata gctaatgcat acaagatggc gcagccctag tatacctatc ctctgagtcg    420
aagtcgctat tccctttact tttctatctt ctttcgccat cactactatc ggaacactct    480
agaaatatat tgatcgaagc atccaagaat atacaaccaa acgtcgtgga ccgggacgct    540
ctactgattc cttcaggatg ggactcatgg tccaaaatac tacttatcaa ggaaggattt    600
gatgttgaag gggtttcatc aggatggtca actgatgtac taagcaatga atgtgatatg    660
gaaggtataa ttgaggttta tgaggatgtc gtacatgcat ttggaggtcc acctggtggt    720
gcaaacggga acgaaatgtc gcaggaagag ctcgagattc gtagcactac cgtccaagag    780 ttttttgaaag gccaattggc cgatcttaat agcatagaag taagctaaga gtatgtagta    840
atagaattcg gtgaccatct gtttcttact taaccaataa ccctaacctc tcgtcatcat    900
cagcatcggt ctgaagagcg cgcatgctga gaagtacaca atgtagcact ttatcatcat    960
gcttttccgc attttttttc tctctccctc ggatcagtca gcggctcagg attaccgtgt   1020
cttcgttcca cgcttgcatc cattttttat agttccctga ccgattcgaa atagttcaca   1080
atgggtatgt tgcttgctt tttgaatctt ttgtgtacta gaccgccaat gactgaagtt    1140
tggccgtcaa agtccgatga tgaccaaagt agctaactct ggcattattt ccgtatagtt   1200
```

<210> SEQ ID NO 35
<211> LENGTH: 1150
<212> TYPE: DNA
<213> ORGANISM: Lipomyces starkeyi

<400> SEQUENCE: 35

```
ggagtgtccg acatcgtaaa ggacgacaaa ggggacgaca caatcacatt gacggacgaa     60
cgggccgctg aggtcgccag gactatagaa tcagatactg gcttagtggt cggtatcgaa    120
gcggatcctg accggccgga ctggcacgat tggtacgctc ggcgggtgca gttctgccag    180
tggacgattc tggcaaagag aggacatccc gctgtcttgc ggatcgtgtc gcacattacg    240
acagaaacgt tgcgcagaaa agttaccggt accctcgatt tgccaaagag taaagatgct    300
ggatcgcaga tcatgaattg gaccggtcct ggtatctgga ccgacacgat tttcgagtac    360
ttgtccgata ttcaagtgga tacggactgg cacaacgtta ccggcatctc gcgaggaaag    420
gttattggtg acgtcgtgat cctcccgatt acgtccttca gtccaggcgt cggcacaatg    480
```

| | |
|---|---|
| ggcgccaatg gcccagaaca tccacatgcg ttcgtctatc atatattcga aggctcctgg | 540 |
| aagcccgcga atgagcgcaa tattggcggc taattaaccc attattccgc agtccttttt | 600 |
| tgtacatttt agcttatata tattccattt tccagtagtt actaatttgg gaataatcgg | 660 |
| ttatcattat cgcgcttcgg gatcggtact tgcgctttaa acatacatac ctaataggct | 720 |
| ttttgcgtta ggtgacgtga attctatatt tgggtttggg cggggcttga aatatcacct | 780 |
| gggtttcggt tggtggattt acttctggat aaagtttggt attagatgct tcacgtagtg | 840 |
| gtatatgaaa cgaaaagtgc gggccggctt gttgatagcg cttgtatata tgtataataa | 900 |
| acttctagtt gttactaaga gcgagtgact atgtttggag ttaatcggaa atgtggtggg | 960 |
| tactacacat ctctagaaga cccattaata cgaggtgctt gtgcacagcg ctgcgcgttt | 1020 |
| gcccaacgaa acgcgtacct gaacgtgatc attaccgcat cacaacatca ccaccacagt | 1080 |
| caatcgccag taaaacacca cacgattctg taatcgaatc cagcaagcgc acattttcac | 1140 |
| ggcggcgatg | 1150 |

<210> SEQ ID NO 36
<211> LENGTH: 1351
<212> TYPE: DNA
<213> ORGANISM: Lipomyces starkeyi

<400> SEQUENCE: 36

| | |
|---|---|
| tctgctgcgt cacttctcgc cggagaatat gatggacttg ttgaagcagg ctgtggtgtt | 60 |
| caagaagtac atcaagggca tcggcatgag ttcgagcgag gcaggatgcc caccgtcgct | 120 |
| gtatgttgat attttcaagt ttgcgaagga gcagggctgg cacgttacat ctcatgctgg | 180 |
| cgagatcggt ccgccagagt acgtcagaga ctcgattgaa cttctcggca ttgaacgctg | 240 |
| tgaccacggt atcggtgcgc gaacagaccc gaagtggtc aagcttctcg ccgataagaa | 300 |
| ggtcggggtg actatgtgtc cgatttcgaa cgtcttgctg aaggttactg agtctattcc | 360 |
| gtactcgccg attcgacagt atcttgatgc caattgcaaa atctgcttca acagtgacga | 420 |
| tccatcttac tttggcagca catatatcga ggagaattac gacgcagttg agaaggagat | 480 |
| gggactcagc gttgccgagt gggtgaagat tgctcaggat gctattgata tgagctgggt | 540 |
| tgaggaagat gagcgcaaga agttgcagga cgagcttgat gctgttaagc tgaagtacaa | 600 |
| gttgaaggag ttgtatggta ttgaatagat gtacagtgag acagattgta ttttattgat | 660 |
| gatgacgatg acgatgacga tgacgatgat gaagatgaat acaagtcct gctgtcctac | 720 |
| caaagtcgac actgctaaga acgccagaga tattcagggc cacacacaag gctcagtatg | 780 |
| tatctgaaag atggtctgca aaccctagcc ctgaaattcc tattgctact cgacgcgttt | 840 |
| gggtaagagg gtcaggtggc ttagcagatg aacaagccag attaaaccgc gacgaaatat | 900 |
| gtgacgcaaa gtgttcgaaa tttggcaacg ttttctgag ttttggcagt ctgctcgaga | 960 |
| gtgcccgctg attcgccagc accgcacctc ccgcacgctc tcaggctact gttgatgcgt | 1020 |
| ttaattttt gatgatgcgg caggtaagct gtggtgttag ttaatgcaat gcgctgggcc | 1080 |
| tgttgatgga tctcgctcac tcccacttat aaatacccac gcacccccctc gtgccggcac | 1140 |
| ttatattcgt tctcttttgc cacacaacct tctgcgcata ttctcgcctc ttggactctg | 1200 |
| tttattctgt ccatccagtc gtattttatc aatcttttta tttcctgtag taaagcatgt | 1260 |
| ctgggtaggt ttatctcatc gtttggatgc catctaaggc gactttgaat tttggagtat | 1320 |
| gtggtgctaa cggggttgtt ttgattgcag a | 1351 |

<210> SEQ ID NO 37
<211> LENGTH: 1096
<212> TYPE: DNA
<213> ORGANISM: Lipomyces starkeyi

<400> SEQUENCE: 37

```
cgcatcatgt ctttgaattt ttcctccgtg ataggacgcc cggaataacct ggcctcttcg      60
taggcatcga tgaatcgatc tcccagcacc tcgtcgaagt tgacatagcg ccttaaatat     120
gatgcgtatt ccttccagga catgcatgct ttgcgacgca gtgccggatg taaactcgac     180
gcttttattt ccagcaattt ggcgctttcg atcaagactt ccaggtacgg tacttgcggg     240
aaatcgaact ccgaatgcgg gggcggcaaa ccaggatgcg aaacattatc tgacggttga     300
agggattcct ggatcattcg gcaccggatt aattccgctt cgatggtact tgcacatctt     360
tttgaaaagt cctgctcacc agggacgtat cgtttgggaa tatctgataa cgcgacccga     420
acgttgtaga gtctgtttag atagaggatc agcgcaacga gaccgactgt gaaatacatt     480
gctgcgatga taatgatgtt gaatatttgt tcgtttcgga gtgcctgcga gatcatatcg     540
gctggagtaa caatgacgaa accgcacgtg aagaagatga ggaggaataa gctacatcgg     600
tagagaaacc gggcccaccg gtcggacaac agactgtgat gcgacgacat attcagatag     660
cggcagtacg tcttaaaaaa agactgcagg attgtgctat atcgctttga gatggcaatg     720
catctaatcc ttgaatactg cgtttggtta caactctgga cagaacaaag tcacgaatct     780
ggcgggactg agattgaagc gcgtctccaa actttaattt ctggttgcac cctaacccaa     840
attcaaatcc gggtaatcaa gagccaaaat agctagggtg taaccctacg aaagcagtca     900
catcaaagtg cggcaccagg ctcaggtcta tctccaaaag ctttaaggtc tcgtagaaac     960
ttattctgct tttgattcag tgttgactaa aacgatcaga aagaaggtgc gatagtttga    1020
ttgatatgtg agaagtcggt actaataatc attagcattg tctcgcacat ttgccgacta    1080
gtcgttcgtt gtcatg                                                     1096
```

<210> SEQ ID NO 38
<211> LENGTH: 1290
<212> TYPE: DNA
<213> ORGANISM: Lipomyces starkeyi

<400> SEQUENCE: 38

```
ttattatggc atctataaga ttcttgagga ggccgatatc aaaggaaaga acgcggcgaa      60
ctggtatacc attaaaatac ttgatgacat atgaatgagt ctgatgaata atttaggatc     120
attaatgaca tactgggaat cgtgccggta ggcgaggaga agctactacc cagcgtcgtg     180
actccatcgc ggctcgccga cctgattatt gcccagaagc aaaagacaat taccagtaag     240
tgctaacgtt caagctggaa tctgggccgt tagtactgac agtatcagaa attattgcta     300
tgaatgtcat aaaatatttt cttcagaatc agggagacca tcgagcgacc gcagaagtga     360
tcgatcagta ccaattgacc gccatgggag acagcaatat tctggaggct atctgctcaa     420
atgtattaga ggagcacagc gatctagttg aactggtagt tcaggcaag aagccatctg      480
cgatcaaatt tttcattggt atggtcatga agaacggcaa aggtagattc aacccgcagg     540
actcggaagc aactttaaag aggattttga cggaacagca tcccgaatat gcaaatagtc     600
agaagtgata gagatgtatt agattttgtt taagtgcatc cgatagagca tacactcgta     660
atgatataat tcatctcata tatcgcaacg atttttatggt ccgcacgact taacgggcca    720
tgtacatcat ttgcgtggta ttcgtttacc agcccatgaa tcactgattg attattgagg     780
```

```
tcaatatgta tattagtatg cgtaacgcta caggtatggt tctccaactg ttctgggagt    840
ctgggactca tggagaaagc cgcaccacgg ttctcttcgg gctagggtaa cttgatgcgg    900
cgctaatttg atgaaaacac cataaaggca tacgatattt ggctttagtg cgccatcaaa    960
ccttgtctgt tgtgagcaag cacttagggc ttcatatcta gggcgtcctc tttgggatgg   1020
gactgcgatt tctctctcga cttccgttgg ttatcgacac tttcctttgt acgtttttgt   1080
cgttcgtgca ttttccacgg taatatatta tttcttggta cgtatagatt ttcatctccc   1140
tctaagctga tctgaggact aaacttatat tatagtcgta gcgatgcaga tgtcagtata   1200
gttttatttc gggcgaatgt ttaacgaata tgactcggtt cagtttgatt gttgcttgga   1260
atagttgagc tgatattagt tgtgtatagt                                    1290

<210> SEQ ID NO 39
<211> LENGTH: 1003
<212> TYPE: DNA
<213> ORGANISM: Lipomyces starkeyi

<400> SEQUENCE: 39
gggcaattgc aaaatggtct tgctattgcg gacttacgct ggatgttaag gcatatatta     60
tgcgtacagc taaaaaaacg cggggggcca tagtgttata tattacagag cggggggcga    120
cagtagctgg gcagtgctgc tggtcacaac accataactt atattgaatt cgaagatgat    180
ggctataatt cacacagaat tggcctcgaa agacagtgac ccccacgagg ttttgagtag    240
tcgagcagct ctgcatgtag tagctcacgc agcggaggga agacacggtg ggaggttgtc    300
cggaaggttt cgtcattggt tgggctccgc ctaacggtag atagtcagcc cgcactcaca    360
aaacgctaac agaacgaagc actcccgtgc gctcccaaa gctacccaga taaatagacg    420
gtgcagtcct gcctcacact tcctctttcc ctgtccaccc cttatcctgc ggtttagttt    480
tcccaatcgc tctttctata tttcaatttg tcacaatcca tctctgcaat tgtcaatatg    540
tccgaacctg tgtatgtata tgtcttttct ttgggttgtc gttccgtgac gcgggtagta    600
gcccagtcga tactgcgagc accgcatcca cagcaaagtt tgtagatctt ggcctagtgc    660
gttgaatcta tacatactgt cgtagtatgt gcatttggat ggagtgcttt cagggtttga    720
ctgtttctcg tccgcgtgat gttgcattgt tcaaattaat tgatgctgac ttgagcgccc    780
gtctcgctgg cctcgccggc ggatttacgc gcaattctta tcccagtggt ggtatgtgat    840
gattgattta ttatttatga accccaacat tgtttttata tgcagcttct ctcttgcgtg    900
taattgaaga tatactgcaa ttatcacacc tatggtttgc tatatgtgga ctgaactcac    960
atgatttgtt gcagatattg gtctcatcgg cttggccgtc atg                    1003

<210> SEQ ID NO 40
<211> LENGTH: 1157
<212> TYPE: DNA
<213> ORGANISM: Lipomyces starkeyi

<400> SEQUENCE: 40
tcgccaggct cggggattca acaaggtatt tcatttgtat tttattgctc tcgtgttaat     60
gatcagactg ctaagtagcc tcagaccgca atcccgttct tagtcgggac aaaatatgac    120
acatttgcac aattcccaag agaagatcag gaagaaataa cgaaacaggt acataggcac    180
aatccgtgag gatcgtatag ccactaaaga actgtaggcg cggaggtttg cgaaggtcat    240
gaaagctagt ttaatatttt gttcaacgag ccactctatc aacattcaga aggttagcca    300
acggtcgcac attcatcttt ccatactaac gtgtgaatta ttttaataga tttttaagat    360
```

```
cgttttatcg aaggcatttg aattgaaatg tgtgattccc gagatagcta ccattggtga    420
tcccatccta ctataccacg atgtgtaagc gacacgagga taacattatg gaatgcacga    480
cgtccacttt atgggacaat attacaatta tttctcccta ttgcgcacga acatgactga    540
atttttatgg tggagatgcg aggttgttaa tttcggtatc agcggtcatt cattgctaat    600
tacatgaggt tgttcatata ttggttccac gtgaattatt ctaccacgta aagaatgcg     660 gtctattaaa taccattggt catgccacgc tcgatataat ggacagcacg tcgtcgtaga    720
cgacgattac cgtgatgcta actggcatca gaaaagcata ccccagtagt cttatatctt    780
gggacattcc caagggcat tatgatagca catacaaagt tgaagtaaaa aattaataat     840
cagacctcga acgattgatt ttcactgtgg ccctgtcgag gacttgagac ccgccaccga    900
cgcgcgttac ccggggcagg ggatgggagt cagcaaggtt gtccggttct gtgggcttct    960
tcgttaattg taataagatc cctctgtcct gtccacaact tgccccccctc acatacattt   1020 ataccatcct tgctcccaat catcgactaa gttctttaca tcgcatccac cattgcaagt   1080
agtgactagt ttgtcgagat tgttttctgt cagtttttatt gtccgtgatt gttggaaacg   1140
tttatcaatt catcatg                                                   1157

<210> SEQ ID NO 41
<211> LENGTH: 1564
<212> TYPE: DNA
<213> ORGANISM: Lipomyces starkeyi

<400> SEQUENCE: 41
gctggacagt agatcggccg agaccgaatt ggttcactag gtcgaagtca acaacaatag     60
catcggacga agaagaaatt gactatcaag atgacagtga tgaatttgag aatgcgtcgc    120
ccttgcaagg gagaaagaga ctcgggtcat ccgaccacga cgaccaccca gctaagaaat    180
ctagagcatg cacgacgtct tatgtaccta gagaagtgag tagaccttgc tccggccgga    240
attctcctga ttttattgaa gtggtggacg agctctctat gacagtgtcg cttgatcgga    300
agcgattagg cgacctgacc aaccatagcc gcgatgcggt aaagaagacg acaagcaata    360
ccagttcaaa tggacaccaa agaaagggaa gctataaagg cagaaaagta tctagtgaac    420
aagaaaataa tgtcgaggag gaagatgagg atgaactttt tgcattaaaa ggtctcagtt    480
atcctataga ttcgtcgcca cgtttgtaat caattgtgaa tcgtgaatcg atagtgaata    540
cgtatcattt ctcggcgcca tacattgcgt gatttgagct acttaaatcc attgtaaaat    600
ataccgtctt atcctatgct cctttttaatg taactgacta actgagatcc gattgccatg    660
acaccattca gttggactcc gatgattccg agcccgcggg tccaaagggg cgtacgaaca    720
gcgtatttca ccatgattga gggtgtccgg agcaacgttg tggctaatta agtaagggga    780
tcgctgcagg tatgatagga aactaaatct gcagagaact tgaatggtag taagaagcag    840
atgctgaagt tattttatag agacagtgga ctgggtcgac ttgatacagc gtgtgaggat    900
tgctgatcag caggtagaaa aaggttaacg gctcgcctat atgttataat gcgacttcgg    960
caaaacgcgg aagcagaaga ccttatgcct ttgctgcaga cgacagacac gactagtatc   1020
tcacaggtgg tcaattacga gaatatttgc gagaacagct gaataaataa tgatactgtg   1080
ctctagaatc aaattgggag ccggactgtc acaaccgatc tcgggcagcg ccaatccgac   1140
gctacgctta agagccagct gttactgaga ccatcacagt actgagacca tcacagtata   1200
cgtggagtag caccagtaag cagtagtatg aaactaataa caataatatg attctgccga   1260
```

```
ctgatctatc aaggttgtct gcctcatagt tcgagcagca gtcaacgcat gtgctcacga    1320
cattggttta tgaagcgtag cgtgggcgag ttggtgcgag agctcgtcgg gcgttgtcgg    1380
gggggccact cagcgacccg tctgccttga tgcgcccacg ccttacggcc agcactcgcc    1440
cgagccggca aacctcctga tcgtccccat atattcatat accgcccaa atcttctcct    1500 cttcctcagt cataaccatt caatttatct gctccacatc acatccatct actaaatgac    1560
aatg                                                                1564
```

<210> SEQ ID NO 42
<211> LENGTH: 1173
<212> TYPE: DNA
<213> ORGANISM: Lipomyces starkeyi

<400> SEQUENCE: 42

```
tacggacaag agcagcatat gcggatacgg cttgacggag tatacgtggt cagccaagtc      60
ggcgttccgg tcggtgacca acgattcgag gaagtcccga tacgacacag cgcactgaaa     120
atctccggcc ggcgccgatt cgtgtaggag tcgatcggga actccaccca cgtcttcgcc     180
gacgtcggtc gaagaggtcg ccgtgcgcca agtttcgtat tgccaacgag tctaaacact     240
gtgacaccct atgcagagcc agatcgacaa catcgacctc gagcgcgcgg tgtacgatgg     300
cgggcgcatc gtcaatgcat caatatagtt ctcgaagctc gttcgcggga aatgctgtaa     360
ctcgtacacg aacgcgagca tgctgcaggc agcattgtca agtaaagtg acagatgaat      420 gtaatgtaca ctaaacttct tgacgttgca ggcctgtaac actaggtcat tcccgcacgc     480
ttcgcggttc atgcctgcga atgaacgcg aatgaagtcc cggatgaggg caggagatga      540
acgagtgccg tacactcatc ttctgacaat accgtgtctc catcgggaac catctctaag     600
tcgagataga accgaaagct attgcgtgtc gagatgattt tgtaaatact gcaagggatt     660
ggccgtggga tcagataatc gtataatgcc cttggcgtgc acacaaggaa cgatttccgt     720
aagtacgcct ccagttttta ttgccggcac attactgaca aaaggtatat acatattaaa     780
ccagctggac aatgcaaatt ttaaaggaga actcaattgc cttacaagtc ggcgagtgca     840
tgagactaac ataacaccta actatgaggt agtggcttgc caacggcgtt catgaagcat     900 gacccctaacc ctagtcggct cgtgtgttgc gatgccctag gtaatcattg tccaattcag    960
ctagggttga gatatccgcc cgtgactgtt ttttaacta ctgtgaggct acttactatg     1020
atggttgcat cttcaatctt gaatttacta ccactatcta acacataaca ccaatcgcgg    1080
aattaccaaa cgagccgaac ttggatcgta tcgcttggga gacggattct taaatatatc    1140
tatagcctca gatcatttct ataaataagt atg                                1173
```

<210> SEQ ID NO 43
<211> LENGTH: 1273
<212> TYPE: DNA
<213> ORGANISM: Lipomyces starkeyi

<400> SEQUENCE: 43

```
catcatcatg attttgccag ttcgccatct gttatggcgg ccgcagctcg cagtcgtggc      60
gctctgcggg ggggctcgcg cacgtttgat ccaaatgcgt ttggcagtga cagtgagcgg    120
agcgatgttg cactagaaga gttcatctac atgagcgagc tagacaatgg tgatgagcca    180
ggagatttgt ctacagttga aactacaccc ggtccaacgt cgacccctgt ttgggcgggc    240
aagttccata gcaaatttccc attgtcagct tttaggaata gctctagcat gcagtataga    300
agtatatagt acatatgtca tgtttcattt tcatttgtca ttaattgcga tggaaggtcg    360
```

```
gggtgttatt gtttatgtga atcgtatttg gcgattttt ttcggtttct cacatattgc    420
gattttgatt tttaatgtta tgtcattatt tgcgccggct attacctgga ttttatgtca    480
ttcagacgcg ccttcattta tttgtttata tttgcgacgg caaaaaattg attacagtgc    540
tcgtgctatg ttgcgaaaaa taaattactt gtttattaac tggatgatgc acaaggtatc    600
ataccgcctg ccatggatat ttgaagttgg catgcactga ttaattaaca tccgagtacg    660
agccaatgac tcgcattcgg ccaggcacgc agtcgaagac gtcagcatac gctgcgaatg    720
taacgacatg acgggtctcg tacctggccc atggattgcg caattcaggg gcgggagcgt    780
gaatgagcag ttaaagttgc cgttgcttta actgtgtggg ccacaacatt caaggttcgg    840
aaatatcaca acgcgttaca aaaatatcaa cacttaaggt ccgtcgtgcg gtaccaggta    900
cacgacaggt gcttgctgtc cctccgccac atccttctag agtactaaac aaattatatc    960
tgtatctaat cctgccggaa taatggtaat acataattta taaggcccga cgtgttaatt   1020
cacgggcaac tagagcatat ctactatcat gcgatacaag tgcggcacta tagagtttgg   1080
cctccggttg atatttctaa atgttttcgt tctgcgtgtg ctgataactt gtctaaaaat   1140
tttgtccgcg tcctggccgc tcttttgctc tcctttgttt gccggcctcg agtaaaatcc   1200
tatttatcct ctctgcgctc ctccgaccga aaagcatctg gcccgcattc acaactcata   1260
cgcatatatc atg                                                      1273

<210> SEQ ID NO 44
<211> LENGTH: 1203
<212> TYPE: DNA
<213> ORGANISM: Lipomyces starkeyi

<400> SEQUENCE: 44
tggctaaaga gctgcccaat ccacattact gcaatctgat tactgcactg gcaagaatta     60
cccttgagtc gggcgcctcg gccgtcatcg accaactaac tgcggaccaa agacaaatac    120
tgaaaaggca ttcgtatttg aatggcaacg acaacaccct taggattcta gaaaataaat    180
tacttgatat ctgtgaagaa ttttaaaaat cttgattcga tagccacaat tctgacattt    240
aagggatatt actattagac gatcgtgtat tgattcggac tgactgacat tactttcagg    300
tgtcttttct ggctgcttta gctaaagttg caacagttaa ctggcttgac agcaacatag    360
ttaggaattg ctaataaaac tatattcatg atttacaatg atgcgtactg cctctccatg    420
gattccaagg cagcaatcgc ggaagtgact ccgcatgatt gcacgcagga ggcatcccgc    480
gtactagaga accggccaac ttattgacgt cacatgtctg caatggaagc agttggcctc    540
gaccatgata caattaatat atagcagtaa attatcaagc cagagctagc atggggccgt    600
tcggaaatag tttgtatttg tgtttgtgtt acggcaattt cggactctcc gtcgaatgaa    660
ctgaaaccgg caatggcgtt tagaaaatgc taaggcttat tatgtagtgt cgatagagtt    720
ccaataaacg gctctaatga gcttagcgtg ctagtcgttt ccggacatag gcgctaatac    780
tcgtatttgc attcctcatc tacatatgat ggggcatta aaaagtattg tattcaaaca    840
aaatgatgat gcgtataaat tcacaaaatt ataatcacaa tacctgtgtg tcgcagctac    900
tacagcacag tgcggtgttt ttgggttagg gccagattag tatggcccga aagcttaac     960 tcgccagaat gaaagaaggt tctcggcgat gctagcacca acgagagcta acgtgaagtt   1020
tcttgaaccg tctggtatag ccaagtttca tgcagcctat gacctcatca caaggttgcg   1080
ttctacataa aagagtccgg tggagctcgc tttcgccttc tcctcctcaa atctacagtc   1140
```

```
tataaacgtc taccaccatta tacgttactt cgattctatt ctgctttcac tacatacaac    1200
atg                                                                   1203
```

<210> SEQ ID NO 45
<211> LENGTH: 1443
<212> TYPE: DNA
<213> ORGANISM: Lipomyces starkeyi

<400> SEQUENCE: 45

```
aacgcataga gcatagaatt atgttctcta ctcgcactat gtccgcgtac attactcgat      60
ttcggtcgtt tatgtaagaa aaacacagtc cagtcctcct cgcgggcatg agcctgatcg     120
ggcagcatga gttctgcgag caatctgtac atcaattagt ataacaatcg ttctctataa     180
taatacttct atatactctt cgtcgccttc tattcgcctt gggtactggt acttcacagt     240
cggtccctta tcgacgtcaa attcagcagc tagtacatac tcgacatgct cccccgcgcc     300
attcgcggtc acgcttagat acctgcatag tttccatcag ccaatatttta ctaatatgta    360
cgaattcagg acacaaacat atttcaattg gtcctgaagt atgatcgatt tcaccaatc     420
accaatattg gtgcttcatg ttggacgcca aattagtctt gaacatcgca gttgacgaaa     480
ccgagtaaac ctgtgcggct catttaaggg gtacccaagc agtccgataa agaggcctat     540
ctgaggcgca gtacgaccag tagcgttctg ctttatagga agttacacat tatttgcata     600
caccagaaca tagggctggt gacttgcctg aggttccgag atcaaccgaa caatgttggc     660
tcgttttagc tggttcaagt agccggggta aatggaatcg gaattagatc agagtgggat     720
tactagtact tttgcatacg cacgcgatgg tattgtaaat atagcctttg tgtcctcata     780
attagagctt actgtagcat tgtcagagtt ccaatttgaa caaaattata gacatgcttt     840
gattgtcagt cttcaatata gttgatggca tgcacttggt cggcgagtct acatttgcgg     900
tcaacaggcg ttagagcatt ggagatttgc ggcccttttc ttgacccatt cccacctgcc     960
gccgcctagg cttccgtgag ccgagagtgg ccgaatgtgc gattcgctaa taataatggt    1020
ctttgtcaac ttcgcaaccc atcgaggttg gagtttccag tgaggggcag aacgctctgg    1080
aaggcagaga caaaaagtca attgagtttc gcagagctcc actttatggc atatacctgt    1140
ccataaattg cagttatggt tttttgacta cgtattctcg gcactgagcc gcaaaccata    1200
cgtttctaag agattctggg tcagcaaaga aagtgatgga gcgccaaatg agccgcacga    1260
tggaagccga cagaaaaaaa ccgtcgcggc ctataatttt gagcggcacc tcacgtcgac    1320
tgcggagccc cctccaactt ttttttcctt cacattttca ccactgtaac atttccagtt    1380
gttcacttcc gactcaccaa ttgctcattt gcattatagt cgctaatcac ttcatttaca    1440
atg                                                                  1443
```

<210> SEQ ID NO 46
<211> LENGTH: 1205
<212> TYPE: DNA
<213> ORGANISM: Lipomyces starkeyi

<400> SEQUENCE: 46

```
ccatttagtc gccaatccaa ctaaaaagtg attcccagtt cacaagtgta tactacaatg     60
ttcaaacaag tgttattcac caacttcatt gtctatatta ccctggaacg ggaaaacttg    120
gtggatacgt gatgcagtga ctgtgtccta catagacagt cgataggaat tgggaaagaa    180
tgtctatata cttctatttta gcatttattc attattaggt agtgtccact atactggcgc    240
cttcgacttt ctttattcat ataaccagag tagcaccatc tgaatactga tttgcgtatt    300
```

```
actcatgcgc tgatggcatg tcgctggttt atagaaatta ccacgtaca tctcgatctt    360
cggatccgaa aatcgttcag gatacttcgt cacattgcac actagatgaa gctcttgggg    420
ggcagttaac gacgaagtca ttagctgcaa cgtaataaca gtgataagtt caagccaatg    480
gatgcgactg gtaatttgct gtgtaagtta cagtcaagac cctaacccga tgcaatatag    540
ggcccaattc aggcccaagt agagaacatt ggacgatcag aatggatggc cagatacggc    600
catatacaat ggtacgttac tggagcagta caaggctggt atcaatacaa ccattaatat    660
aggttaaaat tactcgtagt ttgcagaagg aggccgaata gattacataa gcgcttttgg    720
cgacagccgc atgctttcct gaagttatta atattaccgt gccttattct tatcctgtat    780
aagttaaatc tctattttgc ctttgtacga cctaatcgtg tcgggcgcaa ctaacgcgcg    840
atgcacctta tttcgttcgc gcagggcgtg tgctgagtgg cactaacgct atatacattt    900
tatttgttaa ctattcgacg ccaacgacag cggcaataca gtatctcgtt gtctaaatct    960
attcgatttg actattacga tcgggattgc catcgggtgg cagactcgtg acagggaatt   1020
ccttgttgca aattggaact gtaatcagcg tgccaaattt ccatcagctg tgtccttgtt   1080
cgggagccgt catatacaac gcagcgcgat tcctcttcga ccgttttcat ttcccaagtc   1140
gatcacttct attaaacatc gtttactttt gagaaagtca cgatttcttg cttgacttta   1200
ccatg                                                              1205

<210> SEQ ID NO 47
<211> LENGTH: 1203
<212> TYPE: DNA
<213> ORGANISM: Lipomyces starkeyi

<400> SEQUENCE: 47
atagcctgtc accgtcgcat cctctctgat tggcatataa gtagataccg ccacatttcg     60
ctgttgcttc tgcgatcaga tttaatcgca gatcaagctt acgcaactgg tgatgcgagc    120
ctgacgaatt ggtaaaaatc tcaattccat caagcgacat gtcaatatgc ggcgcgtctg    180
gagtgaataa ctcttcacat gtctctgctc ctacaacaca gtcttgagta gcgagcactg    240
catctccaaa gtcgacttca gtctgacccg tgatctccgt gattattcgg ggaagcgcat    300
acttctcaac gtggcgcgga cgcatccacg gagtgaagta cctcatttcg cgataattcc    360
cgtcattggc gagccacaac ttcgggcgaa tgaaaagaat gcggttactg taagagatca    420
tgcgacaatt gtatctgaca tttttgtgga ttactggcat tccgacatcg agtagaatat    480
cctggcaatc ttcatgctga agcaatttcg cgtacatttc ccacgaatgc aaatagatgt    540
caccttctag gaagtgatca agacagccat atccgctgca ggatgattag cgaattggcg    600
gaaagaatta tttacattat tttataacaa cgtacgtgat ttctaactcc ggacccactc    660
gaagagaagc gccttgagct ttggcttgga caatagaaga tacaattcgt tcgagattcc    720
cctcgaaatc gagggcccat tgattaaggg cgctgcgagc ggcaatggac gttagaataa    780
tcctctaatt taacaatgcg aagccggtga gagagtcgtt aagctagtct gtggagctga    840
caacaggaca agctgcaact atagtacatt aacgacttac catgtcgcaa gagtcacaaa    900
atgtcccatg ttgacttaga aagcgccgat ggaacttatg gtcttctatg tatatctaga    960
tatttagctc tggctctgac atctatgata gttgcctcga gcactgatcc ccccgcaga   1020
gatatgcgtc attcaagtgt ttagtactct tgtgagtcaa ttgtgatagt atcacgtgct   1080
tttgtgtgat ctttgtgagt actcatggct atcagtaaat aagtgcattt gtggccgata   1140
```

```
attatacgta tatgccacaa ccgcgactaa cttgtaatcg attggctgag agaggccgat    1200
atg                                                                 1203
```